(12) United States Patent
Sommer et al.

(10) Patent No.: US 8,252,534 B2
(45) Date of Patent: Aug. 28, 2012

(54) MICRO RNAS AND THEIR METHODS OF USE FOR THE TREATMENT AND DIAGNOSIS OF SCHIZOPHRENIA AND SCHIZOPHRENIA SPECTRUM DISORDERS

(75) Inventors: Steve S. Sommer, Duarte, CA (US); John J. Rossi, Alta Loma, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 12/484,145

(22) Filed: Jun. 12, 2009

(65) Prior Publication Data

US 2010/0009367 A1 Jan. 14, 2010

Related U.S. Application Data

(60) Provisional application No. 61/060,892, filed on Jun. 12, 2008.

(51) Int. Cl.
*C12Q 1/68* (2006.01)
(52) U.S. Cl. .............................................. 435/6.1
(58) Field of Classification Search .................. None
See application file for complete search history.

(56) References Cited

U.S. PATENT DOCUMENTS

| | | | |
|---|---|---|---|
| 2006/0135456 A1* | 6/2006 | Hannon et al. | 514/44 |
| 2007/0161004 A1* | 7/2007 | Brown et al. | 435/6 |
| 2008/0171715 A1* | 7/2008 | Brown et al. | 514/44 |

OTHER PUBLICATIONS

Hansen et al. Brain expressed microRNAs implicated in schizophrenia etiology. PLoS ONE (2007) Issue 9, e873, pp. 1-7.*
Zou et al. Association between two single nucleotide polymorphisms at corresponding microRNA and schizophrenia in a Chinese population. Mol. Biol. Rep. (2011) DOI 10.1007/s11033-011-1109-3, pp. 1-7.*
Xu et al. MicroRNAs and target site screening reveals a pre-microRNA-30e variant associated with schizophrenia. Schizophrenia Res. (2010) 119:219-227.*
Abelson, J.F., et al., "Sequence Variants in SLITRK1 are Associated with Tourette's Syndrome," Science 310:317-320 (2005).
Ambros, V., "MicroRNA Pathways in Flies and Worms: Growth, Death, Fat, Stress, and Timing," Cell 113:673-676 (2003).
Arisawa, T., et al., "A Polymorphism of MicroRNA 27a Genome Region is Associated with the Development of Gastric Mucosal Atrophy in Japanese Male Subjects," Dig. Dis. Sci. 52:1691-1697 (2007).
Bartel, D.P., "MicroRNAs: Genomics, Biogenesis, Mechanism, and Function," Cell 116:281-297 (2004).
Bentwich, I., et al., "Identification of Hundreds of Conserved and Nonconserved Human MicroRNAs," Nat. Genet. 37:766-770 (2005).
Berezikov, E., et al., "Mammalian Mirtron Genes," Mol. Cell. 28:328-336 (2007).
Blow, M.J., et al., "RNA Editing of Human MicroRNAs," Genome Biol. 7:R27 (2006).
Bushati, N., et al., "MicroRNA Functions," Annu. Rev. Cell. Dev. Biol. 23:175-205 (2007).

Cai, X., et al., "Human MicroRNAs are Processed from Capped, Polyadenylated Transcripts That Can Also Function as mRNAs," RNA 10:1957-1966 (2004).
Chen, W. et al., "Mutation Screening of Brain-Expressed X-Chromosomal miRNA Genes in 464 Patients With Nonsyndromic X-Linked Mental Retardation," Eur. J. Hum. Genet. 15:375-378 (2007).
Chendrimada, T.P. et al., "TRBP Recruits the Dicer Complex to Ago2 for microRNA Processing and Gene Silencing," Nature 436:740-744 (2005).
Chu, C.Y., et al., "Translation Repression in Human Cells by MicroRNA Induced Gene Silencing Requires RCK/p54," PLoS Biol. 4:1122-1136 (2006).
Clop, A. et al., "A Mutation Creating a Potential Illegitimate microRNA Target Site in the Myostatin Gene Affects Muscularity in Sheep," Nat. Genet. 38:813-818 (2006).
Croce, C.M., et al., "miRNAs, Cancer, and Stem Cell Division," Cell 122:6-7 (2005).
Diederichs, S., et al., "Sequence Variations of microRNAs in Human Cancer: Alterations in Predicted Secondary Structure Do Not Affect Processing," Cancer Res. 66:6097-6104 (2006).
Du, T., et al., "microPrimer: The Biogenesis and Function of microRNA," Development 132:4645-4652 (2005).
Duan, R., et al., "Single Nucleotide Polymorphism Associated with Mature miR-125a Alters the Processing of pri-miRNA," Hum. Mol. Genet. 16:1124-1131 (2007).
Filipowicz, W., et al., "Mechanisms of Post-Transcriptional Regulation by microRNAs: Are the Answers in Sight?" Nat. Rev. Genet. 9:102-114 (2008).
Giraldez, a.J., et al., "MicroRNAs Regulate Brain Morphogenesis in Zebrafish," Science 308:833-838 (2005).
Gottwein, E., et al., "A Novel Assay for Viral microRNA Function Identifies a Single Nucleotide Polymorphism that Affects Drosha Processing," J. Virol. 80:5321-5326 (2006).
Griffiths-Jones, S., et al., "miRBase: Tools for microRNA Genomics," Nucleic Acids Res. 36:D154-158 (2008).
Haase, A.D., et al. "TRBP, A Regulator of Cellular PKR and HIV-1 Virus Expression, Interacts with Dicer and Functions in RNA Silencing," EMBO Rep. 6:961-967 (2005).

(Continued)

*Primary Examiner* — Kenneth R. Horlick
*Assistant Examiner* — David Thomas
(74) *Attorney, Agent, or Firm* — Perkins Coie LLP; Lauren Sliger

(57) ABSTRACT

A method of diagnosing, assessing susceptibility, and/or treating schizophrenia involving the identification and/or observation of microRNAs (miRNA) and variant miRNA are provided. Micro RNAs alleles associated with schizophrenia and schizophrenia spectrum disorders were identified and ultra-rare variants in the precursor or mature miRNA were identified. Functional analyses of ectopically expressed copies of the variant miRNA precursors demonstrate loss of function, gain of function and altered expression levels. The present invention also provides methods for selecting a preferred therapy for a particular subject or group of subjects or individuals at risk for or suffering from schizophrenia or psychosis by use of miRNAs.

3 Claims, 55 Drawing Sheets

OTHER PUBLICATIONS

Hammond, S.M., et al., "An RNA-Directed Nuclease Mediates Post-Transcriptional Gene Silencing in Drosophila Cells," Nature 404:293-296 (2000).

Han, J., et al., "Molecular Basis for the Recognition of Primary microRNAs by the Drosha-DGCR8 Complex," Cell 125:887-901 (2006).

Han, J., et al., "The Drosha-DGCR8 Complex in Primary microRNA Processing," Genes Dev. 18:3016-3027 (2004).

Harrison, P.J., et al., "Schizophrenia Genes, Gene Expression, and Neuropathology: On the Matter of Their Convergence," Mol. Psychiatry 10:40-68 (2005).

Hatfield, S.D., et al., "Stem Cell Division is Regulated by the microRNA Pathway," Nature 435:974-978 (2005).

Hu Z., et al., "Common Genetic Variants in Pre-microRNAs Were Associated with Increased Risk of Breast Cancer in Chinese Women," Hum. Mutat. 30:79-84 (2009).

Hu, Z., et al., "Genetic Variants of miRNA Sequences and Non-Small Cell Lung Cancer Survival," J. Clin. Invest. 118:2600-2608 (2008).

Hutvagner, G., et al., "A Cellular Function for the RNA-Interference Enzyme Dicer in the Maturation of the let-7 Small Temporal RNA," Science 293:834-838 (2001).

Hutvagner, G., et al., "A microRNA in a Multiple-Turnover RNAi Enzyme Complex," Science 297:2056-2060 (2002).

Jablensky, A., "Epidemiology of Schizophrenia: the Global Burden of Disease and Disability," Eur. Arch. Psychiatry Clin. Neurosci. 250:274-285 (2000).

Jazdzewski, K., et al., "Common SNP in pre-miR-146a Decreases Mature miR Expression and Predisposes to Papillary Thyroid Carcinoma," Proc. Natl. Acad. Sci. USA 105:7269-7274 (2008).

Jentsch, J.D., et al., "Enduring Cognitive Deficits and Cortical Dopamine Dysfunction in Monkeys After Long-Term Administration of Phencyclidine," Science 277:953-955 (1997).

Jin, P., et al. "Biochemical and Genetic Interaction Between the Fragile X Mental Retardation Protein and the microRNA Pathway," Nat. Neurosci. 7:113-117 (2004).

Karube, Y., et al., "Reduced Expression of Dicer Associated with Poor Prognosis in Lung Cancer Patients," Cancer Sci. 96:111-115 (2005).

Kawahara, Y., et al., "Redirection of Silencing Targets by Adenosine-to-Inosine Editing of miRNAs," Science 315:1137-1140 (2007).

Kawahara, Y., et al., "RNA Editing of the microRNA-151 Precursor Blocks Cleavage by the Dicer-TRBP Complex," EMBO Rep. 8:763-769 (2007).

Khvorova, A., et al., "Functional siRNAs and miRNAs Exhibit Strand Bias," Cell 115:209-216 (2003).

Kim, V.N., "MicroRNA Biogenesis: Coordinated Cropping and Dicing," Nat. Rev. Mol. Cell. Biol. 6:376-385 (2005).

Klein, M.E., et al., "Role Reversal: The Regulation of Neuronal Gene Expression by microRNAs," Curr. Opin. Neurobiol. 15-507-513 (2005).

Lai, E.G., "MicroRNAs: Runts of the Genome Assert Themselves," Curr. Biol. 13:R925-R936 (2003).

Landthaler, M., et al., "The Human DiGeorge Syndrome Critical Region Gene 8 and Its D. Melanogaster Homolog are Required for miRNA Biogenesis," Curr. Biol. 14:2162-2167 (2004).

Lee, Y., et al., "MicroRNA Maturation: Stepwise Processing and Subcellular Localization," Embo J. 21:4663-4670 (2002).

Lee, Y., et al., "The Nuclear RNase III Drosha Initiates microRNA Processing," Nature 425:415-419 (2003).

Liu, J., et al., "A Role for the P-Body Component, GW182, in microRNA Function," Nat. Cell. Biol. 7:1261-1266 (2005).

Martin, M.M., et al., "The Human Angiotensin II Type 1 Receptor +1166 A/C Polymorphism Attenuates MicroRNA-155 Binding," J. Biol. Chem. 282:24262-24269 (2007).

Mattick, J.S., et al., "Small Regulatory RNAs in Mammals," Hum. Mol. Genet. 14:R121-R132 (2005).

Mishra, P.J., et al., "A miR-24 microRNA Binding-Site Polymorphism in Dihydrofolate Reductase Gene Leads to Methotrexate Resistance," Proc. Natl. Acad. Sci. USA 104:13513-13518 (2007).

Mourelatos, Z., et al., "miRNPs: A Novel Class of Ribonucleoproteins Containing Numerous microRNAs," Genes Dev. 16:720-728 (2002).

Naguibneva, I., et al., "The microRNA miR-181 Targets the Homeobox Protein Hox-A11 During Mammalian Myoblast Differentiation," Nat. Cell. Biol. 8:278-284 (2006).

Okamura, K., et al., "The Mirtron Pathway Generates microRNA-Class Regulatory RNAs in Drosophila," Cell 130:89-100 (2007).

Okamura, K., et al., "The Regulatory Activity of microRNA Species Has Substantial Influence on microRNA and 3' UTR Evolution," Nat. Struct. Mol. Biol. 15:354-363 (2008).

Palatnik, J.F., et al., "Control of Leaf Morphogenesis by microRNAs," Nature 425:257-263 (2003).

Pasquinelli, A.E., et al., "Conservation of the Sequence and Temporal Expression of let-7 Heterochronic Regulatory RNA," Nature 408:86-89 (2000).

Piercey, M.F., et al., "Dramatic Limbic and Cortical Effects Mediated by High Affinity PCP Receptors," Life Sci. 43:375-385 (1988).

Piskounova, E., et al., "Determinants of microRNA Processing Inhibition by the Developmentally Regulated RNA-Binding Protein Lin28," J. Biol. Chem. 283:21310-21314 (2008).

Purohit, D.P., et al., "Severe Cognitive Impairment in Elderly Schizophrenic Patients: A Clinicopathological Study," Biol. Psychiatry 33:255-260 (1993).

Rehwinkel, J., et al., "A Crucial Role for GW182 and the DCP1:DCP2 Decapping Complex in miRNA-Mediated Gene Silencing," RNA 11:1640-1647 (2005).

Ro, S., et al., "Tissue-Dependent Paired Expression of miRNAs," Nucleic Acids Res. 35:5944-5953 (2007).

Ruby, J.G., et al., "Intronic microRNA Precursors that Bypass Drosha Processing," Nature 448:83-86 (2007).

Ruvkun, G., "Molecular Biology. Glimpses of a Tiny RNA World," Science 294:797-799 (2001).

Saunders, M.A., et al., "Human Polymorphism at microRNAs and microRNA Target Sites," Proc. Natl. Acad. Sci. USA 104:3300-3305 (2007).

Schwarz, D.S., et al., "Asymmetry in the Assembly of the RNAi Enzyme Complex," Cell 115:199-208 (2003).

Seitz, H., et al., "Argonaute Loading Improves the 5' Precision of Both MicroRNAs and Their miRNA Strands in Flies," Curr. Biol. 18:147-151 (2008).

Sethupathy, P., et al., "Human microRNA-155 on Chromosome 21 Differentially Interacts with its Polymorphic Target in the AGTR1 3' Untranslated Region: A Mechanism for Functional Single-Nucleotide Polymorphisms Related to Phenotypes," Am. J. Hum. Genet. 81:405-413 (2007).

Shen, J., et al., "A Functional Polymorphism in the miR-146a Gene and Age of Familial Breast/Ovarian Cancer Diagnosis," Carcinogenesis (2008).

Sobell, J.L., et al., "Novel Association Approach for Determining the Genetic Predisposition to Schizophrenia: Case-Control Resource and Testing of the First Candidate Gene," Am. J. Med. Genet. 48:28-35 (1993).

Sommer, S.S., et al., "A Novel Method for Detecting Point Mutations or Polymorphisms and Its Application to Population Screening for Carriers of Phenylketonuria," Mayo. Clin. Proc. 64:1361-1372 (1989).

Sommer, S.S., et al., "PCR Amplification of Specific Alleles (PASA) is a General Method for Rapidly Detecting Known Single-Base Changes," BioTechniques 12:82-87 (1992).

Sun, G., et al., "Cloning and Detecting Signature MicroRNAs from Mammalian Cells," Methods Enzymol. 427:123-138 (2007).

Viswanathan, S.R., et al., "Selective Blockade of microRNA Processing by Lin28," Science 320:97-100 (2008).

Xu, T., et al., "A Functional Polymorphism in the miR-146a Gene is Associated with the Risk for Hepatocellular Carcinoma," Carcinogenesis 29:2126-2131 (2008).

Yang, W., et al., "Modulation of microRNA Processing and Expression Through RNA Editing by ADAR Deaminases," Nat. Struct. Mol. Biol. 13:13-21 (2006).

Yi, R., et al., "Exportin-5 Mediates the Nuclear Export of Pre-microRNAs and Short Hairpin RNAs," Genes Dev. 17:3011-3016 (2003).

Ying, S.Y., et al., "Intron-Derived microRNAs—Fine Tuning of Gene Functions," Gene 342:25-28 (2004).

Yu, Z., et al., "Aberrant Allele Frequencies of the SNPs Located in microRNA Target Sites are Potentially Associated with Human Cancers," Nucleic Acids Res. 35:4535-4541 (2007).

Zeng, Y, et al., "Both Natural and Designed Micro RNAs can Inhibit the Expression of Cognate mRNAs When Expressed in Human Cells," Mol. Cell. 9:1327-1333 (2002).

Zeng, Y., et al., "Efficient Processing of Primary microRNA Hairpins by Drosha Requires Flanking Nonstructured RNA Sequences," J. Biol. Chem. 280:2759527603 (2005).

Zeng, Y., "Principles of Micro-RNA Production and Maturation," Oncogene 25:6156-6162 (2006).

Zeng, Y., et al., "Recognition and Cleavage of Primary microRNA Precursors by the Nuclear Processing Enzyme Drosha," Embo J. 24:138-148 (2005).

Zeng, Y., et al., "Structural Requirements for Pre-microRNA Binding and Nuclear Export by Exportin 5," Nucleic Acids Res. 32:4776-4785 (2004).

Zhang, R., et al., "Rapid Evolution of an X-linked microRNA Cluster in Primates," Genome Res. 17:612-617 (2007).

* cited by examiner

Figure 2A

SEQ ID NO. 1:
```
>hsa-let-7f-2
u    u   gu                   uuagggucauac
 guggga gag  aguagauuguauaguu              c
 |||||| |||  ||||||||||||||||              
 cacccu uuc  ucaucugacauaucaa              c
g      -   ug                   uagagguucuac
```

SEQ ID NO. 2:
```
Sp 11: G>A u    u   gu                   uuagggucauac
 guggga gag  aguaaauuguauagau              c
 |||||| |||  ||||  ||||||||||              
 cacccu uuc  ucaucugacauaucaa              c
g      -   ug                   uagagguucuac
```

SEQ ID NO. 3:
```
>hsa-mir-18b ug    --    u    c    u    ua  --g
  uguua  agg  gcau  uag  gcagu  gu    aagc
  |||||  |||  ||||  |||  |||||  ||    |||  a
  acggu  ucc  cgua  auc  cguca  ua    uucg
--     cu    c    a    c    uc  aga
```

SEQ ID NO. 4:
```
Stem-loop 32: A>G ug    --    u    c    u    ua  --g
  uguua  agg  gcau  uag  gcagu  gu    aggc
  |||||  |||  ||||  |||  |||||  ||    |:|  a
  acggu  ucc  cgua  auc  cguca  ua    uucg
--     cu    c    a    c    uc  aga
```

Figure 2B

SEQ ID NO. 5:

```
>hsa-mir-188 u  -  uc  ca  uc           gu       -ugag u
 gcuc cc  ucu  ca  ccugcaug ggaggg       c  u
 |||| ||  |||  ||  ||:||||| ||||||       |  u
 cgag gg  agg  gu  ggacguac ccucc        g  c
    c  c  -u  ac  uu           ac       caaaa u
```

SEQ ID NO. 6:

```
3p 60: C>T u  -  uc  ca  uc           gu       -ugag u
 gcuc cc  ucu  ca  ccugcaug ggaggg       c  u
 |||| ||  |||  ||  |||||||| ||||||       |  u
 cgag gg  agg  gu  ggacguau ccucc        g  c c  c  -u  ac  uu           ac       caaaa u
```

SEQ ID NO. 7:

```
>hsa-mir-224 ca          u  u         a u    ug  u
 gggcuuu  agucacuag ggu ccguuu g aga  au g
 |||||||  ||||||||| ||| ||:||| | :|| ||  u
 cccgaaa  ucagugauc ccg gguaaa c uuu  ua g
           ca          -  u         a - gu  c
```

SEQ ID NO. 8:

```
Stem-loop 41: G>A ca          u  u         a u    ug  u
 gggcuuu  agucacuag ggu ccguuu g aga  au a
 |||||||  ||||||||| ||| ||:||| | ||| ||  u
 cccgaaa  ucagugauc ccg gguaaa c uuu  ua g
           ca          -  u         a - gu  c
```

SEQ ID NO. 9:

```
>hsa-mir-325

----------a             cc  u  g  c       gu uu gug
           uacagugcuugguu  uag aggu u caguaa  g  u    a
           |||||||||||||| ||| |||| : ||:|||  :  |
           gugucacgaacuaa  auc uccu g gguaau  u  a    c
 ggucuggauc              cu  c  g  a       ug uu aua
```

Figure 2C

SEQ ID NO. 10:

Stem-loop 66/3p 6: G>A

```
----------a          cc  a    g c       gu uu gug
          uacagugcuugguu  uag aggu u caguaa  g  u   a
          |||||||||||||| ||| |||| | ||||| | | |
          gugucacgaacuaa  auc acca g auuauu  u  a   c
ggucucggauc          cu  c    g a       ug uu aua
```

SEQ ID NO. 11:

>hsa-mir-421

```
    ----g   uu     -      cua          a    aaa
        caca  guaggc cuca    aaugcaaguaga  aga   a
        ||||  |||||| ||||    ||||||||||||  |||   a
        gugu  caucog gggu    uuacagcaacu   acu   u
gguaccucua    cu     c      uaa          -    aag
```

SEQ ID NO. 12:

Stem-loop 73: G/A

```
    ----g   uu     -      cua          a    aaa
        caca  guaggc cuca    aaucuaguaga  aga   a
        ||||  |||||| ||||    ||||||||||||  |||   a
        gugu  caucog gggu    uuacagcaacu   acu   u
cucua         cu     c      uaa          -    aag
```

SEQ ID NO. 13:

4 nt downstream of the 3'end of stem-loop: G/A

```
    ----g   uu     -      cua          a    aaa
        caca  guaggc cuca    aaucuaguaga  aga   a
        ||||  |||||| ||||    ||||||||||||  |||   a
        gugu  caucog gggu    uuacagcaacu   acu   u
gguaccucua    cu     c      uaa          -    aag
```

SEQ ID NO. 14:

>hsa-mir-450a-2

```
-ccaaagaaa    u       uuu    c                aa
          gaugc aaacuau  ugcga gugucccuaauaugu  u
          ||||| ||||||| ||||| |||||||||||||||| a
          cuaug uuugaua  acguu uacaggggguauagua u
gguauaauaa    u      cuu    u                 aa
```

Figure 2D

SEQ ID NO. 15:

```
5p 4: T/C

-ccaaagaaa       u      uuu    u                        aa
         gaugc aaacuau   cgcga guguaccuaauaugu  u
         ||||| |||||||   ||||| |||||||||||||||  a
         cuaug uuugaua   acguu uacaggggguuaugua  u
gguauaauaa       u      cuu    u                        aa
```

SEQ ID NO. 16:

```
>hsa-mir-502 u              -              uau ug      uag  ugg
 gcuccccucucu aauccuugc   c  ggugc  ugc   c
 |||||||||||| |||||||||   |  |||||  |||   u
 cgaggggagaga uuaggaacg   g  ccacg  acg   c
u              c              --- gu      -ua  uaa
```

SEQ ID NO. 17:

```
Stem-loop 13: C>G u              -              uau ug      uag  ugg
 gcuccccucugu aauccuugc   c  ggugc  ugc   c
 |||||||||||| |||||||||   |  |||||  |||   u
 cgaggggagaga uuaggaacg   g  ccacg  acg   c
u              c              --- gu      -ua  uaa
```

SEQ ID NO. 18:

```
>hsa-mir-505 ac   u           g   a            ucug
gaugc  ccag ggggagccag aagu uugaugua       c
|||||  |||| ||||||||||| |||| ||||||||       c
cuacg  gguc cuccuuggguc uuca aacugca       a
        -a   u           g   c            uuug
```

SEQ ID NO. 19:

```
Stem-loop 8: C>T ac   u           g   a            ucug
gaugc  ucag ggggagccag aagu uugaugua       c
|||||  :||| ||||||||||| |||| ||||||||       c
cuacg  gguc cuccuuggguc uuca aacugca       a
        -a   u           g   c            uuug
```

Figure 2E

SEQ ID NO. 20:

```
>hsa-mir-509-1 c  - ug   c  - ug     a  g         --g  u
    caug ugu gug  guac cua c  cagac gug caaucau     ua a
    |||| ||| |||  |||| ||| |  ||||| |||:|||||||     ||
    guac aca uac  caug gau g  gucug cau guuagua     au a
         - g  gu   a  g gu     -  g            aaa  u
```

SEQ ID NO. 21:

```
stem-loop 54; ins TGA c  - ug   c  - ug     a  g         -----g  u
    caug ugu gug  guac cua c  cagac gug caaucau       ua a
    |||| ||| |||  |||| ||| |  ||||| |||:|||||||       ||
    guac aca uac  caug gau g  gucug cau guuagua       au a
         - g  gu   a  g gu     -  g           guaaaa  u
```

SEQ ID NO. 22:

```
>hsa-mir-509-2 caugc  - ug   c  - ug     a  g         --g  u
         ugu gug  guac cua c  cagac gug caaucau     ua a
         ||| |||  |||| ||| |  ||||| ||| |||||||     ||
         aca uac  caug gau g  gucug cau guuagua     au a
    ----c  g  gu   a  g gu     -  g            aaa  u
```

SEQ ID NO. 23:

```
sp 11; 'a' del caugc  - ug   c  - ug       g         --g  u
         ugu gug  guac cua c  cagacgug caaucau     ua a
         ||| |||  |||| ||| |  |||||||| |||||||     ||
         aca uac  caug gau g  gucugcau guuagua     au a
    ----c  g  gu   a  g gu       g            aaa  u
```

SEQ ID NO. 24:

```
Stem-loop 9; G/T caugc  -u ug   c  - ug     a  g         --g  u
          ugu ug  guac cua c  cagac gug caaucau     ua a
          ||| ||  |||| ||| |  ||||| ||| |||||||     ||
          aca ac  caug gau g  gucug cau guuagua     au a
    ----c  gu gu   a  g gu     -  g            aaa  u
```

Figure 2F

SEQ ID NO. 25:

hsa-mir-509-3

```
   -- ug    c   - ug         g       --g  u
     g  guac cua c  cagacgug caaucau   ua  a
     |  |||| ||| |  ||||||||  ||||||   ||
     c  caug gau g  gucugcau guuagua   au  a
   ua gu    a   g gu         g        aaa  u
```

SEQ ID NO. 26:

3p 13: C/T

```
   -- ug    c   - ug         g       --g  u
     g  guac cua c  cagacgug caaucau   ua  a
     |  |||| ||| |  ||:|||||  ||||||   ||
     c  caug gau g  guuugcau guuagua   au  a
   ua gu    a   g gu         g        aaa  u
```

SEQ ID NO. 27:

5p 22: G/A

```
   -- ug    c   - ug         g       --a  u
     g  guac cua c  cagacgug caaucau   ua  a
     |  |||| ||| |  ||||||||  ||||||   ||
     c  caug gau g  gucugcau guuagua   au  a
   ua gu    a   g gu         g        aaa  u
```

SEQ ID NO. 28:

5p 19: C/G

```
   -- ug    c   - ug         g       --g  u
     g  guac cua c  cagacgug caaugau   ua  a
     |  |||| ||| |  ||||||||  |||| ||   ||
     c  caug gau g  gucugcau guuagua   au  a
   ua gu    a   g gu         g        aaa  u
```

SEQ ID NO. 29:

>hsa-mir-510

```
       g  uc      -a    a gg           g  a
   gug ug  cuacuc  ggag gu  caaucacau u  a
   ||| ||  ||||||  |||| ||  |||||||||  |
   cac au  ggagag  ucuc ca  guuagugug a  u
       a  ga      aa    - aa           g  u
```

Figure 2G

SEQ ID NO. 30:

```
Stem-loop 6: G>A g  c       -a    a  gg          g a
gug uau cuacuc  ggag gu  caaucacau u a
||| ||: |:||||  :||| ||  ||||||||: |
cac aug gguyay  ucuc ca  guuaguyug a u
       a  a      aa   -  aa          g u
```

SEQ ID NO. 31:

```
Stem-loop 46/3p 4: T>C g  uc      -a    a  gg          g a
gug ug  cuacuc  ggag gu  caaucacau u a
||| |:  |:||||  :||| ||  || ||||:| |
cac au  gguyay  ucuc ca  gucagugug a u
       a  ga     aa   -  aa          g u
```

SEQ ID NO. 32:

```
>hsa-mir-660

----------cu    c     -caaac   a    c   c     gaau
           gcuc uucucc   ccau gcauau ggag agu      u
           |||| ||||||   |||| |||||| |||| |||      c
           cgag gggagg   ggua cguguy cuuc aca      u
gugcuacuguuc    u      acauu    -    u   c   aaac
```

SEQ ID NO. 33:

```
5p 15: C > T

----------cu    c     -caaac   a    u   u     gaau
           gcuc uucucc   ccau gcauau ggag ugu      u
           |||| ||||||   |||| |||||| |||| |||      c
           cgag gggagg   ggua cguguy cuuc aca      u
gugcuacuguuc    u      acauu    -    u   c   aaac
```

SEQ ID NO. 34:

```
>hsa-mir-888

--   ag g  c          a  c           uuag
     ggc  u cu uacucaaa ag ugucagucac     a
     ||| | || |||||||||| || ||||||||||     u
     ucg  a ga guggguau uc acaguçagug     u
   ac   ga g  a          c  c           uaca
```

Figure 2H

SEQ ID NO. 35:

```
Stem-loop 77: A/C

--    ag g  c         a  c            uuag
   ggc  u cu uacucaaa ag ugucaqucac      a
   |||  | || |||||||| || ||||||||||      u
   ucg  a ga guggguuu uc acaqucaqug      u
  cc   ga g  a         c  c            uaca
```

SEQ ID NO. 36:

```
>hsa-mir-890

--    ag  c       uq       c uc           uuag
   gga  ugc cuacu  gaaagg a agaugc          a
   |||  ||| |||||  |||||| | ||||||          u
   ucu  aug gauga  cuucc  u ucaaug          u
  au   ga  a       gu       c ua          uaca
```

SEQ ID NO. 37:

```
Stem-loop 66/3p 21: G/C

--    ag  c       ug       c uc           uuag
   gga  ugc cuacu  gaaagg a aguuqc          a
   |||  ||| ||||   |||||| | ||||||          u
   ucu  aug cauga  cuucc  a ucaaug          u
  au   ga  a       gu       c ua          uaca
```

SEQ ID NO. 38:

```
>hsa-mir-891b c  --a    u    uu  c  a              uucag
   cuu  auccu gcaac ac ug gucauuga        u
   |||  ||||| ||||| || || ||||||||        a
   gaa  ugggq uguug ug ac cggaacu         a
  a  aac    u    uu  u  a              uacaa
```

SEQ ID NO. 39:

```
Stem-loop 35: C/G c  --a    u    uu  c  a              u ag
   cuu  auccu gcaac ac ug gucauuga ug   u
   |||  ||||| ||||| || || |||||||| ||   a
   gaa  ugggu uguug ug ac cgguaacu ac   a
  a  aac    u    uu  u  a              u aa
```

Figure 2I

SEQ ID NO. 40:
>hsa-mir-892b

```
--u  aa  c              u    uuuau  a    u
  gc  ugc  cuacucagaaagg  gcca      gu  gau  u
  ||  |||  ||||||||||||||  ||||      ||  |||  u
  cg  acg  gauggucuuucc   cggu      ca  cug  a
acu  ga  a              u    -----  -    u
```

SEQ ID NO. 41:
3p 15: I/C

```
--u  aa  c       a    u    uuuau  a    u
  gc  ugc  cuacuc  gaaagg  gcca      gu  gau  u
  ||  |||  ||||||  ||||||  ||||      ||  |||  u
  cg  acg  gauggg  cuuucc  cggu      ca  cug  a
acu  ga  a       c    u    -----  -    u
```

SEQ ID NO. 42:
>hsa-mir-934 MI0005756

```
              u  u     c             a     uagu
agaaauaaggcu  c  gucua  uacuggagac  cugg        a
||||||||||||  |  |||||  ||||||||||  ||||        u
ucuuuauuccga  g  caggu  augaccucug  gacc        a
              g  g     a             a     caaa
```

SEQ ID NO. 43:
5p 1: I/G

```
              u  g     c             a     uagu
agaaauaaggcu  c  gucua  uacuggagac  cugg        a
||||||||||||  |  |||||  ||||||||||  ||||        u
ucuuuauuccga  g  caggu  augaccucug  gacc        a
              g  g     a             a     caaa
```

FIGURE 3A

SEQ ID NO. 44:

```
hsa-mir-509-3

-- ug    c  - ug        g       --g  u
    g  guac cua c  cagacgug caaucau   ua a
    |  |||| ||| |  ||||||| ||||||    ||
    c  caug gau g  gucugcau guuagua   au a
   ua gu    a  g  gu        g        aaa u
```

SEQ ID NO. 45:

```
   3p 13: C/T

-- ug    c  - ug        g       --g  u
    g  guac cua c  cagacgug caaucau   ua a
    |  |||| ||| |  ||:||||| ||||||    ||
    c  caug gau g  guuugcau guuagua   au a
   ua gu    a  g  gu        g        aaa u
```

SEQ ID NO. 46:

```
   5p 22: G/A

-- ug    c  - ug        g       --a  u
    g  guac cua c  cagacgug caaucau   ua a
    |  |||| ||| |  ||||||| ||||||    ||
    c  caug gau g  gucugcau guuagua   au a
   ua gu    a  g  gu        g        aaa u
```

SEQ ID NO. 47:

```
   5p 19: C/G

-- ug    c  - ug        g       --g  u
    g  guac cua c  cagacgug caaugau   ua a
    |  |||| ||| |  ||||||| |||| |    ||
    c  caug gau g  gucugcau guuagua   au a
   ua gu    a  g  gu        g        aaa u
```

FIGURE 4D

SiCheck-502-5p-si
SEQ ID NO. 48: TAGCACCCAGATAGCAAGGAT
               |||||||||||||||||||||
SEQ ID NO. 49: ATCGTGGGTCTATCGTTCCTA SiCheck-502-5p-mi
SEQ ID NO. 50: ATGCACCCTCTTAGCAAGGAT
               ||||||  |||||||||||||
SEQ ID NO. 51: ATCGTGGGTCTATCGTTCCTA SiCheck-502-3p-si
SEQ ID NO. 52: TGAATCCTTGCCCAGGTGCATTGCATT
               |||||||||||||||||||||||||||
SEQ ID NO. 53: ACTTAGGAACGGGTCCACGTAACGTAA SiCheck-502-3p-mi
SEQ ID NO. 54: ACAATCCTTGCCCACCAGCATTGCATT
               ||||||||||||   ||||||||||||
SEQ ID NO. 55: ACTTAGGAACGGGTCCACGTAACGTAA

FIGURE 6B

SEQ ID NO. 56:

```
            g   c     -a    a  gg          g a
       gug ugu cuacuc  ggag gu  caaucacau u a
       ||| |:: |:|||| :||| ||  ||||||||: |
       cac aug ggugag ucuc ca  gucagugug a u
        a   a     aa    -  aa          g u
```

SEQ ID NO. 57:
miR-510-G/A

```
            g   c     -a    a  gg          g a
       gug uau cuacuc  ggag gu  caaucacau u a
       ||| ||: |:|||| :||| ||  ||||||||: |
       cac aug ggugag ucuc ca  guuagugug a u
        a   a     aa    -  aa          g u
```

SiCheck-510-5p-si
SEQ ID NO. 58: GTGATTGCCACTCTCCTGAGTA
                |||||||||||||||||||||||
SEQ ID NO. 59: CACTAACGGTGAGAGGACTCAT SiCheck-510-5p-mi
SEQ ID NO. 60: CAGATTGCCTGACTCCTGAGTA
                ||||||| ||||||||||
SEQ ID NO. 61: CACTAACGGTGAGACGACTCAT SiCheck-510-3p-si
SEQ ID NO. 62: CCACTCTTAGAGGTTTCAATCA
                |||||||||||||||||||||||
SEQ ID NO. 63: GGTGAGAATCTCCAAAGTTAGT SiCheck-510-3p-mi
SEQ ID NO. 64: GGACTCTTACTCGTTTCAATCA
                ||||||| ||||||||||
SEQ ID NO. 65: GGTGAGAATCTCCAAAGTTAGT

FIGURE 8C

```
   SEQ ID NO. 66:  --    ag    c          ug          c   uc           uuag
                         gga   ugc  cuacu     gaaagg  a   aguugc         a
miR-890                  |||   |||  |||||     ||||||  |   ||||||         u
                         ucu   aug  gauga     cuuucc  u   ucaaug         u
                         au    ga   a         gu          c  ua         uaca SEQ ID NO. 67:  --    ag    c          ug          c   uc           uuag
                         gga   ugc  cuacu     gaaagg  a   aguugc         a
miR-890-G/C              |||   |||  ||||      ||||||  |   ||||||         u
                         ucu   aug  cauga     cuuucc  u   ucaaug         u
                         au    ga   a         gu          c  ua         uaca
```

```
                 SEQ ID NO. 68: CAACTGATGCCTTTCCAAGTA
SiCheck-890-5p-si               |||||||||||||||||||||
                 SEQ ID NO. 69: GTTGACTACGGAAAGGTTCAT SEQ ID NO. 70: GTACTGATCTGTTTCCAAGTA
SiCheck-890-5p-mi               ||||||   |||||||||||
                 SEQ ID NO. 71: GTTGACTACGGAAAGGTTCAT SEQ ID NO. 72: TCTACTCAGAAAGGGAATAGT
SiCheck-890-3p-si               |||||||||||||||||||||
                 SEQ ID NO. 73: AGATGAGTCTTTCCCTTATCA SEQ ID NO. 74: TgTACTCAGAAAGGGAATAGT
SiCheck-890-3pGC-si             |||||||||||||||||||||
                 SEQ ID NO. 75: AcATGAGTCTTTCCCTTATCA SEQ ID NO. 76: GGTACTCACTTAGGGAATAGT
SiCheck-890-3p-mi               ||||||   |||||||||||
                 SEQ ID NO. 77: AGATGAGTCTTTCCCTTATCA
```

FIGURE 9C

```
SEQ ID NO. 78:   --u  aa   c                       u       uuuau  a     u
miR-892b             gc   ugc  cuacucagaaagg  gcca         gu  gau  u
                     ||   |||  ||||||||||||   ||||         ||  |||  u
                     cg   acg  gaugggcuuucc   cggu         ca  cug  a
                 acu  ga   a                    u        ------  -  u SEQ ID NO. 79:   --u  aa   c                       u       uuuau  a     u
miR-892b-T/C         gc   ugc  cuacucagaaagg  gcca         gu  gau  u
                     ||   |||  ||||||  ||||||  ||||         ||  |||  u
                     cg   acg  gaugggcuuucc   cggu         ca  cug  a
                 acu  ga   a                    u        ------  -  u
```

SEQ ID NO. 80: ACATAAATGGCACCTTTCTGAGTAG
SiCheck-892b-5p-si            |||||||||||||||||||||||||
              SEQ ID NO. 81: TGTATTTACCGTGGAAAGACTCATC SEQ ID NO. 82: TCTACCCAGAAAGGAGCCAGTG
SiCheck-892b-3p-si            ||||||||||||||||||||||
              SEQ ID NO. 83: AGATGGGTCTTTCCTCGGTCAC SEQ ID NO. 84: TCTACCCgGAAAGGAGCCAGTG
SiCheck-892b-3pm-si           ||||||||||||||||||||||
              SEQ ID NO. 85: AGATGGGcCTTTCCTCGGTCAC SEQ ID NO. 86: AGTACCCAGTTTGGAGCCAGTG
SiCheck-892b-3p-mi            |||||||     ||||||||||
              SEQ ID NO. 87: AGATGGGTCTTTCCTCGGTCAC

FIGURE 10C

```
                                           u  u       c         a      uagu
       SEQ ID NO. 88:  agaaauaaggcu  c  gucua  uacuggagac  cugg       a
miR-934                ||||||||||||  |  |||||  ||||||||||  ||||       u
                       Ucuuuauuccga  g  caggu  augaccucug  gacc       a
                                           g  g       a         a      caaa u  g       c         a      uagu
       SEQ ID NO. 89:  agaaauaaggcu  c  gucua  uacuggagac  cugg       a
miR-934-T/G            ||||||||||||  |  |||||  ||||||||||  ||||       u
                       Ucuuuauuccga  g  caggu  augaccucug  gacc       a
                                           g  g       a         a      caaa
```

SEQ ID NO. 90: CCAGTGTCTCCAGTAGTAGACA
SiCheck-934-5p-si    ||||||||||||||||||||||
SEQ ID NO. 91: GGTCACAGAGGTCATCATCTGT SEQ ID NO. 92: TTAGTGTCTGGTGTAGTAGACA
SiCheck-934-5p-mi    |||||||    |||||||||||
SEQ ID NO. 93: GGTCACAGAGGTCATCATCTGT SEQ ID NO. 94: CCGTCCATTACTGGAGACTCT
SiCheck-934-3p-si    |||||||||||||||||||||
SEQ ID NO. 95: GGCAGGTAATGACCTCTGAGA

FIGURE 13B

```
              ug        --  u    c    u       ua  --g
SEQ ID NO. 96:  uguua   agg gcau uag gcagu   gu    aaac
                ||| :|  ||| |||| ||| |||||   :|    || a
                acggu   ucc cgua auc cguca   ua    uucg
              --        cu   c    a    c     uc  aga
```

Figure 17

Table 1a. Ultra-rare miRNA cohort-specific variants

| ID# | Disease | miRNA | Variant in mature miRNA | Variant in precursor | Gene pool | Novel mature miRNA documented[a] |
|---|---|---|---|---|---|---|
| S358 | Schizophrenia | let-7f-2 | 11 G>A | | 0/7,197 | yes |
| S418 | Schizophrenia | mir-18b | | 32 A>G | 0/7,197 | ? |
| S590 | Schizophrenia | mir-505 | | 8 C>T | 0/7,197 | ? |
| S356 | Schizophrenia | mir-502 | | 13 C>G | 1/7,197[b] | yes |
| S014 | Schizophrenia | mir-188 | 7 C>T (188-3p) | | 0/7,197 | yes |
| MC179 | Psychosis | mir-325 | | 66 G>A | 0/7,197 | ? |
| S711 | Schizophrenia | mir-660 | 15 C>T | | 0/7,197 | yes |
| S596 | Schizophrenia | mir-509-3 | 13 C>T (509-3p) | | 0/7,197 | yes |
| MC149 | Control[c] | mir-510 | | 48 T>C | 0/7,197 | ? | a: by functional analysis b: one otherwise healthy individual in the gene pool analysis, who has this variant, was found to have a history of depression; the extent of the depression requires further clarification c: this individual was ascertained as a control sample, but upon examination of medical history was found to have a history of depression; the extent of the depression requires further clarification

Figure 18

Table 1b. miRNA cohort-specific sequence variants found in the gene pool analyses

| ID# | Disease | miRNA | Variant in mature miRNA | Variant in precursor | Gene pool |
|---|---|---|---|---|---|
| S464 | Schizophrenia | mir-509-3 | 22 G>A (509-3-5p) | | 2/7,197 |
| MC527 | Control | mir-509-3 | 19 C>G (509-3-5p) | | 10/4,962 |
| MC333 | Control | mir-421 | | 73 G>A | 16/4,962 |
| MC40 | Control | mir-934 | 1 T>G | | 4/7,197 |
| MC93 | Control | mir-450-2 | 5 T>C | | 8/4,962 |

Figure 19

| | Table 2. X Chromosome MicroRNA Primers (miRBase V10.1) | | | | | | |
|---|---|---|---|---|---|---|---|
| # | miRNA | Oligo | SEQ ID NO. | Sequence | Size(bp) | $T_m$(°C) | PCR size(bp) |
| 1 | mir-221 | mir-221D1 | SEQ ID NO. 97: | CAGTTATTCAGAAACATTATAGG | 23 | 62 | 200 |
| | | mir-221U1 | SEQ ID NO. 98: | AGGCAGTTGTGTTGAAATAGTA | 22 | 60 | |
| 2 | mir-222 | mir-222D1 | SEQ ID NO. 99: | TTATTAAAGACTGCCCAATAATC | 23 | 60 | 195 |
| | | mir-222U1 | SEQ ID NO. 100: | CTTCCACAGAGCCCCTCC | 18 | 60 | |
| 3 | mir-188 | mir-188D1 | SEQ ID NO. 101: | AGCATACCCATATGTCGTGC | 20 | 60 | 182 |
| | | mir-188U2 | SEQ ID NO. 102: | TGGTGAAGGAGTGCGTATGT | 20 | 60 | |
| 4 | mir-98 | mir-98D1 | SEQ ID NO. 103: | GAGGCAACACTGCTAAGACT | 20 | 60 | 167 |
| | | mir-98U2 | SEQ ID NO. 104: | CTTTTGCCTGCTGCCCTTAT | 20 | 60 | |
| 5 | let-7f-2 | let-7f-2D1 | SEQ ID NO. 105: | CCAGAACAAGAACCTGAACAG | 21 | 60 | 184 |
| | | let-7f-2U2 | SEQ ID NO. 106: | CCTGATAGTTCCGAGTAGCT | 20 | 60 | |
| 6 | mir-223 | mir-223D1 | SEQ ID NO. 107: | ACATCTCCCAGGAAGATCTC | 20 | 60 | 192 |
| | | mir-223U1 | SEQ ID NO. 108: | GGCAGTCCATTCGTCATATC | 20 | 62 | |
| 7 | mir-325 | mir-325D1 | SEQ ID NO. 109: | ACCACTAGGCCTAAGTACCT | 20 | 60 | 198 |
| | | mir-325U1 | SEQ ID NO. 110: | GCTTAAATATAGGTTTTGAGATG | 23 | 60 | |
| 8 | mir-361 | mir-361D1 | SEQ ID NO. 111: | GATGCTTCTAAAGAAACGGTG | 21 | 60 | 160 |
| | | mir-361U1 | SEQ ID NO. 112: | TAGCAGTGGCACGCTTGAC | 19 | 60 | |
| 9 | mir-224 | mir-224D1 | SEQ ID NO. 113: | TCTGGTGCTTACCTACTGTC | 20 | 60 | 170 |
| | | mir-224U1 | SEQ ID NO. 114: | TGGGGACCCATCATCAAAAG | 20 | 60 | |
| 10 | mir-374a | mir-374D1 | SEQ ID NO. 115: | AGGAGCTCACAGTCTAACTG | 20 | 60 | 182 |
| | | mir-374U1 | SEQ ID NO. 116: | GTTCCTCACCTCTCTTGATG | 20 | 60 | |
| 11 | mir-384 | mir-384D1 | SEQ ID NO. 117: | GCCAGTTAGCATCTTGAAGG | 20 | 60 | 186 |
| | | mir-384U1 | SEQ ID NO. 118: | GTTCCTTGCCTTTTAACTAGTAT | 23 | 62 | |
| 12 | mir-220 | mir-220D1 | SEQ ID NO. 119: | TCCAGCTGACGCACTTGCT | 19 | 60 | 208 |
| | | mir-220U1 | SEQ ID NO. 120: | GATGCAGTAGGTCTCATTCG | 20 | 60 | |

Figure 19 (continued)

| | | | | | | | |
|---|---|---|---|---|---|---|---|
| 13 | mir-92-2 | mir-92-2D1 | SEQ ID NO. 121: | CTAAATATCAGAACTTACGGCT | 22 | 60 | 177 |
| | | mir-92-2U1 | SEQ ID NO. 122: | GTGAACACACCTTCATGCGT | 20 | 60 | |
| 14 | mir-19b-2 | mir-19b-2D1 | SEQ ID NO. 123: | TGAGTGCTGGAGATACGCAT | 20 | 60 | 191 |
| | | mir-19b-2U1 | SEQ ID NO. 124: | CTCTTGGATAACAAATCTCTTG | 22 | 60 | |
| 15 | mir-106a | mir-106aD1 | SEQ ID NO. 125: | TTATGCACAAACTACAGTTCTC | 22 | 60 | 166 |
| | | mir-106aU1 | SEQ ID NO. 126: | AGAAGAGCTCCTGGAAGACT | 20 | 60 | |
| 16 | mir-424 | mir-424D2 | SEQ ID NO. 127: | GGGAGCGGGCACCTGGT | 17 | 60 | 178 |
| | | mir-424U3 | SEQ ID NO. 128: | GCTTCCTTCAGTCATCCAGT | 20 | 60 | |
| 17 | mir-105-1 | mir-105-1D | SEQ ID NO. 129: | AATGGCTTTGGTCCAGAAGC | 20 | 60 | 165 |
| | | mir-105-1U | SEQ ID NO. 130: | CTACTCCTATATATTGGATGTC | 22 | 60 | |
| 18 | mir-105-2 | mir-105-2D | SEQ ID NO. 131: | GAGTGGCTTTGTTCCAGAAG | 20 | 60 | 170 |
| | | mir-105-2U | SEQ ID NO. 132: | GTCTACTCCCTATAACCTGG | 20 | 60 | |
| 19 | mir-651 | mir-651D1 | SEQ ID NO. 133: | CTTGTGATGTAGATTAAATCGT | 22 | 58 | 368 |
| | | mir-651U1 | SEQ ID NO. 134: | CACTTTATTCATCCTGACTCT | 21 | 58 | |
| 20 | mir-532 | mir-532D1 | SEQ ID NO. 135: | TGTACACAAGCACACCTTCT | 20 | 58 | 328 |
| | | mir-532U1 | SEQ ID NO. 136: | GAAGCAGGACAGTCATCCA | 19 | 58 | |
| 21 | mir-660 | mir-660D1 | SEQ ID NO. 137: | GCACCTGACACTTTAATCTCA | 21 | 60 | 365 |
| | | mir-660U1 | SEQ ID NO. 138: | CTAATACCTCCACTAGATAGG | 21 | 60 | |
| 22 | mir-652 | mir-652D2 | SEQ ID NO. 139: | TGTTTGTGTGCTATGGCCAT | 20 | 58 | 449 |
| | | mir-652U2 | SEQ ID NO. 140: | GTTCTCCTATATGATGGCTC | 20 | 58 | |
| 23 | mir-934 | mir-934D1 | SEQ ID NO. 141: | TATGTATCTCGTGGATCTGC | 20 | 58 | 259 |
| | | mir-934U1 | SEQ ID NO. 142: | TTACAAGATAGGAAGTGCATAT | 22 | 58 | |
| 24 | mir-421 | mir-421D1 | SEQ ID NO. 143: | CATTGTCCGTGTCTATGGC | 19 | 58 | 345 |
| | | mir-421U1 | SEQ ID NO. 144: | AATTGGAGATGGTACTTGAGA | 21 | 58 | |

Figure 19 (continued)

| | | | | | | | |
|---|---|---|---|---|---|---|---|
| 25 | mir-766 | mir-766D1 | SEQ ID NO. 145: | TATACACAGAGGATTGCTTAG | 21 | 58 | 308 |
| | | mir-766U1 | SEQ ID NO. 146: | CCTCATTACTCTCATTTCCTG | 21 | 60 | |
| 26 | mir-450b | mir-450bD3 | SEQ ID NO. 147: | ATCGCTGACTTGTGTCACTA | 20 | 58 | 543 |
| | | mir-450bU2 | SEQ ID NO. 148: | TATTCTAGGCCCACTGCTG | 19 | 58 | |
| 27 | mir-890 | mir-890D1 | SEQ ID NO. 149: | TTCAGGGTTCAGGCATCCT | 19 | 58 | 291 |
| | | mir-890U1 | SEQ ID NO. 150: | ACACCTAAGGTTCAGGTGG | 19 | 58 | |
| 28 | mir-888 | mir-888D1 | SEQ ID NO. 151: | GACATCATGCTGTGCTCAG | 19 | 58 | 279 |
| | | mir-888U1 | SEQ ID NO. 152: | TGCCTGAATTCCAGGTGGT | 19 | 58 | |
| 29 | mir-892a | mir-892aD1 | SEQ ID NO. 153: | TCCAGATTCAGGCATCCTG | 19 | 58 | 289 |
| | | mir-892aU1 | SEQ ID NO. 154: | TTAAGGATGCCTGAGGTTCA | 20 | 58 | |
| 30 | mir-892b | mir-892bD1 | SEQ ID NO. 155: | TCAAATTGTTCAGGCATCATG | 21 | 58 | 279 |
| | | mir-892bU1 | SEQ ID NO. 156: | ACATGGCCAGCTAGGTTCT | 19 | 58 | |
| 31 | mir-891b | mir-891bD1 | SEQ ID NO. 157: | TAGCTACATAGGTCGTGAATA | 21 | 58 | 315 |
| | | mir-891bU1 | SEQ ID NO. 158: | CTACTACCAGTATCACTACAA | 21 | 58 | |
| 32 | mir-891a | mir-891aD1 | SEQ ID NO. 159: | CATGCTGATAGTTACACAGG | 20 | 58 | 319 |
| | | mir-891aU1 | SEQ ID NO. 160: | ACTACCAGTGTCACTACAAG | 20 | 58 | |
| 33 | mir-509-2 | mir-509-2D2 | SEQ ID NO. 161: | ccaaattccaatggccacg | 19 | 58 | 521 |
| | | mir-509-2U2 | SEQ ID NO. 162: | atttggatgttggagtaggc | 21 | 58 | |
| 34 | mir-509-3 | mir-509-3D1 | SEQ ID NO. 163: | TCTGTGAGTAACAGGACCTA | 20 | 58 | 690 |
| | | mir-509-3U1 | SEQ ID NO. 164: | TGAGAAAGGAAGCTAACCATT | 21 | 58 | |
| 35 | mir-767 | mir-767D1 | SEQ ID NO. 165: | TGATATCTCCTCCAGCATCA | 20 | 58 | 331 |
| | | mir-767U1 | SEQ ID NO. 166: | TGATCTAAGAGTAGAGAGTCA | 21 | 58 | |
| 36 | mir-374b | mir-374bD1 | SEQ ID NO. 167: | GTAAAGTGTTTGTCATAGGCA | 21 | 58 | 329 |
| | | mir-374bU1 | SEQ ID NO. 168: | CCTACAATGTGCACCGGAT | 19 | 58 | |

Figure 19 (continued)

| | | | | | | | |
|---|---|---|---|---|---|---|---|
| 37 | mir-542 | mir-542D1 | SEQ ID NO. 169: | GGTGGGATTAGAGCTGAAG | 19 | 58 | 435 |
| | | mir-542U1 | SEQ ID NO. 170: | GGCATTCCCATTACACTCC | 19 | 58 | |
| 38 | mir-513-1 | mir-513-1D2 | SEQ ID NO. 171: | CAAGTTGCATTGTCCCTTGG | 20 | 60 | 486 |
| | | mir-513-1U2 | SEQ ID NO. 172: | TGGAGTAAAGCATTCCAGCT | 20 | 58 | |
| 39 | mir-20b | mir-20bD1 | SEQ ID NO. 173: | GTAGCAATGTCTTTGAATATTC | 22 | 58 | 189 |
| | | mir-20bU1 | SEQ ID NO. 174: | TGTTGGGAACAGATGGTGG | 19 | 58 | |
| 40 | mir-362 | mir-362D1 | SEQ ID NO. 175: | ACATGCACACATACAAACACA | 21 | 58 | 199 |
| | | mir-362U1 | SEQ ID NO. 176: | ATAGCAAACACAAACATGTGAA | 22 | 58 | |
| 41 | mir-18b | mir-18bD1 | SEQ ID NO. 177: | ACCACTGAAATGTGTCCTATT | 21 | 58 | 209 |
| | | mir-18bU1 | SEQ ID NO. 178: | GAGAACTGTAGTTTGTGCATA | 21 | 58 | |
| 42 | mir-510 | mir-510D1 | SEQ ID NO. 179: | ATGTGCTAAGAAAAGCATACC | 21 | 58 | 219 |
| | | mir-510U1 | SEQ ID NO. 180: | AGAGGTTGTTTGAAAAGTGTG | 21 | 58 | |
| 43 | mir-363 | mir-363D1 | SEQ ID NO. 181: | TAGCTTACTGTAGCGCTGAT | 20 | 58 | 229 |
| | | mir-363U1 | SEQ ID NO. 182: | ACTTGTCCCGGCCTGTGG | 18 | 60 | |
| 44 | mir-503 | mir-503D1 | SEQ ID NO. 183: | TGCAATCTTGGGTCTCGCT | 19 | 58 | 239 |
| | | mir-503U1 | SEQ ID NO. 184: | GGGCAGTATTCCTGGCTAG | 19 | 60 | |
| 45 | mir-500 | mir-500D1 | SEQ ID NO. 185: | AAGCTCAAGAACTGTTCTCTT | 21 | 58 | 250 |
| | | mir-500U1 | SEQ ID NO. 186: | ATAAATACTTGTGGAATGGATG | 22 | 58 | |
| 46 | mir-501 | mir-501D1 | SEQ ID NO. 187: | CAGAGATACTTTGCAGGAATG | 21 | 60 | 260 |
| | | mir-501U1 | SEQ ID NO. 188: | AAGAATGAATGAGGGTCAGAG | 21 | 60 | |
| 47 | mir-505 | mir-505D1 | SEQ ID NO. 189: | ATGATGCAAATGAGTATTAGGA | 22 | 58 | 270 |
| | | mir-505U1 | SEQ ID NO. 190: | TTCTAGATTATGGGTCATTCC | 21 | 58 | |
| 48 | mir-452 | mir-452D1 | SEQ ID NO. 191: | GCCAGCTGCACATTCCGA | 18 | 58 | 278 |
| | | mir-452U1 | SEQ ID NO. 192: | GTTGGTAAGCGTGCCAGG | 18 | 58 | |

Figure 19 (continued)

| | | | | | | | |
|---|---|---|---|---|---|---|---|
| 49 | mir-504 | mir-504D1 | SEQ ID NO. 193: | AAGAGACTTATCAGGATTGAG | 21 | 58 | 289 |
| | | mir-504U1 | SEQ ID NO. 194: | CCATCCATTTCCCACATAGA | 20 | 58 | |
| 50 | mir-502 | mir-502D1 | SEQ ID NO. 195: | TCACCTAATATTCCTGCACG | 20 | 58 | 299 |
| | | mir-502U1 | SEQ ID NO. 196: | GGTGATGTCTAGGCTCTCT | 19 | 58 | |
| 51 | mir-507 | mir-507D1 | SEQ ID NO. 197: | TGATGGTGGTGGCACTGAC | 19 | 60 | 310 |
| | | mir-507U1 | SEQ ID NO. 198: | TCCTAGTGGACTGAGAGTGT | 20 | 60 | |
| 52 | mir-545 | mir-545D1 | SEQ ID NO. 199: | CAAAGAACTGTGTAGGAAGGA | 21 | 60 | 320 |
| | | mir-545U1 | SEQ ID NO. 200: | TCATCACTCGACAGTGATGG | 20 | 60 | |
| 53 | mir-509-1 | mir-509D1 | SEQ ID NO. 201: | GTCCAGCATGGAAGTGGAG | 19 | 60 | 330 |
| | | mir-509U1 | SEQ ID NO. 202: | TGGATTGGATTCTGCAGAAGT | 21 | 60 | |
| | | mir-509D2 | SEQ ID NO. 203: | TGGACAAAGGACTTCTGTAG | 20 | 58 | ~920 |
| 54 | mir-450-2 | mir-450-2D1 | SEQ ID NO. 204: | TAGTGCATATTAGGAACACATC | 22 | 60 | 339 |
| | | mir-450-2U1 | SEQ ID NO. 205: | ATAGGTATATAGGGAGCATTCT | 22 | 60 | |
| 55 | mir-450-1 | mir-450-1D1 | SEQ ID NO. 206: | CACAGAAGTAAACCACAGATA | 21 | 58 | 349 |
| | | mir-450-1U1 | SEQ ID NO. 207: | TTGTGGTATAAAGGTGACCAA | 21 | 58 | |
| 56 | mir-448 | mir-448D1 | SEQ ID NO. 208: | CCAGGCCAGAAGAGGCTT | 18 | 58 | 369 |
| | | mir-448U1 | SEQ ID NO. 209: | AAGGTCATAGCAGTCAGTAC | 20 | 58 | |
| 57 | mir-508 | mir-508D1 | SEQ ID NO. 210: | AAGACCTGCCTATGGGAGT | 19 | 58 | 379 |
| | | mir-508U1 | SEQ ID NO. 211: | ACTGAAGAGAAGAAGTCCTC | 20 | 58 | |
| 58 | mir-506 | mir-506D1 | SEQ ID NO. 212: | CAGATTCTGGAGCAGATCTC | 20 | 60 | 389 |
| | | mir-506U1 | SEQ ID NO. 213: | CAGAACTACCCACTCAGTGA | 20 | 60 | |
| 59 | mir-513-2 | mir-513-2D1 | SEQ ID NO. 214: | GAGTCCACAGTTCCTATGTA | 20 | 58 | 399 |
| | | mir-513-2U1 | SEQ ID NO. 215: | CTCACTTGGGGCAGGATG | 18 | 58 | |

Figure 20

Table 3. Variants found in cases and controls[a]

| ID# | miRNA | Variant in Precursor | # of schizophrenia patients with the variant (n=193) | # of control patients with the variant (n=191) |
|---|---|---|---|---|
| S329; MC124; MC178; MC235 | mir-890 | 66 G>C | 1 | 3 |
| many | mir-888 | 77 A>C | 39 | 32 |
| S014; S104; S319; S599; MC73; MC207; MC424; MC515 | mir-891b | 35 C>G | 4 | 4 |
| S211; S508; MC129; MC162; MC285; MC398 | mir-509-1 | 54 insTGA | 2 | 4 |
| S345; S433; MC348; MC370 | mir-509-2 | 9 G>T | 2 | 2 |

[a] all 5 variants were found with similar frequencies in cases and controls

Figure 21

Table 4 With 509-2

| ID# | Disease | Gender | Ethnicity | miRNA | Variant in mature miRNA | Variant in Precursor | # of schizophrenia patients with the variant (n=288) | # of control patients with the variant (n=192) | |
|---|---|---|---|---|---|---|---|---|---|
| S329; MC124; MC178 | schizophrenia & controls | all male | all Caucasian | mir-890 | | 66 G<C | 1 | 3 | |
| | schizophrenia & controls | all male | all Caucasian | mir-888 | | 77 A<C | 53 | 32 | |
| S599; S014; S104; S319; MC73; MC207 | schizophrenia & controls | all male | all Caucasian | mir-891b | | 35 C<G | 4 | 4 | |
| | schizophrenia & controls | all male | all Caucasian | mir-509-1 | | 54 insTGA | 3 | 4 | |
| 6 | 509-2 | g1461480 52t | in precursor; 11 bases upstream of the 5' end of the mature miRNA | 1/192 | 2/192 | S433; MC348; MC370 | NA | 1/94 | yes |

Figure 22

Table 5 Without 509-2

| ID# | Disease | Gender | Ethnicity | miRNA | Variant in mature miRNA | Variant in Precursor | # of schizophrenia patients with the variant (n=288) | # of control patients with the variant (n=192) |
|---|---|---|---|---|---|---|---|---|
| S329; MC124; MC178 | schizophrenia & controls | all male | all Caucasian | mir-890 | | 66 G<C | 1 | 3 |
| | schizophrenia & controls | all male | all Caucasian | mir-888 | | 77 A<C | 53 | 32 |
| S599; S014; S104; S319; MC73; MC207 | schizophrenia & controls | all male | all Caucasian | mir-891b | | 35 C<G | 4 | 4 |
| | schizophrenia & controls | all male | all Caucasian | mir-509-1 | | 54 insTGA | 3 | 4 |

Figure 23

Table 6. Target genes of miRNAs in which we found ultra-rare cohort-specific variants.

| Genes | Function | miRNAs with ultra rare variants have binding site in 3'UTR |
|---|---|---|
| CLCN5 | Chloride channel 5 (nephrolithiasis 2, X-linked, Dent disease) Mutations in this gene have been found in Dent disease and renal tubular disorders complicated by nephrolithiasis | Let-7f, miR-502, miR-18b, miR-660, |
| HMGA2 | HMG proteins function as architectural factors and are essential components of the enhancesome. Identification of the deletion, amplification, and rearrangement of this gene that are associated with myxoid liposarcoma suggests a role in adipogenesis and mesenchymal differentiation. | Let-7f, miR-505 |
| NRXN3 | Neurexins are a family of proteins that function in the vertebrate nervous system as cell adhesion molecules and receptors. | Let-7f |
| DISC1 | Disrupted in schizophrenia 1: The protein is involved in neurite outgrowth and cortical development through its interaction with other proteins. This gene is disrupted by a t(1;11)(q42.1;q14.3) translocation which segregates with schizophrenia and related psychiatric disorders in a large Scottish family. | Let-7f, miR-18b, miR-510, miR-188, miR-502 |
| NRG1 | Neuregulin 1: Interacts with the NEU/ERBB2 receptor tyrosine kinase to increase its phosphorylation on tyrosine residues. It induces the growth and differentialtion of epithelial, neuronal, glial and other types of cells. | miR-505 |
| MECP2 | Methyl CpG binding protein 2: Mutations of MECP2 are the cause of some cases of Rett syndrome, a progressive neurologic developmental disorder, and are one of the most common causes of mental retardation in females. | Let-7f, miR-188 miR-325, miR-18b |
| RGS4 | Regulator of G-protein signaling 4: It negatively regulates signaling upstream or at the level of the heterotrimeric G protein and is localized in the cytoplasm. | miR-18b, miR-502 |
| GRM3 | Glutamate receptor, metabotropic 3: L-glutamate is the major excitatory neurotransmitter in the central nervous system and activates both ionotropic and metabotropic glutamate receptors. Glutamatergic neurotransmission is involved in most aspects of normal brain function and can be perturbed in many neuropathologic conditions. | miR-325 |

Figure 24

| Table 7 Oligos used to clone pri-miRNA and probes for northern blots | | |
|---|---|---|
| hsa-let-7f-2 | | |
| | | |
| 5xho-let7f2 | SEQ ID NO. 216: | attatCTCGAGaatctctcaggtaactctcc |
| 3BamH-let7f2 | SEQ ID NO. 217: | attatGGATCCAGAGTTGCAGTCAGGAAATG |
| | | |
| 5x-Let7f2-si | SEQ ID NO. 218: | TCGAAACTATACAATCTACTACCTCA |
| 3s-Let7f2-si | SEQ ID NO. 219: | CTAGTGAGGTAGTAGATTGTATAGTT |
| | | |
| 5x-Let7f2-m-si | SEQ ID NO. 220: | TCGAAACTATACAATTTACTACCTCA |
| 3s-Let7f2-m-si | SEQ ID NO. 221: | CTAGTGAGGTAGTAAATTGTATAGTT |
| | | |
| Oligo for rmutagenesis | | |
| 5-let7f2G-A | SEQ ID NO. 222: | GGGATGAGGTAGTAAATTGTATAGTTTTAG |
| 3-let7f2G-A | SEQ ID NO. 223: | CTAAAACTATACAATTTACTACCTCATCCC |
| | | |
| 5x-let7f-mi | SEQ ID NO. 224: | tcgaGGGTATACGGTCTACTACCTCA |
| 3S-let7f-mi | SEQ ID NO. 225: | ctagTGAGGTAGTAGACCGTATACCC |
| | | |
| 5x-let7f-m-mi | SEQ ID NO. 226: | tcgaGGGTATACGGTTTACTACCTCA |
| 3S-let7f-m-mi | SEQ ID NO. 227: | ctagTGAGGTAGTAAACCGTATACCC |
| | | |
| let7f2 probe | SEQ ID NO. 228: | AACTATACAATCTACTACCTCA |
| | | |
| hsa-mir-18b | | |
| | | |
| 5Xho-miR18b | SEQ ID NO. 229: | tatCTCGAGCTACTGAGAACTGTAGTTTGTGCA |
| 3BamH-miR18b | SEQ ID NO. 230: | tatGGATCCACTGAAATGTGTCCTATTCAAATT |
| | | |
| 5x-18b-si | SEQ ID NO. 231: | tcgaCTAACTGCACTAGATGCACCTTA |
| 3s-18b-si | SEQ ID NO. 232: | ctagTAAGGTGCATCTAGTGCAGTTAG |
| | | |
| 5x-18b-mi | SEQ ID NO. 233: | tcgagaAACTGCACatcATGCACCTTA |
| 3s-18b-mi | SEQ ID NO. 234: | ctagTAAGGTGCATGATGTGCAGTTTC |
| | | |
| 5x-18bStar-si | SEQ ID NO. 235: | tcgaGCCAGAAGGGGCATTTAGGGCA |
| 3s-18bStar-si | SEQ ID NO. 236: | ctagTGCCCTAAATGCCCCTTCTGGC |
| | | |
| 5x-18bStar-mi | SEQ ID NO. 237: | tcgacgCAGAAGGccgATTTAGGGCA |
| 3s-18bStar-mi | SEQ ID NO. 238: | ctagTGCCCTAAATCGGCCTTCTGCG |
| | | |
| hsa-mir-505 | | |
| | | |
| 5Xho-miR505 | SEQ ID NO. 239: | tatCTCGAGCATACTGTCATTGAAAGCACTTAC |
| 3BamH-miR505 | SEQ ID NO. 240: | tatGGATCCTGAGCAAATGAATGGGAGCAGTAA |

Figure 24 (continued)

| | | |
|---|---|---|
| 5x-505-si | SEQ ID NO. 241: | tcgaAGGAAACCAGCAAGTGTTGACG |
| 3s-505-si | SEQ ID NO. 242: | ctagCGTCAACACTTGCTGGTTTCCT |
| | | |
| 5x-505-mi | SEQ ID NO. 243: | tcgatcGAAACCAcgtAGTGTTGACG |
| 3s-505-mi | SEQ ID NO. 244: | ctagCGTCAACACTACGTGGTTTCGA |
| | | |
| 5x-505Star-si | SEQ ID NO. 245: | tcgaACATCAATACTTCCTGGCTCCC |
| 3s-505Star-si | SEQ ID NO. 246: | ctagGGGAGCCAGGAAGTATTGATGT |
| | | |
| 5x-505Star-mi | SEQ ID NO. 247: | tcgatgATCAATAgaaCCTGGCTCCC |
| 3s-505STar-mi | SEQ ID NO. 248: | ctagGGGAGCCAGGTTCTATTGATCA |
| | | |
| hsa-mir-502 | | |
| | | |
| 5Xho-miR502 | SEQ ID NO. 249: | tatCTCGAGAATATGTGTAGGAGACTTG |
| 3BamH-miR502 | SEQ ID NO. 250: | tatGGATCCTGTCTCACTCTGGATACCTG |
| | | |
| 5x-502-5p-si | SEQ ID NO. 251: | tcgaTAGCACCCAGATAGCAAGGAT |
| 3s-502-5p-si | SEQ ID NO. 252: | ctagATCCTTGCTATCTGGGTGCTA |
| | | |
| 5x-502-5p-mi | SEQ ID NO. 253: | tcgaatGCACCCtctTAGCAAGGAT |
| 3s-502-5p-mi | SEQ ID NO. 254: | ctagATCCTTGCTAAGAGGGTGCAT |
| | | |
| 5x-502-3p-si | SEQ ID NO. 255: | tcgaTGAATCCTTGCCCAGGTGCATT |
| 3s-502-3p-si | SEQ ID NO. 256: | ctagAATGCACCTGGGCAAGGATTCA |
| | | |
| 5x-502-3p-mi | SEQ ID NO. 257: | tcgaacAATCCTTcggCAGGTGCATT |
| 3s-502-3p-mi | SEQ ID NO. 258: | ctagAATGCACCTGCCGAAGGATTGT |
| | | |
| miR-502-5p probe | SEQ ID NO. 259: | TAGCACCCAGATAGCAAGGAT |
| miR-502-3p probe | SEQ ID NO. 260: | AATCCTTGCCCAGGTGCATTGCATT |
| | | |
| hsa-mir-188 | | |
| | | |
| 5Xho-miR188 | SEQ ID NO. 261: | tatCTCGAGCTGCCCACTTGCACCCCCCAGGCC |
| 3BamH-miR188 | SEQ ID NO. 262: | tatGGATCCCACCACATGGGTGTGTGTTTTTCT |
| | | |
| 5x-188-5p-si | SEQ ID NO. 263: | tcgaCCCTCCACCATGCAAGGGATG |
| 3s-188-5p-si | SEQ ID NO. 264: | ctagCATCCCTTGCATGGTGGAGGG |
| | | |
| 5x-188-5p-mi | SEQ ID NO. 265: | tcgaggCTCCACgtaGCAAGGGATG |
| 3s-188-5p-mi | SEQ ID NO. 266: | ctagCATCCCTTGCTACGTGGAGCC |
| | | |
| 5x-188-3p-si | SEQ ID NO. 267: | tcgaTGCAAACCCTGCATGTGGGAG |

Figure 24 (continued)

| | | |
|---|---|---|
| 3s-188-3p-si | SEQ ID NO. 268: | ctagCTCCCACATGCAGGGTTTGCA |
| | | |
| 5x-188-3p-mi | SEQ ID NO. 269: | tcgaacCAAACCgacCATGTGGGAG |
| 3s-188-3p-mi | SEQ ID NO. 270: | ctagCTCCCACATGGTCGGTTTGGT |
| | | |
| 5x-188-3pm-si | SEQ ID NO. 271: | tcgaTGCAAACCCTGCATATGGGAG |
| 3s-188-3pm-si | SEQ ID NO. 272: | ctagCTCCCATATGCAGGGTTTGCA |
| | | |
| 5x-188-3pm-mi | SEQ ID NO. 273: | tcgaacCAAACCgacCATATGGGAG |
| 3s-188-3pm-mi | SEQ ID NO. 274: | ctagCTCCCATATGGTCGGTTTGGT |
| | | |
| hsa-mir-325 | | |
| | | |
| 5Xho-miR325 | SEQ ID NO. 275: | tatCTCGAGGTTCTGTGAGAAAAAGTTGCTTAA |
| 3BamH-miR-325 | SEQ ID NO. 276: | tatGGATCCTAACCACCACTAGGCCTAAGTACC |
| | | |
| Oligo for mutagensis | | |
| 5-miR325-mut | SEQ ID NO. 277: | CATAATTTGTTTATTaAGGACCTCCTATCAA |
| 3-miR325-mut | SEQ ID NO. 278: | TTGATAGGAGGTCCTTAATAAACAAATTATG |
| | | |
| 5Xho-miR325-L | SEQ ID NO. 279: | tatCTCGAgacagggattgtatggctta |
| 3BamH-miR-325-L | SEQ ID NO. 280: | tatGGATcctcaacacactgaaatctg |
| | | |
| 5Xho-miR325-s | SEQ ID NO. 281: | tatCTCGAGATTCAAGTCCACAGAACCA |
| 3BamH-miR-325-s | SEQ ID NO. 282: | tatGGATccTCAAAATGTAGGATGTTG |
| | | |
| 5x-325-5p-siL | SEQ ID NO. 283: | tcgaACAAACACTTACTGGACACCTACTAGGAA |
| 3s-325-5p-siL | SEQ ID NO. 284: | ctagTTCCTAGTAGGTGTCCAGTAAGTGTTTGT |
| | | |
| 5x-325-3p-siL | SEQ ID NO. 285: | tcgaTTGATAGGAGGTCCTCAATAAACAAATT |
| 3s-325-3p-siL | SEQ ID NO. 286: | ctagAATTTGTTTATTGAGGACCTCCTATCAA |
| | | |
| 5x-325-si | SEQ ID NO. 287: | tcgaACACTTACTGGACACCTACTAGG |
| 3s-325-si | SEQ ID NO. 288: | ctagCCTAGTAGGTGTCCAGTAAGTGT |
| | | |
| 5x-325-mi | SEQ ID NO. 289: | tcgatgACTTACTGctgACCTACTAGG |
| 3s-325-mi | SEQ ID NO. 290: | ctagCCTAGTAGGTCAGCAGTAAGTCA |
| | | |
| hsa-mir-510 | | |
| | | |
| 5Xho-miR510 | SEQ ID NO. 291: | tatCTCGagtcctgaaaactGCCA |
| 3BamH-miR510 | SEQ ID NO. 292: | tatGGATCCTTGCAAGTTTGTAAAGAAGG |
| | | |
| miR-510-5p probe | SEQ ID NO. 293: | GTGATTGCCACTCTCCTGAGTA |
| miR-510-3p (star) probe | SEQ ID NO. 294: | CCACTCTTAGAGGTTTCAATCA |
| | | |

Figure 24 (continued)

| | | |
|---|---|---|
| 5x-510Star-si | SEQ ID NO. 295: | tcgaCCACTCTTAGAGGTTTCAATCA |
| 3s-510Star-si | SEQ ID NO. 296: | ctagTGATTGAAACCTCTAAGAGTGG |
| | | |
| 5x-510Star-mi | SEQ ID NO. 297: | tcgaggACTCTTActcGTTTCAATCA |
| 3s-510Star-mi | SEQ ID NO. 298: | ctagTGATTGAAACgagTAAGAGTcc |
| | | |
| 5x-510Star-m-si | SEQ ID NO. 299: | tcgaCCACTCTTAGAGGTTTCAgTCA |
| 3s-510Star-m-si | SEQ ID NO. 300: | ctagTGAcTGAAACCTCTAAGAGTGG |
| | | |
| 5x-510Star-m-mi | SEQ ID NO. 301: | tcgaggACTCTTActcGTTTCAgTCA |
| 3s-510Star-m-mi | SEQ ID NO. 302: | ctagTGAcTGAAACgagTAAGAGTcc |
| | | |
| 5x-510-si | SEQ ID NO. 303: | tcgaGTGATTGCCACTCTCCTGAGTA |
| 3s-510-si | SEQ ID NO. 304: | ctagTACTCAGGAGAGTGGCAATCAC |
| | | |
| 5x-510-mi | SEQ ID NO. 305: | tcgacaGATTGCCtgaCTCCTGAGTA |
| 3s-510-mi | SEQ ID NO. 306: | ctagTACTCAGGAGTCAGGCAATCTG |
| | | |
| hsa-mir-660 | | |
| | | |
| 5Xho-660 | SEQ ID NO. 307: | tatCTCGAgcactgcttctccaggcgtg |
| 3Bam-660 | SEQ ID NO. 308: | tatGGATCCTGGGGAAGTCTAGGCACC |
| | | |
| S660-5p-si | SEQ ID NO. 309: | tcgaCAACTCCGATATGCAATGGGTA |
| N660-5p-si | SEQ ID NO. 310: | ggccTACCCATTGCATATCGGAGTTG |
| | | |
| S660-5p-si-m | SEQ ID NO. 311: | tcgaCAACTCCAATATGCAATGGGTA |
| N660-5p-si-m | SEQ ID NO. 312: | ggccTACCCATTGCATATTGGAGTTG |
| | | |
| S660-3p-si | SEQ ID NO. 313: | tcgaCCTCCTGTAATCCATGCACACAGGAGGTG |
| N660-3p-si | SEQ ID NO. 314: | ggccCACCTCCTGTGTGCATGGATTACAGGAGG |
| | | |
| S660-5p-mi | SEQ ID NO. 315: | tcgaGTACTCCGAGTCGCAATGGGTA |
| N660-5p-mi | SEQ ID NO. 316: | ggccTACCCATTGCgacTCGGAGTac |
| | | |
| 660-5p probe | SEQ ID NO. 317: | CAACTCCGATATGCAATGGGTA |
| | | |
| hsa-miR-509-3 | | |
| | | |
| 5Xho-509-2 | SEQ ID NO. 318: | tatCTCgagtggacaggactcaaagc |
| 3Bam-509-2 | SEQ ID NO. 319: | tatGGATCCACGTGTCTGGTGGTCAGGC |
| | | |
| S509-5p-si | SEQ ID NO. 320: | tcgaTGATTGCCACTGTCTGCAGTA |
| N509-5p-si | SEQ ID NO. 321: | ggccTACTGCAGACAGTGGCAATCA |
| | | |
| S509-3p-si | SEQ ID NO. 322: | tcgaCTACCCACAGACGTACCAATCA |

Figure 24 (continued)

| | | |
|---|---|---|
| N509-3p-si | SEQ ID NO. 323: | ggccTGATTGGTACGTCTGTGGGTAG |
| | | |
| 5Xho-509-3 | SEQ ID NO. 324: | tatCTCGAGtgggagtggacagcactcaa |
| 3Bam-509-3 | SEQ ID NO. 325: | tatGGATCCAAATTCCTAGACCATGTGTC |
| | | |
| 5S-509-3-5p-si | SEQ ID NO. 326: | tcgaCATGATTGCCACGTCTGCAGTA |
| 3N-509-3-5p-si | SEQ ID NO. 327: | ggccTACTGCAGACGTGGCAATCATG |
| | | |
| 5S-509-3CT-3p-si | SEQ ID NO. 328: | tcgaCTACCCACAAACGTACCAATCA |
| 3N-509-3CT-3p-si | SEQ ID NO. 329: | ggccTGATTGGTACGTTTGTGGGTAG |
| | | |
| 5S-509-3CG-5p-si | SEQ ID NO. 330: | tcgaCATCATTGCCACGTCTGCAGTA |
| 3N-509-3CG-5p-si | SEQ ID NO. 331: | ggccTACTGCAGACGTGGCAATGATG |
| | | |
| S509-3-5p-mi | SEQ ID NO. 332: | tcgaGTTGATTGCGTGGTCTGCAGTA |
| N509-3-5p-mi | SEQ ID NO. 333: | ggccTACTGCAGACcacGCAATCAac |
| | | |
| U2A probe | SEQ ID NO. 334: | AGAACAGATACTACACTTGA |
| | | |
| S1-27 mer siRNA | | |
| | | |
| Sense | SEQ ID NO. 335: | GCGGAGACAGCGACGAAGAGCUCAUCA |
| Antisense | SEQ ID NO. 336: | UGAUGAGCUCUUCGUCGCUGUCUCCGC |
| Probe ( Detect antisense) | SEQ ID NO. 337: | GCGGAGACAGCGACGAAGAGCTCATCA |

Figure 25

Table 8. List of all miRNA gene variants that were found in the control population or the patient samples.

| miRNA | Variants |
| --- | --- |
| hsa-let-7f-2 | 5p 11: G > A |
| hsa-miR-18b | Stem-loop 32: A > G |
| hsa-miR-188 | 3p 60: C > T |
| hsa-miR-224 | Stem-loop 41: G > A |
| hsa-miR-325 | Stem-loop 66/3p 6: G > A |
| hsa-miR-421 | Stem-loop 73: G > A |
| hsa-miR-421 | 4 nt downstream of the 3' end of the stem-loop: G > A |
| hsa-miR-450a-2 | 5p 4: T > C |
| has-miR-502 | Stem-loop 13: C > G |
| has-miR-505 | Stem-loop 8: C>T |
| hsa-miR-509-1 | Stem-loop 54: ins TGA |
| hsa-miR-509-2 | Stem-loop 9: G > T |
| hsa-miR-509-2 | 5p 11: 'A' Deletion |
| hsa-miR-509-3 | 5p 22: G > A |
| hsa-miR-509-3 | 5p 19: C > G |
| hsa-miR-509-3 | 3p 13: C > T |
| hsa-miR-510 | Stem-loop 48/3p 4: T>C |
| hsa-miR-510 | Stem-loop 6: G > A |
| hsa-miR-660 | 5p 15: C > T |
| hsa-miR-888 | Stem-loop 77: A > C |
| hsa-miR-890 | Stem-loop 66: G > C |
| hsa-miR-891b | Stem-loop 35: C > G |
| hsa-miR-892b | 3p 15: T > C |
| hsa-miR-934 | 5p 1: T > G |

MICRO RNAS AND THEIR METHODS OF USE FOR THE TREATMENT AND DIAGNOSIS OF SCHIZOPHRENIA AND SCHIZOPHRENIA SPECTRUM DISORDERS

PRIORITY CLAIM

This application claims the benefit of U.S. Provisional Application Ser. No. 61/060,892, filed Jun. 12, 2008, which is incorporated herein by reference.

GOVERNMENT INTEREST

The present invention was made with government support under National Institutes of Health grant numbers A129329 and HL07470. The government has certain rights in the present invention.

BACKGROUND

The present invention relates generally to neurological and psychiatric diseases diagnosed by and/or caused in whole or in part by microRNAs and, more specifically, to the use of individual microRNAs for the diagnosis and treatment of schizophrenia.

Schizophrenia is a chronic, severe and disabling brain disease. Approximately one percent of the population develops schizophrenia during their lifetime—more than two million Americans suffer from the illness in a given year. Schizophrenia typically presents in early adulthood or late adolescence. The illness is characterized by positive symptoms (delusions or hallucinations), negative symptoms (blunted emotions and lack of interest) and disorganized symptoms (confused thinking and speech or disorganized behavior and perception). Additionally, cognitive deficits are also frequently observed, particularly in elderly schizophrenia patients. For some patients, the disorder is life-long, while others may have periodic episodes of psychosis. Men have an earlier age of onset than women, and also tend to experience a more serious form of the illness with more negative symptoms, poorer chances of a full recovery, and a generally worse outcome [Jablensky, 2000]. Systematic reviews show that schizophrenia is 1.4 times more likely to occur in men than in women.

MicroRNAs (miRNAs) are a large family of small, non-coding RNAs that negatively regulate gene expression at the post-transcriptional level [Ambros, 2003; Lai, 2003; Bartel, 2004]. In animals, miRNAs bind to complementary sites in target mRNAs 3' untranslated regions (UTRs) to create imperfectly paired RNA heteroduplexes that inhibit translation of the target RNAs. Many microRNAs are conserved in sequence and function between distantly related organisms.

miRNAs regulate various biological functions including developmental processes, developmental timing, cell proliferation, neuronal gene expression and cell fate [Klein et al., 2005], apoptosis [reviewed in [Mattick and Makunin, 2005; Croce and Calin, 2005], tissue growth, viral pathogenesis, brain morphogenesis [Giraldez et al., 2005], muscle differentiation [Naguibneva et al., 2006], stem cell division [Hatfield et al., 2005] and progression of human diseases [Ambros, 2003; Palatnik et al., 2003]. Condition-specific, time-specific, and individual-specific levels of gene expression may be due to the interactions of different miRNAs accounting for more accurate genetic expression of various traits [Ying and Lin, 2004].

The large number of miRNA genes, the diverse expression patterns and the abundance of potential miRNA targets suggest that miRNAs may be a significant but unrecognized source of human genetic disease, including neuropsychiatric disorders. A sequence variant in the binding site for the miRNA miR-189 in the SLITRK1 mRNA has been shown to be associated with Tourette's syndrome [Abelson et al., 2005]. In addition, components required for miRNA processing and/or function have also been implicated in fragile X mental retardation [Jin et al., 2004], DiGeorge syndrome [Landthaler et al., 2004] and cancer [Karube et al., 2005], pointing to the wide ranging involvement of miRNAs in disease.

A number of animal models have been developed for schizophrenia, utilizing both non-primate (rat) and primate (monkey) animals. In one commonly used animal model of schizophrenia, phencyclidene (PCP) is chronically administered to the animal subjects, resulting in dysfunctions similar to those seen in schizophrenic humans (Jentsch et al., 1997, Science 277:953 955; Piercey et al., 1988, Life Sci. 43(4):375 385).

The causes of schizophrenia are essentially unknown. Although it is believed to have a genetic component, environmental factors appear to influence the onset and severity of the disease. Neuropathological changes in schizophrenics may include enlargement of the lateral ventricles, cavities in the brain which are part of the cerebrospinal fluid system. Sometimes, there is a decrease in overall brain mass. Several different theories have been developed regarding the etiology of schizophrenia, including the dopaminergic, glutamatergic, and cholinergic theories of schizophrenia. The dopamine hypothesis posits that positive symptoms result from excess function of the neurotransmitter dopamine in the mesolimbic area of the brain. This hypothesis is based largely on indirect, pharmacological evidence that (1) dopamine-antagonizing drugs are effective antipsychotic agents; (2) dopamine-mimicking drug exacerbate schizophrenic symptoms and (3) certain symptoms of acute paranoid schizophrenia can be elicited in non-schizophrenics by amphetamine, a drug that activates dopamine systems. However, negative symptoms have been associated with regionally localized dopamine deficits in the prefrontal cortex. Thus, there is a need for a more effective diagnosis and treatment of this disease. Additionally, there is a need for an earlier detection method for schizophrenia, such as prior to the presentation or onset of noticeable symptoms. The present invention satisfies this need and provides related advantages as well.

SUMMARY

In accordance with one embodiment, there is provided a system and method for diagnosing and determining the susceptibility to schizophrenia.

In another embodiment, a method for determining the susceptibility to schizophrenia comprises obtaining a nucleic acid containing sample from a patient and detecting mutant miRNA alleles indicating schizophrenia.

In another embodiment, a method for diagnosing or identifying schizophrenia comprises obtaining a nucleic acid containing sample from a patient and detecting mutant miRNA alleles indicating schizophrenia.

A further embodiment includes a method for diagnosing schizophrenia which comprises determining the magnitude of expression of a miRNA gene or allele selected from the group consisting of those disclosed in Table 1 in a sample and comparing the magnitude of expression to a baseline magnitude of expression of the gene or allele in persons without schizophrenia, wherein elevated or depressed levels of the gene or allele (as compared to the baseline magnitude) indicate the presence of schizophrenia. This diagnostic assay may be performed examining one or a combination of more than one miRNA gene or allele associated with schizophrenia.

In another embodiment, a method for diagnosing schizophrenia comprises obtaining a nucleic acid containing sample from a patient and detecting one or more variant miRNA alleles.

Another aspect is a functional screen for testing new variants for likely contribution to schizophrenia. Variants in nucleic acid, such as in miRNA, include but are not limited to point mutations, deletions, insertions, and translocations.

In another embodiment, schizophrenia is treated or prevented by modifying the miRNA of a mammal affected or potentially affected by schizophrenia or a schizophrenia spectrum disorder using gene therapy techniques.

In another embodiment, schizophrenia is treated or prevented by administering agents to antagonize the function of the RNA, and particularly miRNA genes or alleles if such genes or alleles are upregulated, or to agonize the function of the miRNA genes or alleles if such genes or alleles are downregulated, which miRNA genes or alleles contribute to or cause schizophrenia.

Such miRNA genes or alleles referenced in these embodiments include let-7f-2, mir-18b, mir-505, mir-502, mir-188, mir-325, mir-660, mir-509-3, mir-510, mir-421, mir-934, and mir-450a-2

BRIEF DESCRIPTION OF THE DRAWINGS

FIG. 2A-I shows stem-loop sequences of miRNA and its variants that are modeled after miRBase. FIG. 2A shows SEQ ID NOS: 1-4; FIG. 2B shows SEQ ID NOS: 5-9; FIG. 2C shows SEQ ID NOS: 10-14; FIG. 2D show SEQ ID NOS: 15-19; FIG. 2E shows SEQ ID NOS: 20-24; FIG. 2F shows SEQ ID NOS: 25-29; FIG. 2G shows SEQ ID NOS: 30-34; FIG. 2H shows SEQ ID NOS: 35-39; and FIG. 2I shows SEQ ID NOS: 40-43.

FIG. 13b is a stem-loop sequence of SEQ ID NO: 96.

FIG. 17 (Table 1a) represents the results from an exemplary analysis of ultra-rare miRNA cohort-specific variants.

FIG. 18 (Table 1b) represents the results from an exemplary analysis of miRNA cohort-specific sequence variants in a gene pool analysis.

FIG. 19 (Table 2) lists exemplary miRNA primers useful in identifying X chromosome variants (SEQ ID NOS: 97-215).

FIG. 20 (Table 3) lists variants identified in cases and controls.

FIG. 21 (Table 4) lists variants with 509-2.

FIG. 22 (Table 5) lists variants without 509-2.

FIG. 23 (Table 6) lists target genes of miRNAs having ultra-rare cohort-specific variants.

FIG. 24 (Table 7) lists oligonucleotides useful for cloning pri-miRNA and probes for northern blots (SEQ ID NOS: 216-337).

FIG. 25 (Table 8) lists all the miRNA gene variants that were found in the control population or the patient samples.

DETAILED DESCRIPTION

Figure 1:
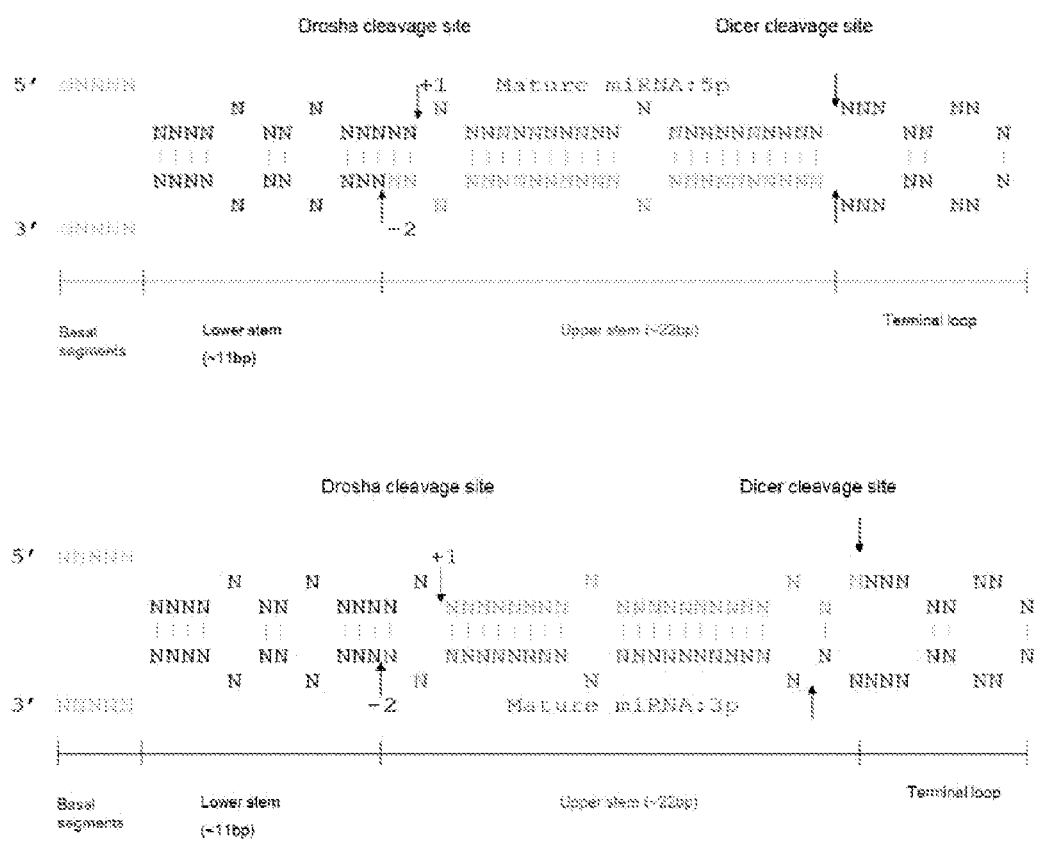
FIG. 1 shows the generation of 5p and 3p mature miRNA. This diagram was modeled after Han et al.

The present invention relates to the involvement of microRNAs (miRNAs) in development, onset and expression of symptoms associated with schizophrenia and using the understanding of such miRNA expression and activity to diagnose and treat schizophrenia or to diagnose risk of developing schizophrenia and the development of functional assays to assist the search for schizophrenia therapies.

A first aspect is a method of diagnosing schizophrenia or a schizophrenia spectrum disorder in an individual by determining the presence of a variant of a miRNA gene or allele. The miRNA may be any miRNA known or found to affect or influence schizophrenia and such activity may be determined via the functional assay described herein, which was used to determine the function of miRNAs disclosed here, or by another method that allows determination of the function of miRNA as it relates to schizophrenia. The miRNAs may be one or a combination of more than one of the following: miRNA alleles consisting of let-7f-2, mir-18b, mir-505, mir-502, mir-188, mir-325, mir-660, mir-509-3, mir-510, mir-421, mir-934, and mir-450a-2.

Generally, the method, which can be used to either determine an increased risk for schizophrenia or propensity thereto in a subject or to diagnose schizophrenia existing in a subject, comprising the steps of analyzing the miRNA in a sample obtained from the subject and determining the presence of a variant of the miRNA wherein the presence of said variant is indicative of an increased risk for developing schizophrenia or propensity thereto in the subject. Certain variants that the present invention has determined influence on schizophrenia are let-7f-2, mir-18b, mir-505, mir-502, mir-188, mir-325, mir-660, mir-509-3, mir-510, mir-421, mir-934, and mir-450a-2. The biological samples may be any sample from a subject containing mRNA, including blood, serum, plasma, saliva, urine, or tissue samples. The mRNA is isolated using any method, including the method using RNA STAT-60 described herein. The presence of RNA may be determined via any reliable method, including the use of Northern blots.

The term "miRNA" includes miRNA molecules, variants, and analogs thereof, miRNA precursor molecules, and DNA molecules encoding miRNA or miRNA precursor molecules.

Further, therapeutic applications of the miRNA described herein may be used as modulators or targets of schizophrenia and related spectrum disorders. In general, the nucleic acid molecules may be used as a modulator of the expression of genes which are at least partially complementary to said nucleic acid and are sufficient to agonize or antagonize the activity as desired. miRNA may be used as raw materials for the manufacture of sequence-modified miRNA molecules to adjust target specificity or target binding efficacy. miRNA may also be used in an attempt to alter a differentiated cell line back into a stem cell or another cell type to avoid the onset or symptoms of schizophrenia. For therapeutic applications, miRNA may be administered alone or as part of a composition, which comprises the miRNA (or different miRNAs) and a pharmaceutically acceptable carrier. The therapeutic methods may be carried out by known methods, wherein a nucleic acid is introduced into a desired target cell in vitro or in vivo using gene transfer techniques include calcium phosphate, DEAE-dextran, electroporation, microinjection, viral vectors, and commercial liposomes. The composition may be in any suitable form such as an injectable solution, a cream, ointment, tablet, suspension, or pill and may be administered in any therapeutically effective manner, such as parenterally, intravenously, orally, or nasally.

Methods of screening and tests for the bioactivity of a miRNA are disclosed. The test determines altered functionality of a miRNA gene or allele variant. The test uses functionality activity comparisons. In one embodiment, polyadenylated RNA polymerase II transcripts, termed "primary miRNAs" (pri-miRNA) is and variant or putative variant miRNA is isolated. Then, the pri-miRNA and variant miRNA are co-transfected with an si target and an mi target. Preferably, each target has its own reporter. Then, the functionality of the variant is determined using miRNA and siRNA assays. Changes in the level of expected repression of the si and mi reporters (either reduced or enhanced repression) in transient transfection assays indicates altered functionality of the miRNA gene or allele variant. The variants may be the result of one or more of a SNP, point mutation, deletion, insertion, frameshift, or translocation. The screen may be used to test whether the miRNA variant indicates predisposition to or incidence of schizophrenia.

For the methods of diagnosing, assessing susceptibility, and/or treating schizophrenia involving the identification and/or observation of microRNAs (miRNA) and preferably, variant miRNA are provided and identified as follows: Individual microRNAs (miRNAs) effect moderate down-regulation of gene expression, typically by two-to four-fold. Micro RNAs alleles associated with schizophrenia and schizophrenia spectrum disorders were identified. The miRNA genes were amplified in patients and controls. Ultra-rare variants in the precursor or mature miRNA were identified in distinct miRNA genes in males with schizophrenia and one ultra-rare variant was identified in a control sample (8/193 versus 1/191, p=0.019). These variants were not found in an additional 7,197 control X-chromosomes. Functional analyses of ectopically expressed copies of the variant miRNA precursors demonstrate loss of function, gain of function and altered expression levels. The present invention also provides methods for selecting a preferred therapy for a particular subject or group of subjects or individuals at risk for or suffering from schizophrenia or psychosis by use of miRNAs.

miRNA genes are scattered among all the chromosomes in humans except for the Y chromosome. They primarily derive from intronic or exonic capped, polyadenylated RNA polymerase II transcripts, termed "primary miRNAs" (primiRNA). It is estimated that approximately one-third of human protein coding genes are post-transcriptionally controlled by miRNAs. The mature miRNAs are used to guide miRNA-induced silencing complex ("RISC") to the complementary sequences in the 3'UTR of targeted transcripts. The result is site specific mRNA cleavage when the pairing is nearly complete (mostly in plants, rare in animals) or translational inhibition when imperfect base-pairing occurs (mostly in animals).

Translational suppression and mRNA degradation, modes by which mammalian miRNAs regulate gene expression, do not require complete complementarity between the miRNA and target. All that is required to reduce protein levels of the target is Watson-Crick base pairing between seven consecutive nucleotides in the target mRNAs 3' UTR and nucleotides 2-7 or 2-8 (the "seed sequence") at the miRNA's 5' end. The critical role played by the "seed sequence" in the majority of miRNA/mRNA interactions implies that a single nucleotide change in the seed sequence, or shift of the processing sites during biogenesis of the miRNA/miRNA* duplex could result in a novel miRNA with alternated target-spectra. Therefore, both the 5'end of the mature miRNA that is generated from the 5' arm of the pre-miRNA (5p) by Drosha, and the 5' end of the mature miRNA that is produced by Dicer from the 3' arm of the premiRNA (3p), will be under strong selective pressure to be highly conserved. (Drosha is an RNase III enzyme that initiates miRNA processing. Dicer is an RNase III endoribonuclease that cleaves miRNA into small interfering RNA (siRNA)). The sequence preceding the 5' end or trailing the 3' end of the pre-miRNAs form an ~11 bp long imperfect stem which is recognized by DGCR-8 as part the required structure for Drosha cutting. For most miRNAs/target combinations, a single nucleotide change in the seed sequence or any base shift during the Drosha/DGCR8 or Dicer/TRBP processing step can result in altered function or creation of a novel miRNA. The terminal loop is also important for Dicer/TRBP complex binding as well as for other protein binding. Sequences outside the seed in the mature miRNA sequence can also impact the strength of inhibition as well as the spectra of targeted transcripts.

Mature miRNAs are generated by a two-step processing mechanism (FIG. 1). PrimiRNAs are first processed to "hairpin-like" partially duplexed precursor miRNAs (premiRNA) in the nucleus. Aside from a small group of pre-miRNAs that are generated through mRNA splicing/debranching machinery termed the "miRtron pathway", most pre-miRNAs are processed from pri-miRNAs by the nuclear RNase (ribonuclease) III Drosha which partners with the RNA binding protein DGCR8 (the DiGeorge syndrome critical region gene 8). Pre-miRNAs are typically 55-80 nt in length and are exported to the cytoplasm by exportin-5/RAN-GTP. The pre-miRNAs are processed into ~21-22 nt long miRNA/miRNA* duplexes by RNase III Dicer, which partners with the RNA binding protein TRBP (TAR RNA binding protein). The production of miRNA/miRNA* duplexes is an essential step in miRNA biogenesis and precisely defines the ends of the mature miRNAs for preferential loading of the guide strand. The choice of the guide strand is dependent in part on the thermodynamic end properties of the duplex, with the least thermodynamically stable 5' end usually being chosen as the guide strand while the other strand, labeled miRNA*, is usually degraded. Most recently, the fates of the miRNA guide and miRNA* strands have been shown to be tissue dependent with both strands being functionally active under specific conditions. Argonaute-mediated loading into the processing complex can increase the bias of strand loading, and RNA binding proteins can selectively block the processing of primiRNAs.

The mature miRNAs are incorporated into a ribonucleoprotein complex, the RNA-induced silencing complex (RISC), which contains at least Dicer, TRBP and Ago2 [Hammond et al., 2000; Mourelatos et al., 2002; Hutvagner and Zamore, 2002]. In RISC, miRNAs can mediate down regulation of target gene activity by translational inhibition in animals [Zeng et al., 2002]. RISC can cleave, degrade or suppress translation of target mRNAs depending on the position and extent of the complementarity between miRNAs and target mRNAs. Given the complexity of protein interactions and the number of processing steps required to produce a functional miRNA, point mutations affecting any of these steps could dramatically impact the downstream function of these miRNAs.

The hairpin structure guided miRNA processing, the thermodynamic influences on strand loading, and the base pairing requirements for miRNA/mRNA interaction indicate that single nucleotide polymorphisms ("SNPs") in miRNA genes affect miRNA biogenesis and function. Similarly, SNPs in the miRNA target also affect miRNA function. To clarify possible confusions in terminology with respect to SNPs, the terms "miR-SNP" refers to the variation that occurs in the miRNA gene sequence, and "miR-TS-SNP" refers to SNPs that occur in the miRNA target site (TS) or binding site. Since one miRNA can have multiple targets, miR-SNPs would exhibit more profound and broader biological effects than miR-TS-SNPs.

The roles that sequences flanking the pre-miRNA play in miRNA processing has been thoroughly studied. MiR-SNPs in miR-125a and Kaposi's sarcoma-associated herpes virus encoded miR-K5 impaired miRNA processing by the Drosha/DGCR8 complex. MiR-196a2-SNP (rs11614913) in the mature miR-196a2 was associated with a significantly decreased rate of survival in individuals with non-small cell lung cancer, and an association of rs11614913 with enhanced processing of mature miR-196a. MiR-146a-SNP (rs2910164) within the pre-miR-146a sequence reduced both the amount of pre-and mature miR-146a, and affected the Drosha/DGCR8 processing step. MiR-196a2-SNP, miR-146a-SNP, miR-149-SNP (rs2292832) and miR-499-SNP (rs3746444) are each associated with increased breast cancer risk. MiR-146a-SNP was associated with papillary thyroid carcinoma, breast/ovarian cancer, and hepatocellular carcinoma. Each of the above are examples of SNPs created by changes in DNA coding sequences, but miRNAs can also be post transcriptionally modified, such as by RNA editing via ADAR. A to I edited pre-miR-151 blocks its processing by Dicer/TRBP. ADAR edited pri-miR-142 was more easily degraded by Tudor-SN. Edited miR-376a-5p within the middle of the "seed" region alters the set of targets regulated by this miRNA. A survey of RNA editing of miRNAs from ten human tissues implies RNA editing of miRNA happens quite often and it is a mechanism to increase the diversity of miRNAs and their targets.

Mutant or post transcriptionally edited miRNAs can result in alterations of processing and function. Hence, SNPs that occur in sequences downstream or upstream of the pre-miRNA, sequences in the terminal loop of premiRNA, and sequences in the miRNA and miRNA* duplexes may also play important roles in miRNA biogenesis and function (FIG. 1).

In the present experiments, X-linked miRNA genes from patients with diagnosed schizophrenia or autism were analyzed and compared with a gene pool analysis consisting of over 7,000 chromosomes from normal individuals (i.e., individuals without schizophrenia or autism). Twenty-four different point mutations have been determined in either the mature miRNA sequences or the precursor regions for sixteen different X-linked miRNA genes. The present invention addresses the effects on miRNA generation and function generated by SNPs in X-linked miRNAs.

Of the tested miRNA-SNPs, one variant results in elevated levels of the mature miRNA sequence relative to the wild type, several variants result in reduced levels of the mature miRNA sequence relative to wild type, and another variant results in the generation of a novel miRNA due to an alteration in the Drosha and/or Dicer processing sites. This latter miRNA-SNP also has an alteration the strand loading bias relative to the wild type version. A single base alteration even outside of the mature miRNA sequence can have profound consequences on miRNA generation and function.

Figure 3B:
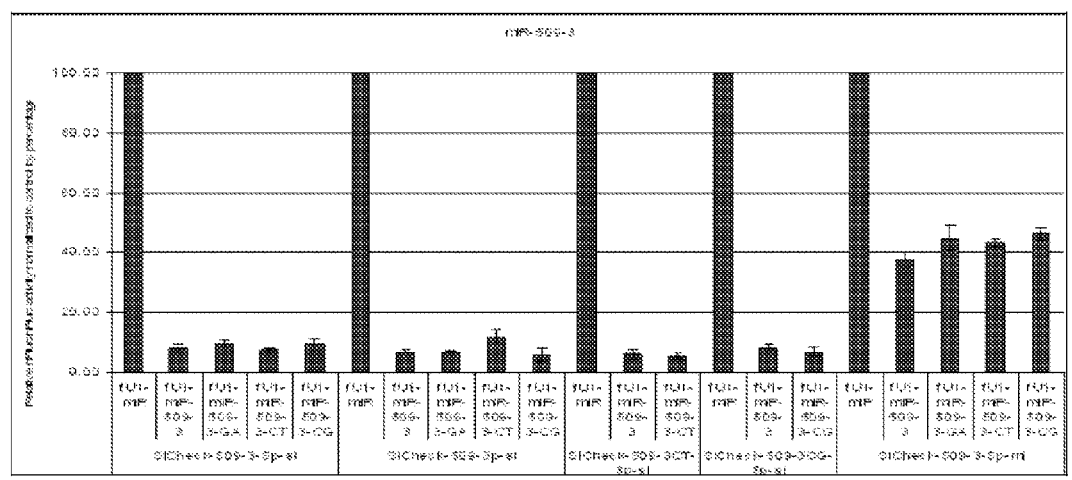
FIG. 3 shows transfection data of miR-509-3 and its single nucleotide polymorphisms (SNPs). The repression of all reporters was the same for both the WT and the Mut (FIG. 3A: SEQ ID NOS: 44-47).

Most miR-SNPs are located in clusters and some of them, such as mir-510 and miR-509, rapidly evolved in primates. Table 4 shows variants with 509-2 and Table 5 shows variants without 509-2. One clear example is the generation of miR-509-3-5p by the deletion of an 'A' from miR-509-5p, which is processed from miR-509-1 or 2 (FIG. 2; SEQ ID NOS: 1-43). There are three copies of miR-509, miR-509-1 and miR-509-2 that produce the same mature miRNAs, while miR-509-3 produces a different 5p product. Most likely, the miR-509-3-5p was created by the deletion of an 'A' from miR-509-5p. A high percentage of an ATG insertion was also observed in the 5' end of miR-509-1-3p. This insertion may affect both 5p and 3p processing. Eventually, under the selective pressure to target different mRNAs or to target with different specificities, the three copies of miR-509 may have developed into different family members with the same seed, like the let-7 family, or different miRNAs in the same cluster, like the miR-25-93-106b cluster. The miR-509 structure is more flexible, as there are no significant differences in the processing or function among three different miR-509-3 variants (FIG. 3, SEQ ID NOS: 44-47).

Many factors contribute to differences in miRNA expression profiles, including transcriptional regulation, post transcriptional miRNA processing, the stability of the pri-miRNA or pre-miRNA, and pre-miRNA export. The existence of miRNA targets may also result in miRNA stabilization because of engagement in miRISC. Different miRNA profiles are a consequence of subtle genetic changes in pre-miRNAs and their immediate flanking sequences.

Previous in silico studies from Bentwitck and Zhang show that miRNA family expansion during primate evolution may have occurred through tandem duplications. Copy number variations and high rates of gene conversion in the newly emerged miRNAs in primates may have resulted in production of novel miRNAs with more specialized functions. As a result, gene conversion may be a major mechanism in the biogenesis of miRNAs during evolution, especially in clusters of miRNAs, homologues, or miRNA families. Finally, some of the SNPs characterized by altered processing or abundance may play significant roles in disease development and progression.

The present invention is based on the novel finding that structural variants in the microRNA genes can predispose an individual to schizophrenia. In particular, microRNA mutant alleles associated with schizophrenia were identified.

Genomic sequence information of DNAs derived from patients diagnosed with schizophrenia was compared to that of large sets of normal patient samples. In certain experiments, the comparison focused on X-linked genes in male patients. From these analyses, several mutations in microRNA precursor and mature coding sequences were identified, some of which exhibit functional impairments in our cell culture based testing system. miRNA genes are transcribed by RNA polymerase II as long primary transcripts (pri-miRNA) containing stem-loop or "hairpin" structures ~60 nt in length.

The present invention identifies ultra-rare variants in the precursor or mature miRNA, each in distinct miRNA genes in males with schizophrenia and one ultra-rare variant was identified in a control (8/193 versus 1/191, p=0.019). These variants were not found in additional 7,197 control X-chromosome alleles using gene pool analyses. Functional analyses indicated that some of these variants display altered regulatory function consistent with dominant inheritance. The altered functions or defects in processing of the pre-miRNAs in the mutant alleles detected in our analyses indicate that these microRNAs may contribute to the development of schizophrenia. It is relevant to note that each microRNA can potentially regulate dozens, and perhaps even hundreds of different transcripts during development, so even subtle defects in activity can have profound effects on development of the nervous system.

Identified targets of the miRNAs in which ultra-rare variants were found are listed in Table 6. Such targets include neuregulin 1 (NGR1), Disrupted in schizophrenia 1 (DISC1) and Regulator of G-protein signaling 4 (RGS4). Defects in miRNAs altering the interactions between miRNAs and their mRNA targets thus likely contribute to schizophrenia.

To explore the role of miRNAs in schizophrenia, 59 microRNA genes on the X chromosome were analyzed in 193 males with schizophrenia spectrum disorders. The miRNA genes were amplified in patients and controls. Ultra-rare variants in the precursor or mature miRNA were identified in distinct miRNA genes in males with schizophrenia and one ultra-rare variant was identified in a control sample (8/193 versus 1/191, p=0.019). These variants were not found in an additional 7,197 control X-chromosomes. Functional analyses of ectopically expressed copies of the variant miRNA precursors demonstrate loss of function, gain of function and altered expression levels. These results provide the first statistically significant data linking microRNA gene dysfunction with schizophrenia.

EXAMPLES

Materials and Methods
Samples
All 193 male Caucasian schizophrenic patients met criteria for the disease as defined by the Diagnostic and Statistical Manual, Fourth Edition, Revised (DSM-IV-R). The majority of patients were ascertained through state mental institutions in Minnesota. The male controls were Midwest Caucasians with no known history of psychiatric illness.

PCR Amplification and Sequencing

The genomic sequence and adjacent flanking sequences of the precursors of 59 X-linked microRNA genes (miRBase 10.1, http://microrna.sanger.ac.uk/sequences/) were amplified and sequenced with the ABI model 3730 sequencer. Sequences of the primers are listed in Table 2 (SEQ ID NOS: 97-215). The nucleotide alterations were analyzed with Sequencher software™ (Gene Codes, Ann Arbor, Mich.). Mutations were confirmed by reamplifying from genomic DNA and sequencing in the opposite direction.

Gene Pool Analysis

Genomic DNA samples from 7,197 control X-chromosomes were ascertained from a Midwest population-based sample of overwhelmingly Caucasian individuals from Minnesota and a more ethnically and geographically diverse sample of hemophilia families.

The concentration of individual DNA samples was estimated by both UV spectrophotometry and agarose gel electrophoresis with diluted quantitation standards. Samples were diluted to 200 ng/μl and combined into pools of 10, 30 and 100 samples. The concentration of each sample per μl in the pool is 20 ng, 6.7 ng and 2 ng, respectively.

Allele-specific amplification assays were developed for each case or control cohort-specific variant. The specificity and selectivity of each assay were determined utilizing negative and positive controls spiked within gene pool samples.

Cell Lines and Plasmids

HEK293, Hela, NIH-3T3 cells were purchased from ATCC and maintained in high glucose (4.5 g/l) DMEM supplemented with 2 mM glutamine, 10% FBS, and 2 mM Penicillin/Streptomycin. Transfections to HEK293, NIH-3T3 and Hela cells were performed with Lipofectamine 2000 (Invitrogen) in duplicate in 24-well plate formats when cells are at 70-80% confluency.

Cell Based miRNA Processing Test

Primary miRNA expression plasmids and reporters bearing either fully complementary or seed sequence complements to the miRNAs were co-transfected into HEK293 cells. Dual-reporters (expressing both Firefly and Renilla luciferase) carrying the miRNA fully complementary sequences (si reporter) in the 3' UTR of the Renilla transcript were used to validate the ability of cloned primary miRNA expression plasmids to produce functional, mature miRNAs. Dual-reporters carrying the partially complementary sequence (mi reporter: mis-matched at position 11 to 13 and the last two nts in miRNA/mRNA duplex) of a miRNA in the Renilla 3'UTR were used to measure the strength of translational repression from the corresponding miRNA.

In order to express the pri-miRNAs, the stem-loop sequences were retrieved from miRBase 10. The stem-loop sequence, plus flanking sequences extending over 100 bases in both directions, was PCR amplified from genomic DNA. A miRNA expression vector was constructed by first cloning the human Pol II U1 promoter upstream of a multiple cloning site in the Bluescript SK plasmid to create SK-U1. Secondly, the U1 transcriptional termination sequence was cloned downstream of the MCS of SK-UL to create the fU1-miR miRNA expression vector. The primary miRNA was cloned into the Xho I and BamH1 sites of fU1-miR. miRNA variants were cloned in the same manner as the wild type miRNAs from patient DNA when available. If samples were no longer available, the QuikChange II site-directed mutagenesis kit was used to create mutants within the wildtype expression constructs. All clones were sequenced to confirm the normal miRNA and mutant forms.

For si reporters, all miRNAs and their homologous mutant target sequences were designed as fully complementary to the mature miRNA sequence. The oligos for the two strands were inserted into the psiCHECK Xho I/Spe I or XhoI/Not I digested reporter 3' UTR of the Renilla luciferase gene. All target clones were verified by sequencing. For mi reporters, all the inserted sequences in the reporter 3' UTR of the Renilla luciferase gene were designed with bulges at positions 11 to 13 and were unpaired for two nucleotides at the 3' end of the miRNA.

About $1 \times 10^4$ HEK293 cells per well in 500 microliters of growth media were plated in 24 well plates one day prior to transfection. The cells were at 70-80% confluency at the time of transfection. Each well was transfected with 5 ng reporter, 100 ng miRNA expression constructs (1:20 ratio, 1:5 ratio was used if the knockdown of the si target was >95%, then 25 ng of miRNA expression plasmid and 75 ng stuffer Bluescript SK were used) and 1 ul Lipofectomine 2000. Forty eight hours post transfection, the cells were lysed with 100 μl Passive lysis buffer (Promega) and luciferase levels were analyzed from 20 μl lysates using the Dual Luciferase reporter assay (50 μl of each substrate reagent, Promega) on a Veritas Microplate Luminometer (Turner Biosystems). Changes in expression of Renilla luciferase (target) were calculated relative to Firefly luciferase (internal control) and normalized to the miRNA expression vector control fU1-miR.

Point mutations were created with the QuikChange site-directed mutagenesis kit II (Stratagene) following the protocol included in the kit. Mutations were confirmed by sequencing.

RNA Isolation

RNA was isolated with RNA STAT-60 (Tel-Test Inc.) and 20 μg total RNA was loaded into a denaturing 12.5% SDS-PAGE gel. A DNA oligonucleotide probe complementary to the mature miRNA sequence was labeled with $\gamma\text{-}_{32}P\text{-ATP}$.

Northern Blot

Two different transfections were performed in HEK 293 cells to detect processing of expressed pri-miRNA in vivo. One transfection contained pri-miRNA expression constructs alone, while the other was co-transfected with 25/27-mer synthesized siRNA duplex. Northern blots were performed with RNAs from both transfections. U2A or U6 snoRNA were used as the RNA loading controls and co-transfected S1 siRNA was used as the transfection control. 20 μg total RNA was loaded on a 12.5% PAGE-8M urea denatured gel. Gels were transferred to a Hybond-N+ (Amersham Pharmacia biotech, positive charged) membrane. DNA probes were used for all Northern blots, and hybridizations were carried out in PerfectHyb™ Plus hybridization buffer (Sigma) for 16 hours (Table 7; SEQ ID NOS: 216-337). The blots were washed once for 10-30 minutes with 6×SSPE/0.1% SDS, followed by two washings with 6×SSC/0.1% SDS for 10-30 minutes each.

Mature miRNA Cloning

For small RNA cloning, small RNAs below 40 nt were fractionized by a flashPAGE™ Fractionator System. Small RNAs were first polyadenylated, then ligated with a 5' RNA adaptor. The 5'-adaptor-added polyadenylated small RNAs were RT-PCR amplified and the products cloned. Dot-blot hybridizations were used to identify positive clones. The positively hybridizing clones were sequenced to verify the processed mature miRNA sequences.

Dot-Blotting

Bio-Rad membranes were cut to the same size as the bottom of Petri-Dish plates. The membranes were laid on the colonies for 20 seconds or until they were wet, then lifted and washed twice in 0.5N NaOH for 5 minutes each (The plates were put back into the 37° C. incubator for 5-6 hours to preserve the colonies). Next, the membranes were washed twice in 0.5M Tris-HCl, pH 7.5 for 5 minutes each. Then, the membranes were washed twice in 6×SSC/0.1% SDS for 5 minutes each. Finally, the membranes were washed in 95% EtOH for 5 minutes and dried between two sheets of Whatman paper. All washings were performed at room temperature. Just before hybridization, membranes were soaked in 6×SSPE/0.1% SDS twice for 5 minutes each. The probe and the temperature of hybridization, and the washing condition were the same as those for the Northern blots above. The only difference was that the hybridization duration was one hour. Usually the signal is strong enough to detect after the blots are exposed to film for 5-6 hours. Positive colonies were located and plasmid DNAs were made for sequencing.

Results

Fifty-nine microRNA genes on the X chromosome were analyzed in 193 males with schizophrenia as well as 191 controls. Ultra-rare variants in the precursor or mature miRNA were identified, each in a distinct miRNA gene, in males with schizophrenia and one ultra-rare variant was identified in a control sample (8/193 versus 1/191, p=0.019, Fisher's exact test) (Table 1a). These variants were not found in an additional 7,197 control X-chromosomes using gene pool analyses.

Five cohort-specific variants, one in a patient and four in controls, were found in the gene pool analyses at a frequency greater than 0.02% (p=0.21, Fisher's exact test) (Table 1b). The schizophrenia patient's variant occurred in the mature miRNA mir509-3-5p. Of the four cohort-specific variants identified in control samples, three were found in the mature miRNAs, while one was found in the precursor.

Five common variants in miRNA precursors were found in both patients and controls with similar frequency (Table 3).

Twenty-four variants within pre-miRNAs and the immediate flanking regions were identified (Table 8). They are further characterized into four groups based on the location within the hairpin structure (FIG. 1): SNPs in the basal segment (miR-421-G/A, miR-888-A/C), SNPs in the lower stem (miR-421-G/A, miR-502-C/G, miR-505-C/T, miR-509-2-G/T, miR-510-G/A), SNPs in the miRNA/miRNA* (let-7f-2-5p-G/A, miR-188-3p-C/T, miR-325-3p-G/A, miR-450a-2-T/C, an 'A' deletion in miR-509-2-5p, miR-509-3-5p-G/A, miR-509-3-5p-C/G, miR-509-3-3p-C/T, miR -510-T/C, miR-660-5p-C/T, miR-890-3p-G/C, miR-892b-3p-T/C, miR-934-T/G), SNPs in the terminal loop (miR-18b-A/G, -G/A, a TGA insertion in the terminal loop of miR-509-1, miR-891 b-C/G).

To assess the functional consequences of the point mutations, pri-miRNAs and mutant versions of each miRNA were co-transfected with their corresponding si and mi targets (using materials and methods described above). Three or more transfections were performed, with duplicates in each transfection. At least four of the variants identified, each having a point mutation in the mature coding region, have altered function (miRNA let-7f-2, miR-188, miR-660, and miR-509-3). The novel, ultra-rare variants in the mature miRNAs were predicted to have altered target specificity.

Figure 16:
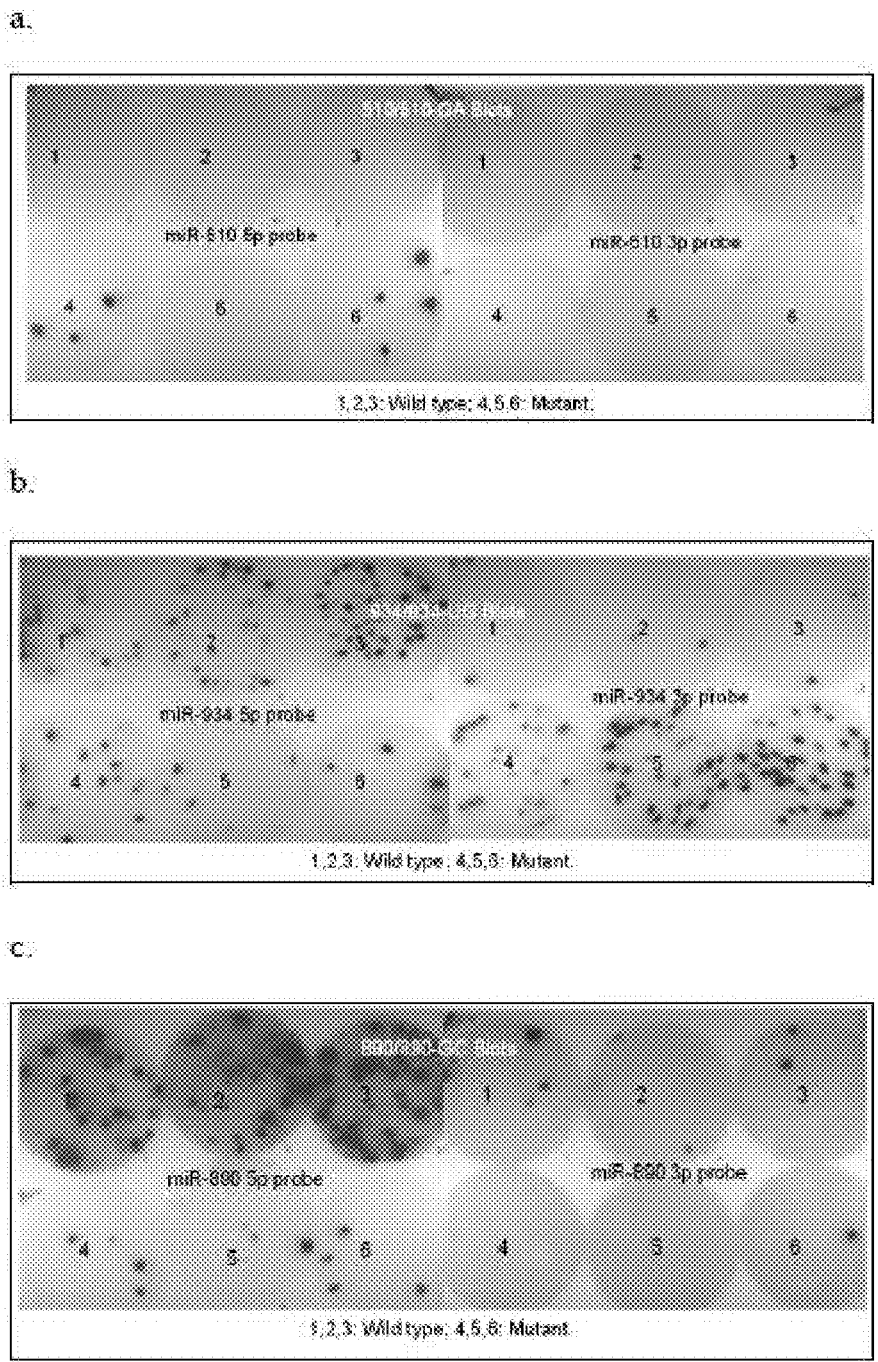
FIG. 16 shows dot blotting results. a. miR-510 verses 510-G/A. Blots 1, 2, and 3 are wild type and blots 4, 5, and 6 are mutant type. Left side blots were probed with 510-5p probe and right side blots were probed with 510-3p probe. b. miR-890 verses 890-G/C. Blots 1, 2, and 3 are wild type and blots 4, 5, and 6 are mutant type. Left side blots were probed with 890-5p probe and right side blots were probed with 890-3p probe. c. miR-934 verse 934-T/G. Blots 1, 2, and 3 are wild type and blots 4, 5, and 6 are mutant type. Left side blots were probed with 934-5p probe and right side blots were probed with 934-3p probe.

In order to evaluate the consequences of these point mutations, a novel assay was developed to monitor the processing and function of both strands of the miRNAs by employing both miRNA (seed sequence complementarity) and siRNA (fully complementary) assays. The functional assays were carried out in transient cotransfections of expressed pri-miRNA with target sequences in the 3'UTR of the Renilla luciferase encoding transcripts. At least six of the variants, miR-502-C/G (FIGS. 2 & 4), rare variant and associated with schizophrenia), miR-510-G/A (FIGS. 2 & 5), miR-510-T/C (FIGS. 2 & 6, rare variant and associated with schizophrenia), miR-890-C/G (FIGS. 2 & 8), miR-892b-T/C (FIGS. 2 & 9) and miR-934-T/G (FIGS. 2 & 10), showed reduced or enhanced repression of the 'si' and 'mi' reporters in transient transfection assays. For each of these variants, Northern blotting was performed to detect the effects of the SNP on processing of the pre and mature miRNAs. Mature miRNA cloning was performed on miR-510-G/A, miR-890-C/G and miR-934-T/G to study affect of the SNP on the maturation of the miRNAs. While all three SNPs apparently affect the miRNA processing, only the miR-934-T/G transversion also altered the Drosha or Dicer excision sites which also resulted in changing the strand bias for RISC loading relative to the wild type miRNA (FIG. 16).

Several examples in which miR-SNPs resulted in reduced processing were observed. Four of the six observed miR-SNPs, miR-502-C/G, miR-510-T/C, miR-890-C/G and miR-892b-T/C, produced less mature miRNA. While the 502-G/C SNP occurs two nts before the 5'end of 502-5p, the other three SNPs all occur in the mature 3p product.

Let-7f-2/7f-2*

Figure 12:
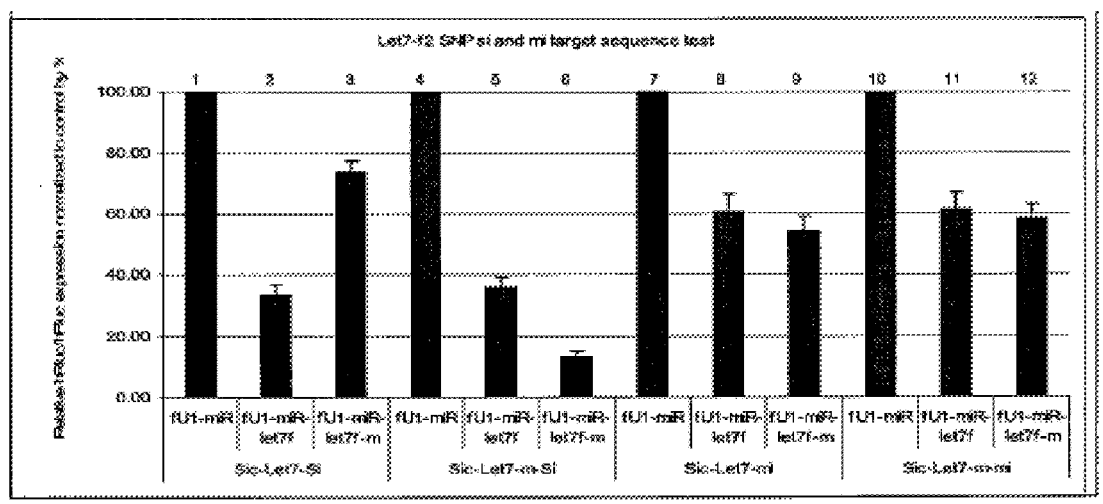
FIG. 12 shows Let7-f2 SNP si and mi target sequence test.

A single base substitution G>A was identified in the mature miRNA of let-7f-2 at position 11. This site is highly conserved from C. elegans through human. This variant is not present in 7,197 control X-chromosomes (Table 1a). To examine the possible functional consequences of this mutation, the wild type and mutant variants were tested against its corresponding si and mi target sequence. The results obtained with these analyses demonstrate that the mutant sequence can down regulate its si sequence (FIG. 12, bar #6), but its knockdown of the let-7f si sequence was dramatically reduced (FIG. 12, bar #3). On the other hand, the let-7f knockdown of the mutant si-target remained unperturbed (FIG. 12, bar #5). These results demonstrate that the mutant produces a stronger siRNA phenotype than the wild type miRNA with the cognate complementary targets. On the other hand, the variant elicits a weaker miRNA phenotype than the wild type.

miR-18b/18b*

Figure 13A:
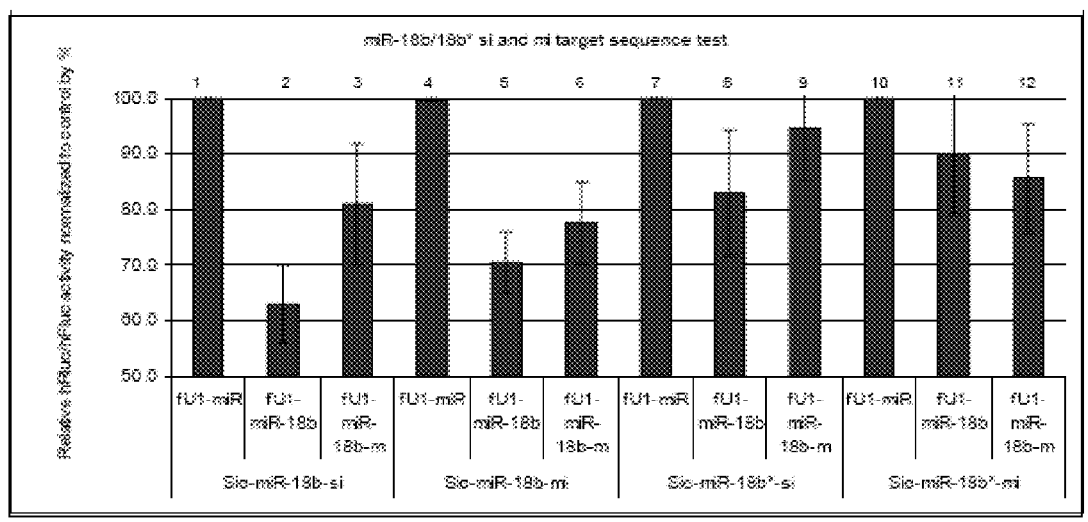
FIG. 13a shows miR-18b/18b* si and mi target sequence test.

Variant miR-18b/18b*-m has an A to G mutation at the 5th nucleotide following the last base of the mature sequence, which is also in the predicted loop structure (FIG. 13, SEQ ID NO: 96). This sequence difference may affect processing and/or stability since there is a reduction in the level of target knockdown activity when compared to wild type in the si-target (FIG. 13, bar #2 vs #3) and the mi-target assays (FIG. 13, bar #5 vs #6). In contrast, the function of the miR-18* strand does not appear to be affected by this mutation (FIG. 13 bar #7 vs 8 and Bar #9 vs 10).

miR-502-5p/3p

Figure 4A:
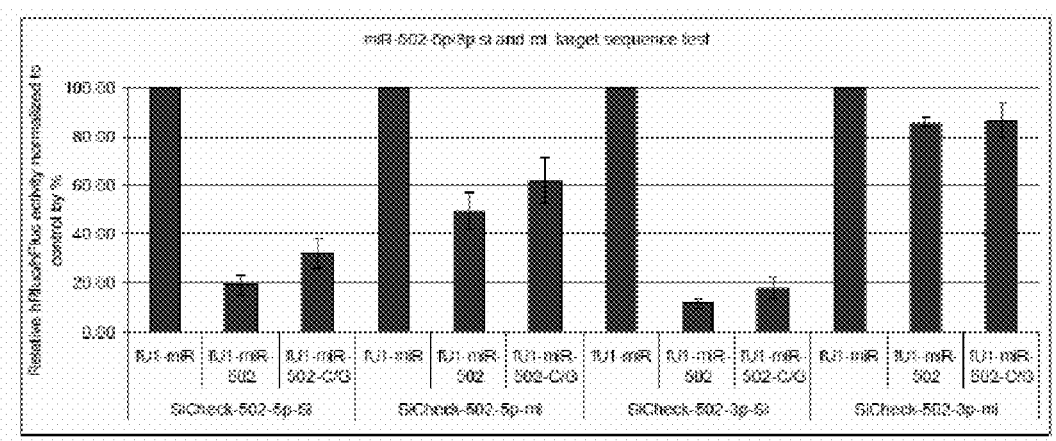
FIG. 4 shows co-transfection test results of miR-502. a. The expression of 5p-si, 5p-mi, and 3p-si reporters is reduced in the mutant whereas the expression of 3p-mi reporter is the same in the wild-type ("WT") and mutant ("Mut"). Each bar represents the average of at least three independent transfections with duplicate determinations for each construct. Error bars represent the standard deviation ("S.D."). b. Northern blot results. Top: Hybridization with a miR-502-3p probe; Middle: blot probed with a miR-502-5p probe: Bottom; hybridization with a U2 snoRNA probe and irrelevant HIV tat/rev siRNA probe. Lane 7 depicts RNAs from cells transfected with the miRNA expression vector fU1-miR; Lanes 1, 3, 5, and 6 contain RNAs from cells transfected with the WT miRNA construct; Lanes 2, 4, 8, and 9 contain samples from cells transfected with the Mut miRNA construct. U2 snoRNA was used as an RNA loading control and siRNA-1 (anti-tat/rev in HIV-1, synthetic annealed double-strand siRNA) was used as transfection control. c. Northern blot results. The left-hand panel is the RNA decade marker; the middle panel is blot probed with 502-5p; the right-hand panel is blot probed with 502-3p. For the two blots, fU1-miR-502 is run in lane 1; fU1 miR-502-C/G is run in lane 2; fU1-miR is run in lane 3. U2 and U6 are shown below. d. Nucleotide sequences of SiCheck-502-5p-si, SiCheck-502-5p-mi, SiCheck-502-3p-si, SiCheck-502-3p-mi (SEQ ID NOS: 48-55).
Figure 4B:
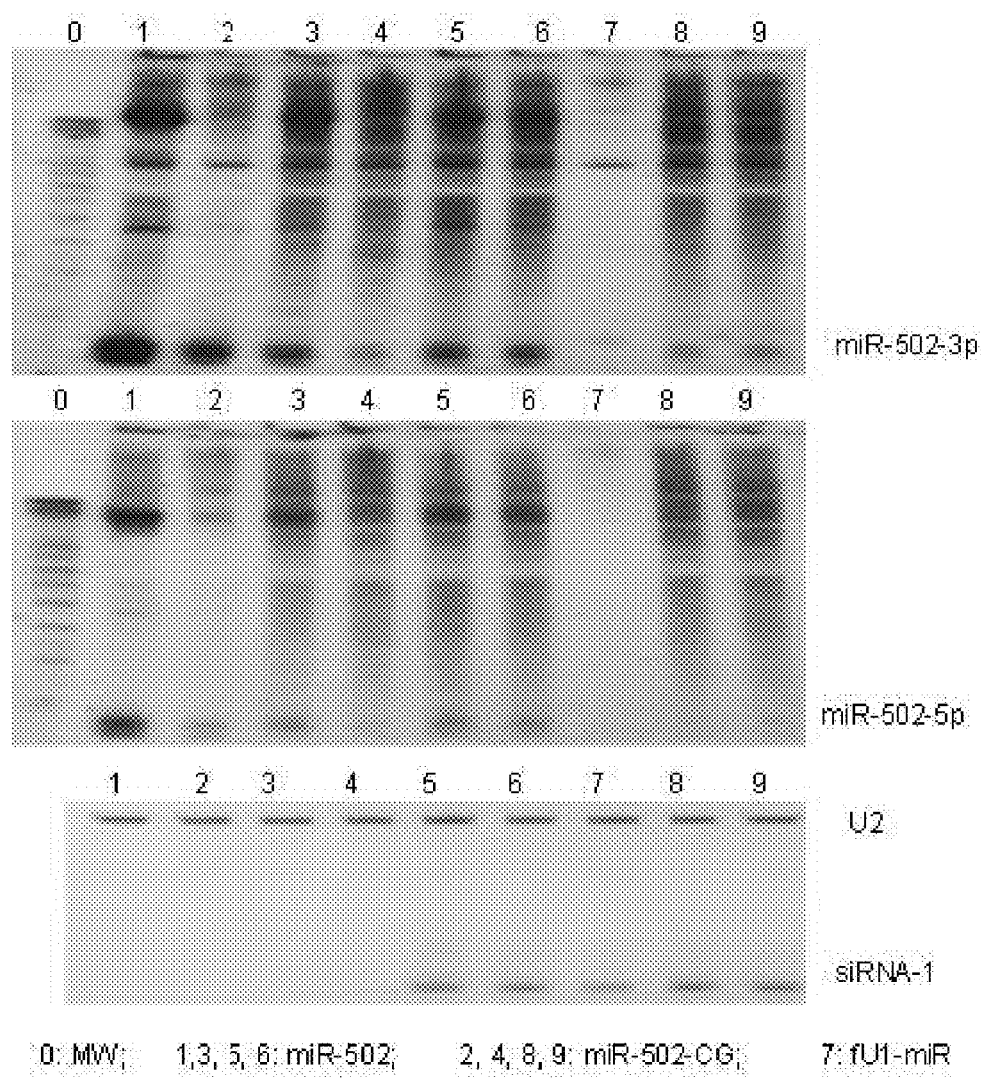
Figure 4C:
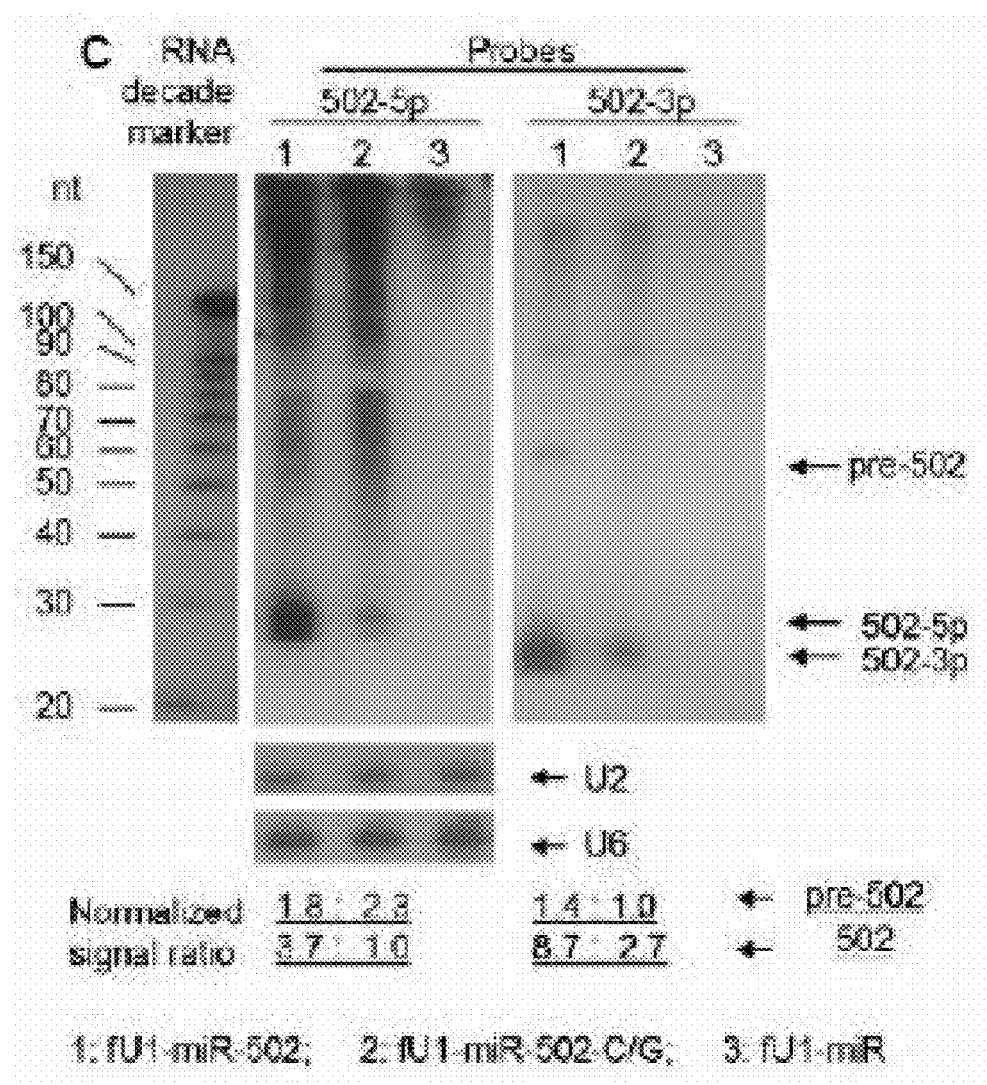

Variant miR-502-5p/3p-m has a C to G transversion at the $3^{rd}$ nucleotide ("nt") upstream of the mature miR-502-5p sequence (FIG. 4, SEQ ID NOS: 44-47). This mutation will produce a bulge which changes the structure of the stem of the precursor miRNA (FIG. 2). Most likely, this structural change will affect the site of Drosha cleavage in producing pre-miR-502, therefore, both the 5p and 3p products should be affected. Reduced target knockdowns were observed in transfection assays (FIG. 4, bar #2 vs 3, #5 vs 6 and #8 vs 9). The impaired functional activity of the variant was supported by Northern blot analyses, as the production of pre-miR-502 and mature 502-5p/3p was both reduced. (FIG. 4).

miR-188-5p/3p

Figure 14:
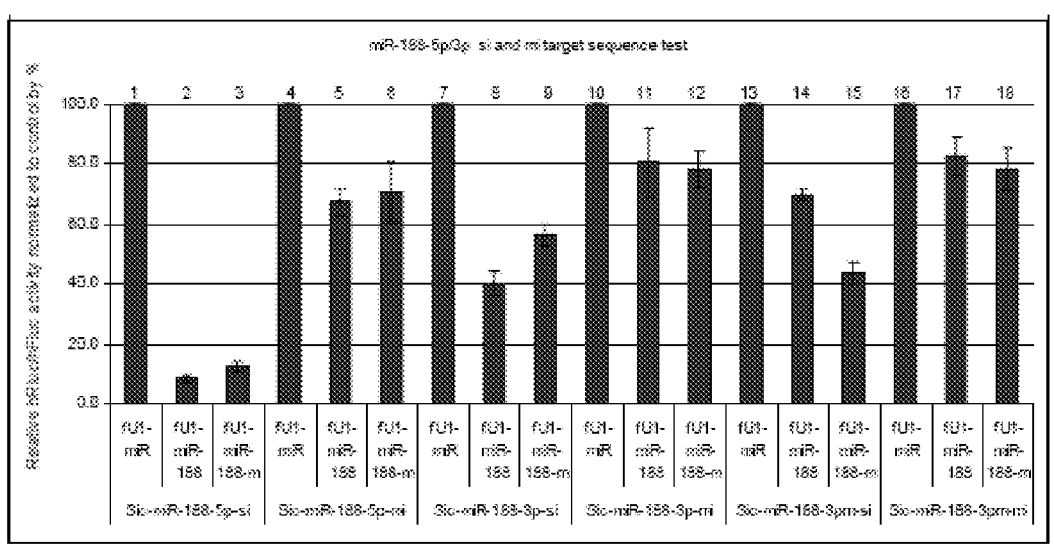
FIG. 14 shows miR-188-5p/3p si and mi target sequence test.

Variant miR-188-5p/3p-m has a C to T (U) transition at the 7th nt of the mature miR-188-3p within the seed sequence (FIG. 14). This variant results in a change of G:C to G:U pairing in the seed sequence. In our assay system, the effect of the variant is not dramatic (FIG. 14). Nevertheless, this variant will create a seed sequence where this position can pair with an A, thus potentially affecting the expression of new target sequences with a matched seed sequence.

miR-505/505*

Figure 15:
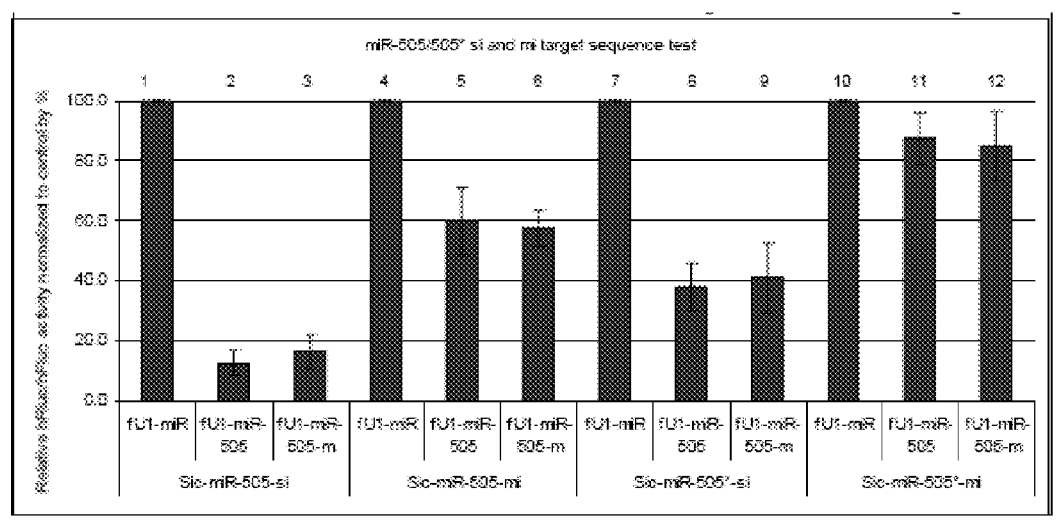
FIG. 15 shows variant miR-505/505*-m has a C to T (U) transition at the $6^{th}$ nt (relative to the 5' end of the upper strand of the mature miR-505).

Variant miR-505/505*-m has a C to T (U) transition at the $6^{th}$ nt (relative to the 5' end of the upper strand of the mature miR-505). This variant is distal to both Drosha and Dicer cleavage sites. Functional testing of this mutant (FIG. 15) revealed little difference when compared with the wild type miRNA.

miR-510

Figure 6A:
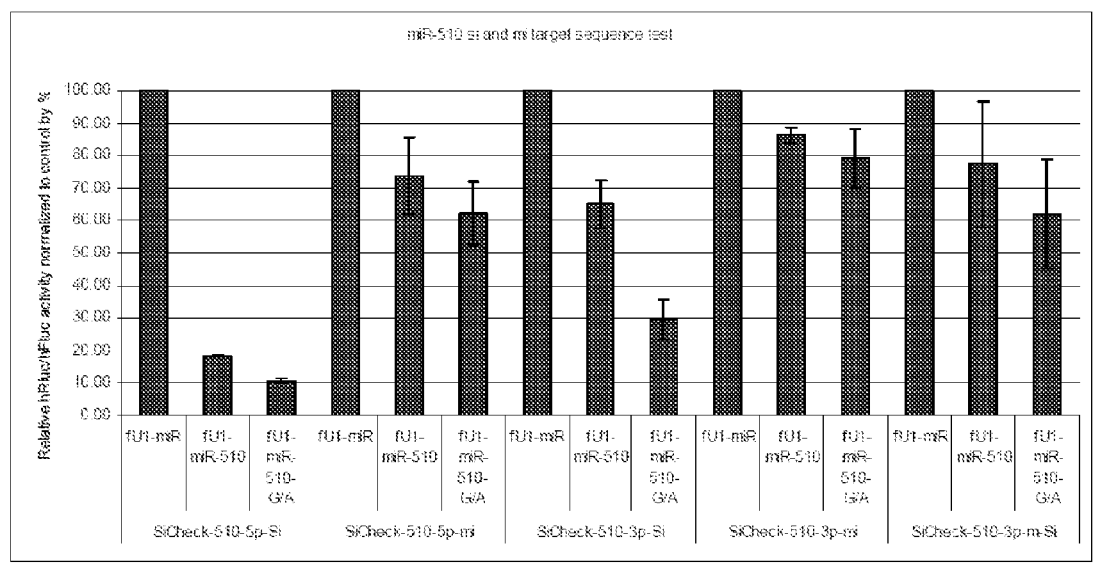
FIG. 6 variant miR-510-m has a T (U) to C transition in the seed of the predicted miR-510* (3p). Functional test of miR-510 and miR-510-T/C. a. Transfection test results. The expression of reporters for 5p-si, 5p-mi, F3p-si, and 3p-m-si (mutant form) from the mutant form are reduced. The repression for 3p-mi is approximately the same for both the WT and the mutant. Each bar represents the average of at least three independent transfections with duplicate determinations for each construct. Error bars represent the S.D. b. Nucleotide sequences of miR-510, miR-510-G/A, SiCheck-510-5p-si, SiCheck-510-5p-mi, SiCheck-510-3p-si , SiCheck-510-3p-mi (SEQ ID NOS: 56-65).

Variant miR-510-m has a T (U) to C transition in the seed of the predicted miR-510* (3p) (FIG. 6, SEQ ID NOS: 56-65). Transfection assays show processing of the miR-510-

Figure 7:
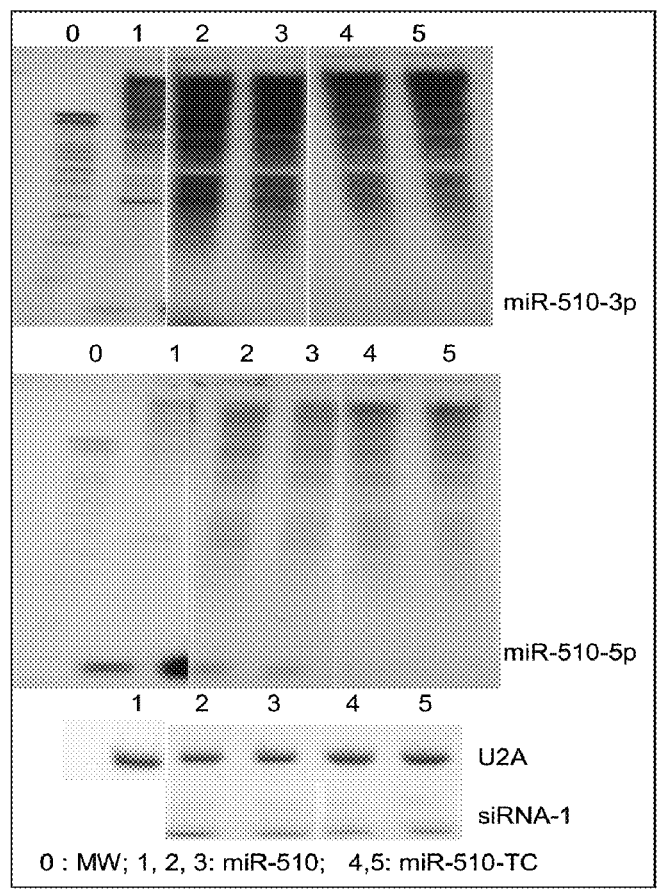
FIG. 7 shows results of a Northern blot analysis in accordance with one embodiment of the present invention. Northern blot results. Top: blot that was probed with the miR-510-3p probe; Middle: blot probed with the miR-510-5p probe; Bottom: blot probed with a U2 snoRNA (RNA sample loading control) probe and a probe that was used to detect the siRNA-1 (transfection control). Lanes 1, 2, and 3 are samples transfected with miR-510 WT; Lanes 4 and 5 were transfected with the miR-510-T/C mutant.

3p product and its ability to knockdown the corresponding si target sequence (FIG. 6, bar #8). The T (U)/C mutation produces a pre-miR-510 with much less activity for both 5p and 3p products (FIG. 6, Bar #2 vs 3, bar #5 vs 6 and bar #7 vs 8). This mutation most likely affects the structure of the pre-miR-510, as it affects the function of mature miR-510 on both strands. Northern blot analyses confirm that the production of both pre-miR510 and miR-510-5p/3p were reduced (FIG. 7).

miR-509-3

This miRNA variant has a C to T (U) transition at the 13$^{th}$ nucleotide of the mature miRNA (FIG. 3, SEQ ID NOS: 44-47). Our functional assays show that this mutation has a weak effect on the processing of the mature miRNA (FIG. 3). This base change could affect the endogenous targets down regulation as the 13$^{th}$ position is important for 3'end base pairing of miRNAs and mRNAs.

miR-660

Figure 11:
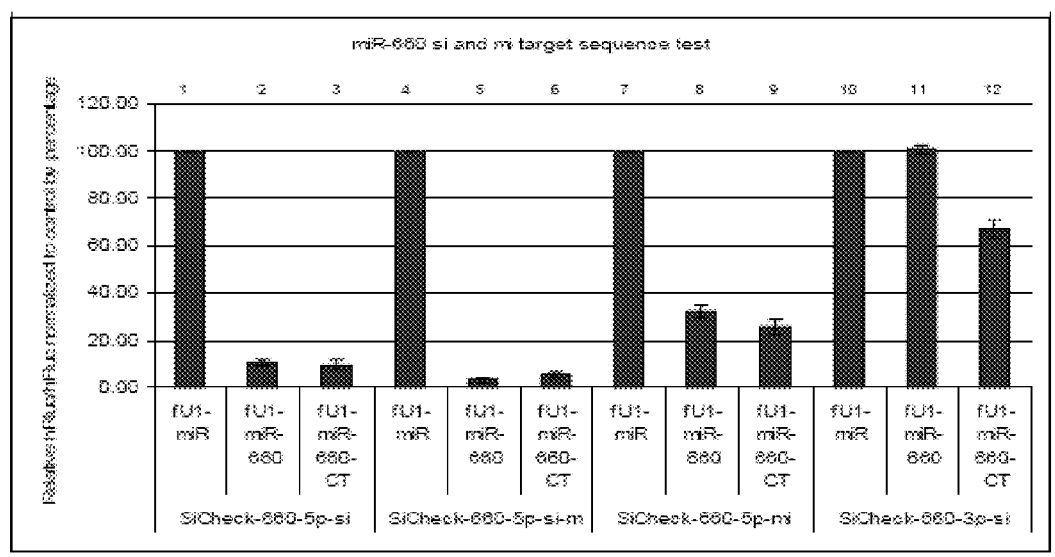
FIG. 11 shows variant miR-660 has a C to T (U) transition at the $15^{th}$ position of the mature miRNA.

Variant miR-660 has a C to T (U) transition at the 15$^{th}$ position of the mature miRNA (FIG. 11). The functional assay data shows it has little effect on the processing of the miRNA (FIG. 11). The base change could affect the natural targeting functions of the miRNA since this position affects the 3' end base pairing of miRNA/mRNA.

miR-325

Figure 8A:
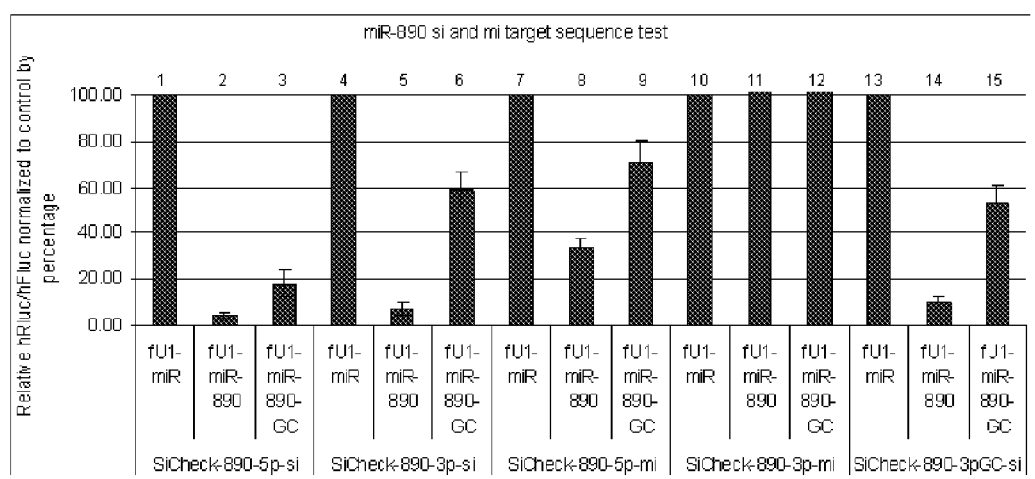
FIG. 8 shows a functional test of miR-890 and miR-890-G/C. a. Transfection test results. The expression of reporters for 5p-si, 5p-mi, 3p-si, and 3pGC-si (mutant form) from the mutant form are reduced. The expression of the 3p-mi reporter is approximately the same for both the WT and mutant. Each bar represents the average of at least three independent transfections with duplicate determinations for each construct. Error bars represent the S.D. b. Northern blot results. Under lanes 0,1, and 2 were probed with miR-890-5p, 3pGC, and 3p for samples transfected with fU1-miR or fU1-miR plus siRNA-1. Lanes 7, 8, 9, and 10 were hybridized with probes for miR-890-5p, 3pGC, and 3p. Lanes 7 and 9 were transfected with fU1-miR-890; Lanes 8 and 10 were transfected with fU1-miR-890-G/C; Lanes 9 and 10 were also co-transfected with siRNA-1. U2 and U6 snoRNAs were used as RNA loading controls and siRNA-1 was used as transfection control. c. Nucleotide sequences of miR-890, mir-890-G/C, SiCheck-890-5p-si, SiCheck-890-5p-mi, SiCheck-890-3p-si, SiCheck-890-3p-GC-si, SiCheck-890-3p-mi (SEQ ID NOS: 66-77).
Figure 8B:
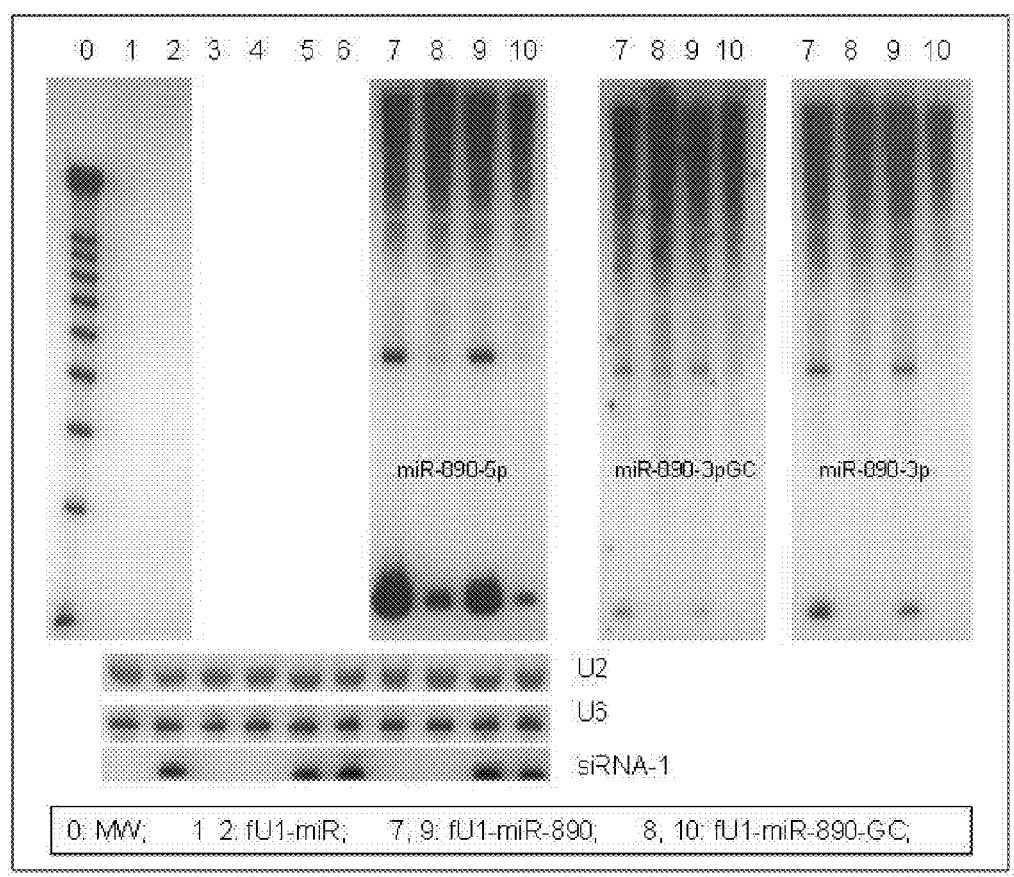

Variant miR-325-m has a G to A transition on the miR-325* strand. Interestingly, functional assays with the wild type and mutant variants did not generate knockdowns of the si target. This miRNA was originally cloned in a murine system and therefore there is no data demonstrating that the human homologue can be expressed and processed in HEK293 cells.

miR-890-C/G miR-890 3p reporter transfection assays show its ability to knockdown the corresponding 'si' target sequence. Transfection and Northern blotting data show that the C/G transversion in miR-890 affects the production of the 3p strand, but not the 5p strand (FIG. 8, SEQ ID NOS: 66-77), with the production of 3p being reduced. Because the C/G transversion may be at the Drosha cleavage site, the exact sequence of its 3p products by miRNA cloning was defined. These data show that the cutting sites for both the 5p and 3p products were not altered by this miR-SNP. The 5p and 3p mature sequences were the same for both the wild type and mutant. Dot blotting analyses (FIG. 16) also show that more clones of the miR-890 than miR-890-C/G for the 3p probe were obtained, which is consistent with the transfection and Northern blot data (FIG. 8).

miR-892b-T/C

Figure 9A:
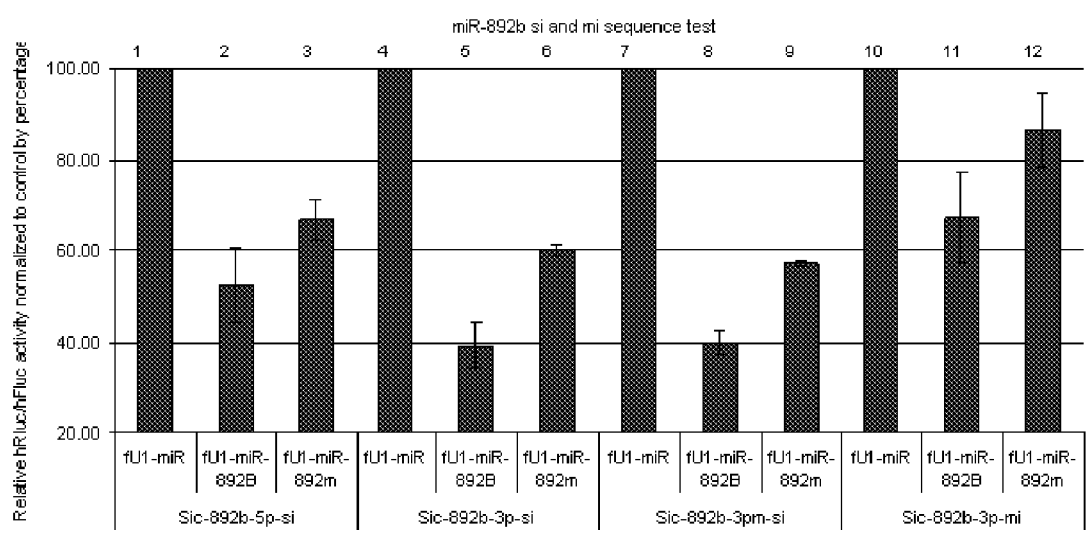
FIG. 9 shows a functional test of miR-892b and miR-892b-T/C. a. Transfection test results. The expression of reporters for 5p-si, 3p-si, 3pm-si (mutant form), and 3p-mi from the mutant form are reduced. Each bar represents the average of at least three independent transfections with duplicate determinations for each construct. Error bars represent the S.D. b. Northern blot results. Lanes 0, 1, and 2 were hybridized with probes for miR-892b-5p, 3p, and 3pTC (mutant form) using samples transfected with fU1-miR or fU1-miR plus siRNA-1. Lanes 7, 8, 9, and 10 were hybridized with probes for miR-892b-5p, 3p, and 3pTC. Lanes 7 and 9 were from cells transfected with fU1-miR-892b; Lanes 8 and 10 were from cells transfected with fU1-miR-892b-T/C; Lanes 9 and 10 were from cells also transfected with siRNA-1. U2 and U6 snoRNAs were used as RNA loading controls and siRNA-1 was used as transfection control. c. Nucleotide sequences of miR-892b, mir-892b-T/C, SiCheck-892b-5p-si, SiCheck-892b-3p-si, SiCheck-892b-3pm-si , SiCheck-892b-3p-mi (SEQ ID NOS: 78-87).
Figure 9B:
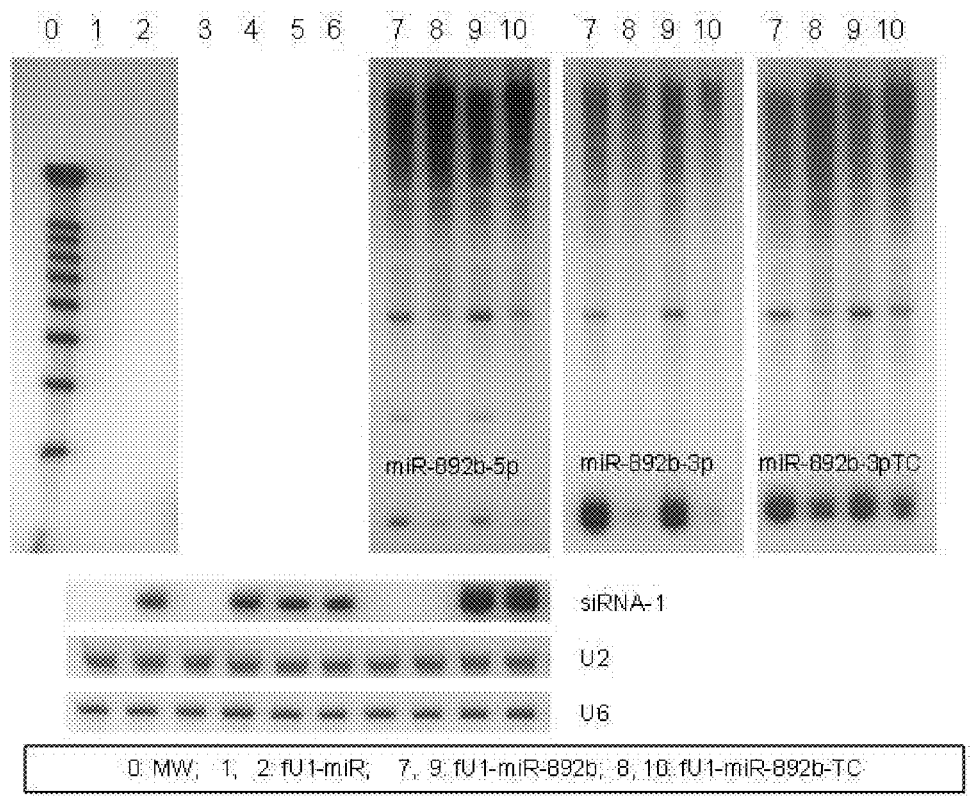

Like miR-510-T/C and miR-890-C/G, this SNP occurs in the 3p of miR-892b, but miR-892b-3p is listed in miRBase. Although there are currently no published data which support the existence of miR-892b 5p products, our 5p reporter transfection assays show its ability to knockdown the corresponding 'si' target sequence. Transfection and Northern blotting data show that the T/C transition in miR-892b affects the production of both 5p and 3p strands (FIG. 9, SEQ ID NOS: 78-87).

miR-510-G/A

Figure 5A:
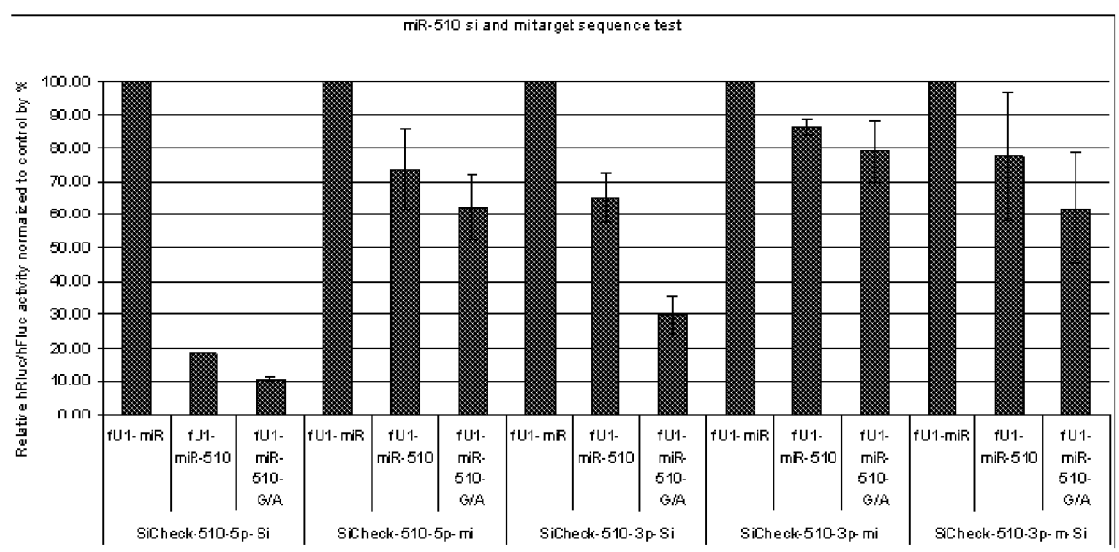
FIG. 5 shows a functional test of miR-510 and miR-510-G/A. a. Transfection test results. The expression of reporters for 5p-si, 5p-mi, 3p-si and 3p-m-si (G/A mutant form) from the mutant are all reduced. Each bar represents the average of at least three independent transfections with duplicate determinations for each construct. Error bars represent the S.D. b. Northern blot results. Top: hybridization with a miR-510-3p probe; Middle: hybridization with a miR-510-5p probe; U2 snoRNA was used as an RNA loading control. SiRNA-1 was used as a transfection control. Lane 9 is from cells transfected with fU1-miR; Lanes 1, 3, 5, and 6 are from cells transfected with fU1-miR-510; Lanes 2, 4, 7, and 8 are from cells transfected with fU1-miR-510-G/A. c. Northern blot results. The left-hand panel is a blot probed with 502-3p; the right-hand panel is a blot probed with 502-5p. For the two blots, fU1-miR is run in lane 1; fU1 miR-510 is run in lane 2; fU1-miR-G/A is run in lane; and fU1-miR-510-T/C is run in lane 4. Normalized signal ration of pre-510 and 510 is shown below.
Figure 5B:
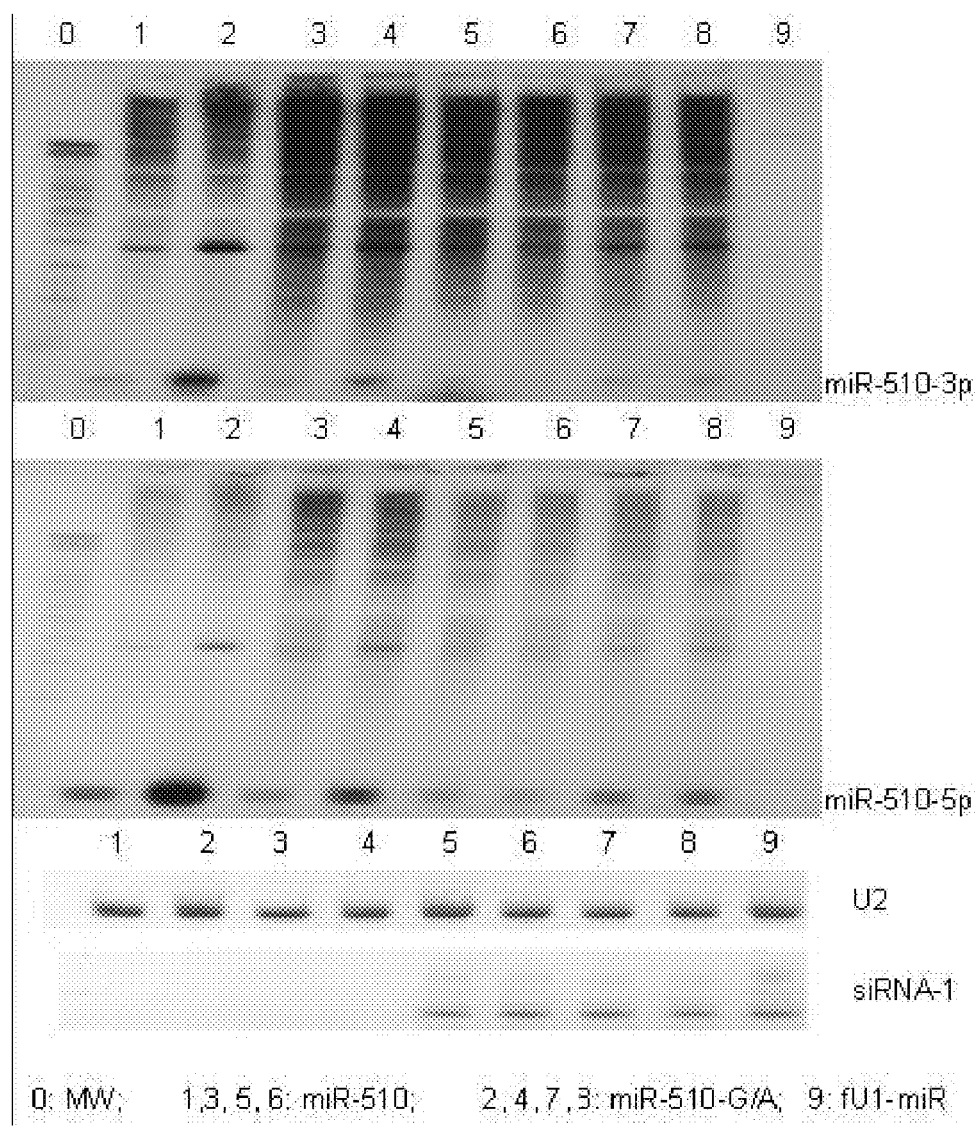
Figure 5C:
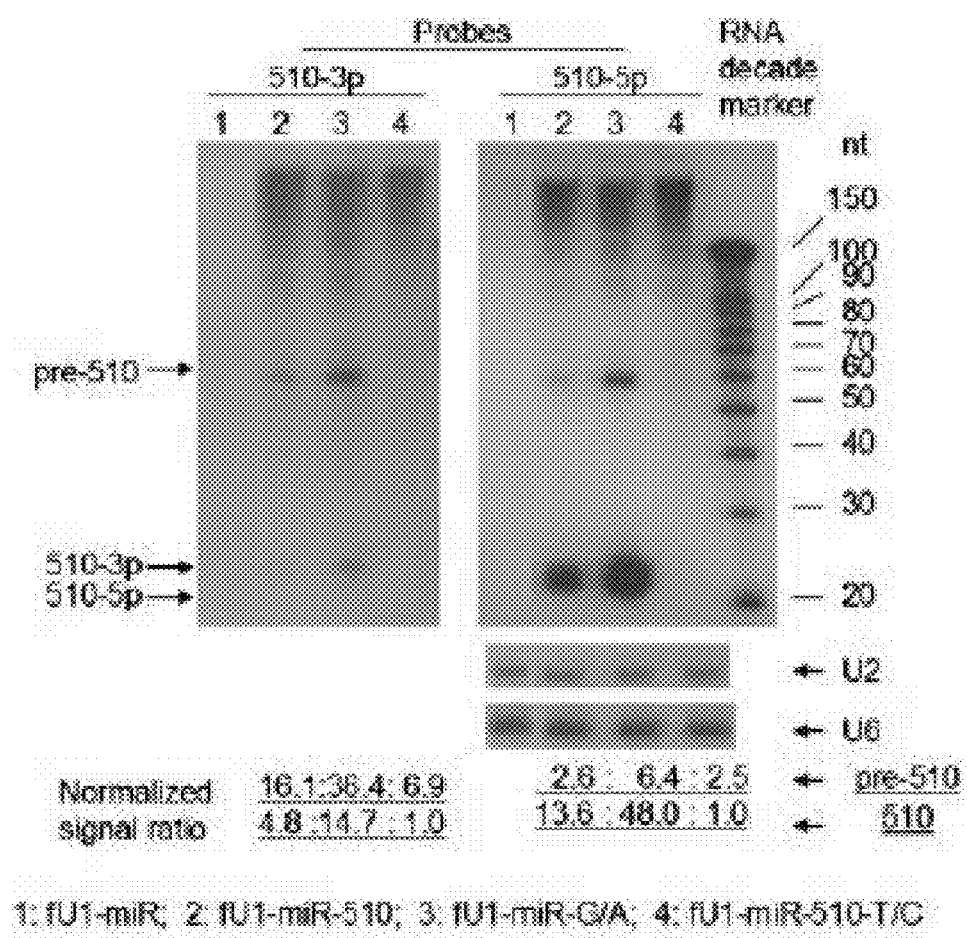

A G/A transition in pri-miR-510 enhanced the production of miR-510-5p and -3p (-3p is miR-510*) (FIG. 5). The G to A transition occurs at the 4th nt upstream of the 5' end of the mature miR-510-5p (FIG. 2). Variants at this position may affect Drosha processing of this substrate since it may provide a more stable stem preceding the mature miRNA sequence. The reporter transfection assay data show that the siRNA activity of the mutant is markedly higher than the wild type (FIG. 5A). Northern blot data show that the production of both pre-miR-510 and mature miR-510-5p/3p are increased (FIG. 5B). Dot blotting data also revealed more clones of the miR-510-G/A than miR-510 (FIG. 16A). The miRNA cloning data show that the generation of the 5p product is the same for both the wild type and mutant, and apparently this SNP does not affect the Drosha cutting sites. However, colonies hybridizing to the 3p probe were not observed in either the wild type or SNP blots.

miR-934-T/G

SNPs could alternate Drosha or Dicer excision sites since their cutting sites are structure based and not sequence based. Variant miR-934-T/G occurs at the first nucleotide of the miR-934-5p (FIG. 2), which is also the Drosha processing site. Because the variant occurs at the 5' end and the base of the 5'end plays an important role in strand selection into miRISC, the T/G transversion of this variant is particularly significant. Transfection and Northern blot results show that this SNP affects the production of both strands (FIG. 10, SEQ ID NOS: 88-95).

Figure 10A:
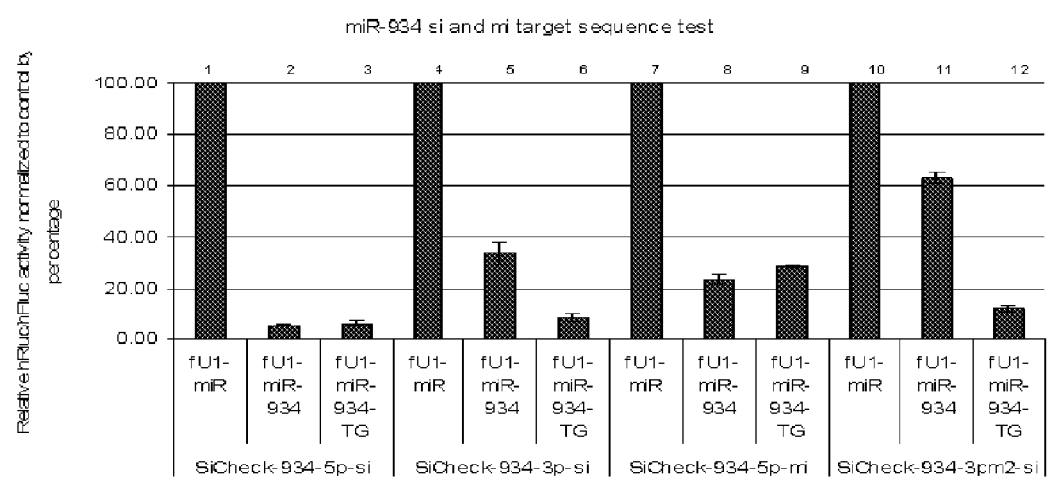
FIG. 10 shows a functional test of miR-934 and miR-934-T/G. a. Transfection test results. Expression of 5p-si and 5p-mi reporters are almost the same, but strong repression of the 3p-si and 3pm2-si reporters are observed from the mutant miRNA. Each bar represents the average of at least three independent transfections with duplicate determinations for each construct. Error bars represent the S.D. b. Northern blot results. Left: blot was probed with a miR-934 5p probe; right blot that was probed with a 3p probe. U2 and U6 snoRNAs were probed as RNA gel loading controls. SiRNA-1 was co-transfected in samples 2, 5, and 6 as a transfection control. Lanes 1 and 2 are from cells transfected with fU1-miR; Lanes 3, 5, and 7 are from cells transfected with fU1-miR-934; Lanes 4, 6, and 8 are from cells transfected with the mutant. c. Nucleotide sequences of miR-934, mir-934-T/C, SiCheck-934-5p-si, SiCheck-934-5p-mi, SiCheck-934-3p-si. (SEQ ID NOS: 88-95).
Figure 10B:
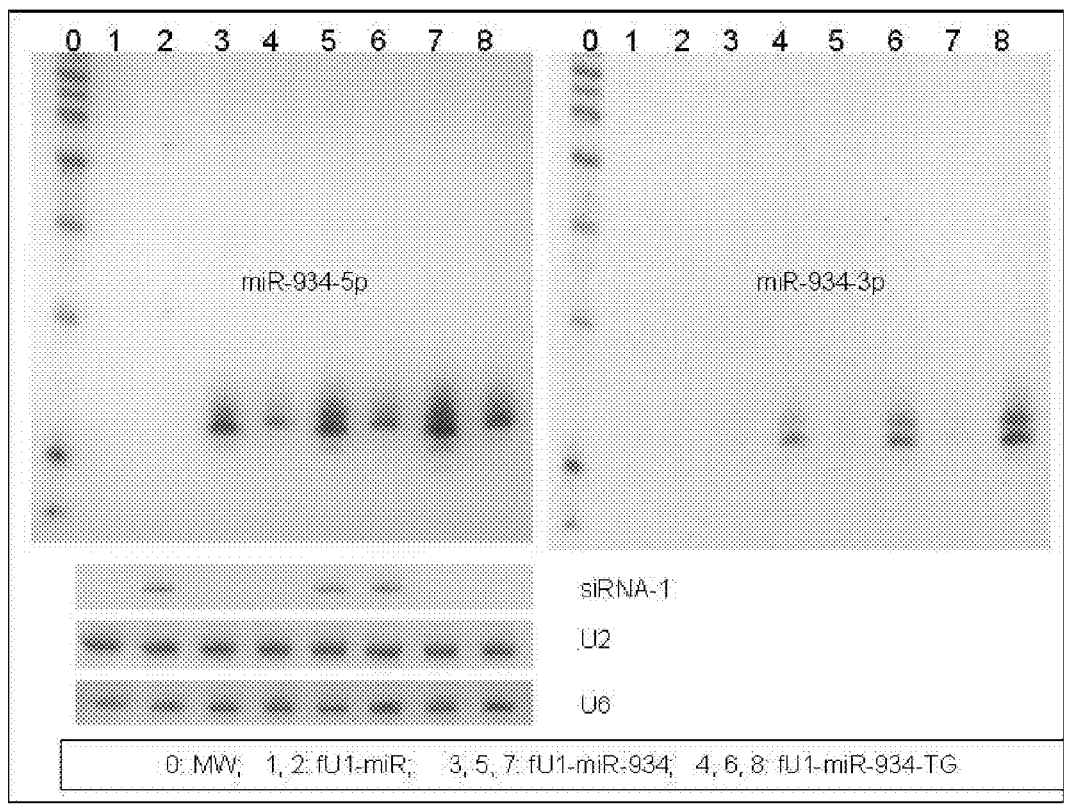

First, the transfection assay shows that repression of the 5p reporter is reduced by the SNP, and Northern blots confirmed the reporter assay results (FIG. 10A). Second, the length of the 5p product seems to be increased in the Northern blot. The most dramatic changes are in the 3p product. Transfections show that repression of the 3p reporter by the SNP is increased, and Northern blots show that the variant produces more 3p than wild type. Thus, the guide strand and passenger strand in miRISC are inverted in the wild type versus mutant miRNAs. Cloning also yielded more 5p wild type clones and more mutant 3p clones. The cloning data also show that the production of 3p is altered, with both the Drosha and Dicer cutting sites being offset by one nucleotide from the wild type, resulting in a different 3p product. This not only produced a novel miRNA, but it also affected the strand selection in miR-934/miR-934*. The wild type miR-934-5p starts with a U and is most likely selected as the predominant guide strand due to the lower thermodynamic stability of the 5' end. The U/G transversion changes the first nucleotide of the 5p product to 'G', which affected the Dicer cutting site, moving it back one nucleotide from the original 'G' to an 'A'. Thus the 3p product in the mutant has a lower 5' end thermodynamic stability and this is probably responsible for altered guide strand selectivity, which is consistent with the reported requirements for asymmetric strand loading.

The foregoing examples and methods of the invention are illustrative only and are not intended to be limiting of the invention in any way. Those of ordinary skill in the art will recognize that various modifications of the foregoing are within the intended scope of the invention.

All references cited are incorporated in their entirety as though fully set forth herein.

References

1. Abelson, J. F. et al. Sequence variants in SLITRK1 are associated with Tourette's syndrome. Science 310, 317-20 (2005).
2. Ambros V. 2003. MicroRNA pathways in flies and worms: growth, death, fat, stress, and timing. Cell 113:673-676.
3. Arisawa, T. et al. A polymorphism of microRNA 27a genome region is associated with the development of gastric mucosal atrophy in Japanese male subjects. Dig Dis Sci 52, 1691-7 (2007).
4. Bartel, D. P. MicroRNAs: genomics, biogenesis, mechanism, and function. Cell 116, 281-97 (2004).
5. Bentwich, I. et al. Identification of hundreds of conserved and nonconserved human microRNAs. Nat Genet 37, 766-70 (2005).
6. Berezikov, E., Chung, W. J., Willis, J., Cuppen, E. & Lai, E. C. Mammalian mirtron genes. Mol Cell 28, 328-36 (2007).
7. Blow, M. J. et al. RNA editing of human microRNAs. Genome Biol 7, R27 (2006).
8. Bottema C D K, Sommer S S. 1993. PCR amplification of specific alleles: rapid detection of known mutations and polymorphisms. Mutat Res 288:93-102.

9. Bushati, N. & Cohen, S. M. microRNA functions. Annu Rev Cell Dev Biol 23, 175-205 (2007).
10. Cai, X., Hagedorn, C. H. & Cullen, B. R. Human microRNAs are processed from capped, polyadenylated transcripts that can also function as mRNAs. Rna 10, 1957-66 (2004).
11. Chen, W. et al. Mutation screening of brain-expressed X-chromosomal miRNA genes in 464 patients with non-syndromic X-linked mental retardation. Eur J Hum Genet 15, 375-8 (2007).
12. Chendrimada, T. P. et al. TRBP recruits the Dicer complex to Ago2 for microRNA processing and gene silencing. Nature 436, 740-4 (2005).
13. Chu, C. Y. & Rana, T. M. Translation Repression in Human Cells by MicroRNAinduced Gene Silencing Requires RCK/p54. PLOS Biol 4, e210 (2006).
14. Clop, A. et al. A mutation creating a potential illegitimate microRNA target site in the myostatin gene affects muscularity in sheep. Nat Genet 38, 813-8 (2006).
15. Croce C M, Calin G A. 2005. miRNAs, cancer, and stem cell division. Cell 122:6-7.
16. Diederichs, S. & Haber, D. A. Sequence variations of microRNAs in human cancer: alterations in predicted secondary structure do not affect processing. Cancer Res 66, 6097-104 (2006).
17. Du T, Zamore P D. 2005. microPrimer: the biogenesis and function of microRNA. Development 132:4645-4652.
18. Duan, R., Pak, C. & Jin, P. Single nucleotide polymorphism associated with mature miR-125a alters the processing of pri-miRNA. Hum Mol Genet 16, 1124-31 (2007).
19. Filipowicz, W., Bhattacharyya, S. N. & Sonenberg, N. Mechanisms of posttranscriptional regulation by microRNAs: are the answers in sight? Nat Rev Genet 9, 102-14 (2008).
20. Giraldez A J, Cinalli R M, Glasner M E, Enright A J, Thomson J M, Baskerville S, Hammond S M, Bartel D P, Schier A F. 2005. MicroRNAs regulate brain morphogenesis in zebrafish. Science 308:833-838.
21. Gottwein, E., Cai, X. & Cullen, B. R. A novel assay for viral microRNA function identifies a single nucleotide polymorphism that affects Drosha processing. J Virol 80, 5321-6 (2006).
22. Griffiths-Jones, S., Saini, H. K., van Dongen, S. & Enright, A. J. miRBase: tools for microRNA genomics. Nucleic Acids Res 36, D154-8 (2008).
23. Haase, A. D. et al. TRBP, a regulator of cellular PKR and HIV-1 virus expression, interacts with Dicer and functions in RNA silencing. EMBO Rep 6, 961-7 (2005).
24. Hammond S M, Bernstein E, Beach D, Hannon G J. 2000. An RNA-directed nuclease mediates post-transcriptional gene silencing in Drosophila cells. Nature 404:293-296.
25. Han, J. et al. Molecular basis for the recognition of primary microRNAs by the Drosha-DGCR8 complex. Cell 125, 887-901 (2006).
26. Han, J. et al. The Drosha-DGCR8 complex in primary microRNA processing. Genes Dev 18, 3016-27 (2004).
27. Harrison P J, Weinberger D R. 2005. Schizophrenia genes, gene expression, and neuropathology: on the matter of their convergence. Mol Psychiatry 10:40-68.
28. Hatfield S D, Shcherbata H R, Fischer K A, Nakahara K, Carthew R W, Ruohola-Baker H. 2005. Stem cell division is regulated by the microRNA pathway. Nature 435:974-978.
29. Hu, Z. et al. Common genetic variants in pre-microRNAs were associated with increased risk of breast cancer in Chinese women. Hum Mutat (2008).
30. Hu, Z. et al. Genetic variants of miRNA sequences and non-small cell lung cancer survival. J Clin Invest 118, 2600-8 (2008).
31. Hutvagner G, McLachlan J, Pasquinelli A E, Balint E, Tuschl T, Zamore P D. 2001. A cellular function for the RNA-interference enzyme Dicer in the maturation of the let-7 small temporal RNA. Science 293:834-838.
32. Hutvagner G, Zamore P D. 2002. A microRNA in a multiple-turnover RNAi enzyme complex. Science 297: 2056-2060.
33. Jablensky A. 2000. Epidemiology of schizophrenia: the global burden of disease and disability. Eur Arch Psychiatry Clin Neurosci 250:274-285.
34. Jazdzewski, K. et al. Common SNP in pre-miR-146a decreases mature miR expression and predisposes to papillary thyroid carcinoma. Proc Natl Acad Sci U S A 105, 7269-74 (2008).
35. Jentsch et al., 1997, Science 277:953-955.
36. Jin P, Zarnescu D C, Ceman S, Nakamoto M, Mowrey J, Jongens T A, Nelson D L, Moses K, Warren S T. 2004. Biochemical and genetic interaction between the fragile X mental retardation protein and the microRNA pathway. Nat Neurosci 7:113-117.
37. Karube Y, Tanaka H, Osada H, Tomida S, Tatematsu Y, Yanagisawa K, Yatabe Y, Takamizawa J, Miyoshi S, Mitsudomi T, Takahashi T. 2005. Reduced expression of Dicer associated with poor prognosis in lung cancer patients. Cancer Sci 96:111-115.
38. Kawahara, Y. et al. Redirection of silencing targets by adenosine-to-inosine editing of miRNAs. Science 315, 1137-40 (2007).
39. Kawahara, Y., Zinshteyn, B., Chendrimada, T. P., Shiekhattar, R. & Nishikura, K. RNA editing of the microRNA-151 precursor blocks cleavage by the Dicer-TRBP complex. EMBO Rep 8, 763-9 (2007).
40. Khvorova, A., Reynolds, A. & Jayasena, S. D. Functional siRNAs and miRNAs exhibit strand bias. Cell 115, 209-16 (2003).
41. Kim V N. 2005. MicroRNA biogenesis: coordinated cropping and dicing. Nat Rev Mol Cell Biol 6:376-385.
42. Klein M E, Impey S, Goodman R H. 2005. Role reversal: the regulation of neuronal gene expression by microRNAs. Curr Opin Neurobiol 15:507-513.
43. Lai E C. 2003. microRNAs: runts of the genome assert themselves. Curr Biol 13:R925-R936.
44. Landthaler M, Yalcin A, Tuschl T. 2004. The human DiGeorge syndrome critical region gene 8 and Its D. melanogaster homolog are required for miRNA biogenesis. Curr Biol 14:2162-2167.
45. Lee, Y., Jeon, K., Lee, J. T., Kim, S. & Kim, V. N. MicroRNA maturation: stepwise processing and subcellular localization. Embo J 21, 4663-70 (2002).
46. Lee, Y. et al. The nuclear RNase III Drosha initiates microRNA processing. Nature 425, 415-9 (2003).
47. Liu, J. et al. A role for the P-body component GW182 in microRNA function. Nat Cell Biol 7, 1261-6 (2005).
48. Martin, M. M. et al. The human angiotensin II type 1 receptor +1166 A/C polymorphism attenuates microrna-155 binding. J Biol Chem 282, 24262-9
49. (2007).
50. Mattick J S, Makunin I V. 2005. Small regulatory RNAs in mammals. Hum Mol Genet 14 Spec No 1:R121-R132.
51. Mishra, P. J., Humeniuk, R., Longo-Sorbello, G. S., Banerjee, D. & Bertino, J. R. A miR-24 microRNA binding-site polymorphism in dihydrofolate reductase gene leads to methotrexate resistance. Proc Natl Acad Sci USA 104, 13513-8 (2007).
52. Mourelatos Z, Dostie J, Paushkin S, Sharma A, Charroux B, Abel L, Rappsilber J, Mann M, Dreyfuss G. 2002. miRNPs: a novel class of ribonucleoproteins containing numerous microRNAs. Genes Dev 16:720-728.

53. Naguibneva I, Ameyar-Zazoua M, Polesskaya A, Ait-Si-Ali S, Groisman R, Souidi M, Cuvellier S, Harel-Bellan A. 2006. The microRNA miR-181 targets the homeobox protein Hox-A11 during mammalian myoblast differentiation. Nat Cell Biol 8:278-284.
54. Okamura, K., Hagen, J. W., Duan, H., Tyler, D. M. & Lai, E. C. The mirtron pathway generates microRNA-class regulatory RNAs in Drosophila. Cell 130, 89-100 (2007).
55. Okamura, K. et al. The regulatory activity of microRNA* species has substantial influence on microRNA and 3' UTR evolution. Nat Struct Mol Biol 15, 354-63 (2008).
56. Palatnik J F, Allen E, Wu X, Schommer C, Schwab R, Carrington J C, Weigel D. 2003. Control of leaf morphogenesis by microRNAs. Nature 425:257-263.
57. Pasquinelli A E, Reinhart B J, Slack F, Martindale M Q, Kuroda M I, Maller B, Hayward D C, Ball E E, Degnan B, Muller P, Spring J, Srinivasan A, Fishman M, Finnerty J, Corbo J, Levine M, Leahy P, Davidson E, Ruvkun G. 2000. Conservation of the sequence and temporal expression of let-7 heterochronic regulatory RNA. Nature 408:86-89.
58. Piercey et al., 1988, Life Sci. 43(4):375-385.
59. Piskounova, E. et al. Determinants of microRNA processing inhibition by the developmentally regulated RNA-binding protein Lin28. J Biol Chem (2008).
60. Purohit et al., 1993, Biol. Psychiatry 33(4):255-260.
61. Rehwinkel, J., Behm-Ansmant, I., Gatfield, D. & Izaurralde, E. A crucial role for GW182 and the DCP1:DCP2 decapping complex in miRNA-mediated gene silencing. Rna 11, 1640-7 (2005).
62. Ro, S., Park, C., Young, D., Sanders, K. M. & Yan, W. Tissue-dependent paired expression of miRNAs. Nucleic Acids Res 35, 5944-53 (2007).
63. Ruby, J. G., Jan, C. H. & Bartel, D. P. Intronic microRNA precursors that bypass Drosha processing. Nature 448, 83-6 (2007).
64. Ruvkun, G. Molecular biology. Glimpses of a tiny RNA world. Science 294, 797-9 (2001).
65. Saunders, M. A., Liang, H. & Li, W. H. Human polymorphism at microRNAs and microRNA target sites. Proc Natl Acad Sci USA 104, 3300-5 (2007).
66. Schwarz, D. S. et al. Asymmetry in the assembly of the RNAi enzyme complex. Cell 115, 199-208 (2003).
67. Seitz, H., Ghildiyal, M. & Zamore, P. D. Argonaute loading improves the 5' precision of both MicroRNAs and their miRNA strands in flies. Curr Biol 18, 147-51 (2008).
68. Sethupathy, P. et al. Human microRNA-155 on chromosome 21 differentially interacts with its polymorphic target in the AGTR1 3' untranslated region: a mechanism for functional single-nucleotide polymorphisms related to phenotypes. Am J Hum Genet 81, 405-13 (2007).
69. Shen, J. et al. A Functional Polymorphism in the miR-146a Gene and Age of Familial Breast/Ovarian Cancer Diagnosis. Carcinogenesis (2008).
70. Sobell J L, Heston L L, Sommer S S. 1993. Novel association approach for determining the genetic predisposition to schizophrenia: case-control resource and testing of the first candidate gene. Am J Med Genet 48:28-35.
71. Sommer S S, Cassady J D, Sobell J L, Bottema C D. 1989. A novel method for detecting point mutations or polymorphisms and its application to population screening for carriers of phenylketonuria. Mayo Clin Proc 64:1361-1372.
72. Sommer S S, Groszbach A R, Bottema C D K. 1992. PCR amplification of specific alleles (PASA) is a general method for rapidly detecting known single-base changes. BioTechniques 12:82-87.
73. Sun G, Li H, Rossi J J. 2007. Cloning and Detecting Signature MicroRNAs from Mammalian Cells. Methods Enzymol 427:123-138.
74. Viswanathan, S. R., Daley, G. Q. & Gregory, R. I. Selective blockade of microRNA processing by Lin28. Science 320, 97-100 (2008).
75. Xu, T. et al. A functional polymorphism in the miR-146a gene is associated with the risk for hepatocellular carcinoma. Carcinogenesis (2008).
76. Yang, W. et al. Modulation of microRNA processing and expression through RNA editing by ADAR deaminases. Nat Struct Mol Biol 13, 13-21 (2006).
77. Yi, R., Qin, Y., Macara, I. G. & Cullen, B. R. Exportin-5 mediates the nuclear export of pre-microRNAs and short hairpin RNAs. Genes Dev 17, 3011-6 (2003).
78. Ying S Y, Lin S L. 2004. Intron-derived microRNAs—fine tuning of gene functions. Gene 342:25-28.
79. Yu, Z. et al. Aberrant allele frequencies of the SNPs located in microRNA target sites are potentially associated with human cancers. Nucleic Acids Res 35, 4535-41 (2007).
80. Zeng Y, Wagner E J, Cullen B R. 2002. Both natural and designed micro RNAs can inhibit the expression of cognate mRNAs when expressed in human cells. Mol Cell 9:1327-1333.
81. Zeng, Y. & Cullen, B. R. Efficient processing of primary microRNA hairpins by Drosha requires flanking nonstructured RNA sequences. J Biol Chem 280, 27595-603 (2005).
82. Zeng, Y. Principles of micro-RNA production and maturation. Oncogene 25, 6156-62 (2006).
83. Zeng, Y., Yi, R. & Cullen, B. R. Recognition and cleavage of primary microRNA precursors by the nuclear processing enzyme Drosha. Embo J 24, 138-48 (2005).
84. Zeng, Y. & Cullen, B. R. Structural requirements for pre-microRNA binding and nuclear export by Exportin 5. Nucleic Acids Res 32, 4776-85 (2004).
85. Zhang, R., Peng, Y., Wang, W. & Su, B. Rapid evolution of an X-linked microRNA cluster in primates. Genome Res 17, 612-7 (2007).

TABLE 1a

Ultra-rare miRNA cohort-specific variants

| ID# | Disease | miRNA | Variant in mature miRNA | Variant in precursor | Gene pool | Novel mature miRNA documented[a] |
|---|---|---|---|---|---|---|
| S358 | Schizophrenia | let-7f-2 | 11 G > A | | 0/7,197 | yes |
| S418 | Schizophrenia | mir-18b | | 32 A > G | 0/7,197 | ? |
| S590 | Schizophrenia | mir-505 | | 8 C > T | 0/7,197 | ? |
| S356 | Schizophrenia | mir-502 | | 13 C > G | 1/7,197[b] | yes |
| S014 | Schizophrenia | mir-188 | 7 C > T (188-3p) | | 0/7,197 | yes |
| MC179 | Psychosis | mir-325 | | 66 G > A | 0/7,197 | ? |
| S711 | Schizophrenia | mir-660 | 15 C > T | | 0/7,197 | yes |

TABLE 1a-continued

Ultra-rare miRNA cohort-specific variants

| ID# | Disease | miRNA | Variant in mature miRNA | Variant in precursor | Gene pool | Novel mature miRNA documented[a] |
|---|---|---|---|---|---|---|
| S596 | Schizophrenia | mir-509-3 | 13 C > T (509-3p) | | 0/7,197 | yes |
| MC149 | Control[c] | mir-510 | | 48 T > C | 0/7,197 | ? |

[a] by functional analysis
[b] one otherwise healthy individual in the gene pool analysis, who has this variant, was found to have a history of depression; the extent of the depression requires further clarification
[c] this individual was ascertained as a control sample, but upon examination of medical history was found to have a history of depression; the extent of the depression requires further clarification TABLE 1b miRNA cohort-specific sequence variants found in the gene pool analyses

| ID# | Disease | miRNA | Variant in mature miRNA | Variant in precursor | Gene pool |
|---|---|---|---|---|---|
| S464 | Schizophrenia | mir-509-3 | 22 G > A (509-3-5p) | | 2/7,197 |
| MC527 | Control | mir-509-3 | 19 C > G (509-3-5p) | | 10/4,962 |
| MC333 | Control | mir-421 | | 73 G > A | 16/4,962 |
| MC40 | Control | mir-934 | 1 T > G | | 4/7,197 |
| MC93 | Control | mir-450-2 | 5 T > C | | 8/4,962 |

TABLE 2

X Chromosome MicroRNA Primers (miRBase V10.1)

| # | miRNA | Oligo | SEQ ID NO. | Sequence | Size (bp) | $T_m$ (° C.) | PCR size (bp) |
|---|---|---|---|---|---|---|---|
| 1 | mir-221 | mir-221D1 | SEQ ID NO. 97: | CAGTTATTCAGAAACATTATAGG | 23 | 62 | 200 |
| | | mir-221U1 | SEQ ID NO. 98: | AGGCAGTTGTGTTGAAATAGTA | 22 | 60 | |
| 2 | mir-222 | mir-222D1 | SEQ ID NO. 99: | TTATTAAAGACTGCCCAATAATC | 23 | 60 | 195 |
| | | mir-222U1 | SEQ ID NO. 100: | CTTCCACAGAGCCCCTCC | 18 | 60 | |
| 3 | mir-188 | mir-188D1 | SEQ ID NO. 101: | AGCATACCCATATGTCGTGC | 20 | 60 | 182 |
| | | mir-188U2 | SEQ ID NO. 102: | TGGTGAAGGAGTGCGTATGT | 20 | 60 | |
| 4 | mir-98 | mir-98D1 | SEQ ID NO. 103: | GAGGCAACACTGCTAAGACT | 20 | 60 | 167 |
| | | mir-98U2 | SEQ ID NO. 104: | CTTTTGCCTGCTGCCCTTAT | 20 | 60 | |
| 5 | let-7f-2 | let-7f-2D1 | SEQ ID NO. 105: | CCAGAACAAGAACCTGAACAG | 21 | 60 | 184 |
| | | let-7f-2U2 | SEQ ID NO. 106: | CCTGATAGTTCCGAGTAGCT | 20 | 60 | |
| 6 | mir-223 | mir-223D1 | SEQ ID NO. 107: | ACATCTCCCAGGAAGATCTC | 20 | 60 | 192 |
| | | mir 223U1 | SEQ ID NO. 108: | GGCAGTCCATTCGTCATATC | 20 | 62 | |
| 7 | mir-325 | mir-325D1 | SEQ ID NO. 109: | ACCACTAGGCCTAAGTACCT | 20 | 60 | 198 |
| | | mir-325U1 | SEQ ID NO. 110: | GCTTAAATATAGGTTTTGAGATG | 23 | 60 | |
| 8 | mir-361 | mir-361D1 | SEQ ID NO: 111: | GATGCTTCTAAAGAAACGGTG | 21 | 60 | 160 |
| | | mir-361U1 | SEQ ID NO. 112: | TAGCAGTGGCACGCTTGAC | 19 | 60 | |

TABLE 2-continued

X Chromosome MicroRNA Primers (miRBase V10.1)

| # | miRNA | Oligo | SEQ ID NO. | Sequence | Size (bp) | $T_m$ (° C.) | PCR size (bp) |
|---|---|---|---|---|---|---|---|
| 9 | mir-224 | mir-224D1 | SEQ ID NO. 113: | TCTGGTGCTTACCTACTGTC | 20 | 60 | 170 |
|   |   | mir-224U1 | SEQ ID NO. 114: | TGGGGACCCATCATCAAAAG | 20 | 60 |   |
| 10 | mir-374a | mir-374D1 | SEQ ID NO. 115: | AGGAGCTCACAGTCTAACTG | 20 | 60 | 182 |
|   |   | mir-374U1 | SEQ ID NO. 116: | GTTCCTCACCTCTCTTGATG | 20 | 60 |   |
| 11 | mir-384 | mir-384D1 | SEQ ID NO. 117: | GCCAGTTAGCATCTTGAAGG | 20 | 60 | 186 |
|   |   | mir-384U1 | SEQ ID NO. 118: | GTTCCTTGCCTTTTAACTAGTAT | 23 | 62 |   |
| 12 | mir-220 | mir-220D1 | SEQ ID NO. 119: | TCCAGCTGACGCACTTGCT | 19 | 60 | 208 |
|   |   | mir-220U1 | SEQ ID NO. 120: | GATGCAGTAGGTCTCATTCG | 20 | 60 |   |
| 13 | mir-92-2 | mir-92-2D1 | SEQ ID NO. 121: | CTAAATATCAGAACTTACGGCT | 22 | 60 | 177 |
|   |   | mir-92-2U1 | SEQ ID NO. 122: | GTGAACACACCTTCATGCGT | 20 | 60 |   |
| 14 | mir-19b-2 | mir-19b-2D1 | SEQ ID NO. 123: | TGAGTGCTGGAGATACGCAT | 20 | 60 | 191 |
|   |   | mir-19b-2U1 | SEQ ID NO. 124: | CTCTTGGATAACAAATCTCTTG | 22 | 60 |   |
| 15 | mir-106a | mir-106aD1 | SEQ ID NO. 125: | TTATGCACAAACTACAGTTCTC | 22 | 60 | 166 |
|   |   | mir-106aU1 | SEQ ID NO. 126: | AGAAGAGCTCCTGGAAGACT | 20 | 60 |   |
| 16 | mir-424 | mir-424D2 | SEQ ID NO. 127: | GGGAGCGGGCACCTGGT | 17 | 60 | 178 |
|   |   | mir-424U3 | SEQ ID NO. 128: | GCTTCCTTCAGTCATCCAGT | 20 | 60 |   |
| 17 | mir-105-1 | mir-105-1D | SEQ ID NO. 129: | AATGGCTTTGGTCCAGAAGC | 20 | 60 | 165 |
|   |   | mir-105-1U | SEQ ID NO. 130: | CTACTCCTATATATTGGATGTC | 22 | 60 |   |
| 18 | mir-105-2 | mir-105-2D | SEQ ID NO. 131: | GAGTGGCTTTGTTCCAGAAG | 20 | 60 | 170 |
|   |   | mir-105-2U | SEQ ID NO. 132: | GTCTACTCCCTATAACCTGG | 20 | 60 |   |
| 19 | mir-651 | mir-651D1 | SEQ ID NO. 133: | CTTGTGATGTAGATTAAATCGT | 22 | 58 | 368 |
|   |   | mir-651U1 | SEQ ID NO. 134: | CACTTTATTCATCCTGACTCT | 21 | 58 |   |
| 20 | mir-532 | mir-532D1 | SEQ ID NO. 135: | TGTACACAAGCACACCTTCT | 20 | 58 | 328 |
|   |   | mir-532U1 | SEQ ID NO. 136: | GAAGCAGGACAGTCATCCA | 19 | 58 |   |
| 21 | mir-660 | mir-660D1 | SEQ ID NO. 137: | GCACCTGACACTTTAATCTCA | 21 | 60 | 365 |
|   |   | mir-660U1 | SEQ ID NO. 138: | CTAATACCTCCACTAGATAGG | 21 | 60 |   |
| 22 | mir-652 | mir-652D2 | SEQ ID NO. 139: | TGTTTGTGTGCTATGGCCAT | 20 | 58 | 449 |
|   |   | mir-652U2 | SEQ ID NO. 140: | GTTCTCCTATATGATGGCTC | 20 | 58 |   |
| 23 | mir-934 | mir-934D1 | SEQ ID NO. 141: | TATGTATCTCGTGGATCTGC | 20 | 58 | 259 |
|   |   | mir-934U1 | SEQ ID NO. 142: | TTACAAGATAGGAAGTGCATAT | 22 | 58 |   |

TABLE 2-continued

X Chromosome MicroRNA Primers (miRBase V10.1)

| # | miRNA | Oligo | SEQ ID NO. | Sequence | Size (bp) | $T_m$ (° C.) | PCR size (bp) |
|---|---|---|---|---|---|---|---|
| 24 | mir-421 | mir-421D1 | SEQ ID NO. 143: | CATTGTCCGTGTCTATGGC | 19 | 58 | 345 |
|  |  | mir-421U1 | SEQ ID NO. 144: | AATTGGAGATGGTACTTGAGA | 21 | 58 |  |
| 25 | mir-766 | mir-766D1 | SEQ ID NO. 145: | TATACACAGAGGATTGCTTAG | 21 | 58 | 308 |
|  |  | mir-766U1 | SEQ ID NO. 146: | CCTCATTACTCTCATTTCCTG | 21 | 60 |  |
| 26 | mir-450b | mir-450bD3 | SEQ ID NO. 147: | ATCGCTGACTTGTGTCACTA | 20 | 58 | 543 |
|  |  | mir-450bU2 | SEQ ID NO. 148: | TATTCTAGGCCCACTGCTG | 19 | 58 |  |
| 27 | mir-890 | mir-890D1 | SEQ ID NO. 149: | TTCAGGGTTCAGGCATCCT | 19 | 58 | 291 |
|  |  | mir-890U1 | SEQ ID NO. 150: | ACACCTAAGGTTCAGGTGG | 19 | 58 |  |
| 28 | mir-888 | mir-888D1 | SEQ ID NO. 151: | GACATCATGCTGTGCTCAG | 19 | 58 | 279 |
|  |  | mir-888U1 | SEQ ID NO. 152: | TGCCTGAATTCCAGGTGGT | 19 | 58 |  |
| 29 | mir-892a | mir-892aD1 | SEQ ID NO. 153: | TCCAGATTCAGGCATCCTG | 19 | 58 | 289 |
|  |  | mir-892aU1 | SEQ ID NO. 154: | TTAAGGATGCCTGAGGTTCA | 20 | 58 |  |
| 30 | mir-892b | mir-892bD1 | SEQ ID NO. 155: | TCAAATTGTTCAGGCATCATG | 21 | 58 | 279 |
|  |  | mir-892bU1 | SEQ ID NO. 156: | ACATGGCCAGCTAGGTTCT | 19 | 58 |  |
| 31 | mir-891b | mir-891bD1 | SEQ ID NO. 157: | TAGCTACATAGGTCGTGAATA | 21 | 58 | 315 |
|  |  | mir-891bU1 | SEQ ID NO. 158: | CTACTACCAGTATCACTACAA | 21 | 58 |  |
| 32 | mir-891a | mir-891aD1 | SEQ ID NO. 159: | CATGCTGATAGTTACACAGG | 20 | 58 | 319 |
|  |  | mir-891aU1 | SEQ ID NO. 160: | ACTACCAGTGTCACTACAAG | 20 | 58 |  |
| 33 | mir-509-2 | mir-509-2D2 | SEQ ID NO. 161: | ccaaattccaatggccacg | 19 | 58 | 521 |
|  |  | mir-509-2U2 | SEQ ID NO. 162: | atttggatgttggagtaggc | 21 | 58 |  |
| 34 | mir-509-3 | mir-509-3D1 | SEQ ID NO. 163: | TCTGTGAGTAACAGGACCTA | 20 | 58 | 690 |
|  |  | mir-509-3U1 | SEQ ID NO. 164: | TGAGAAAGGAAGCTAACCATT | 21 | 58 |  |
| 35 | mir-767 | mir-767D1 | SEQ ID NO. 165: | TGATATCTCCTCCAGCATCA | 20 | 58 | 331 |
|  |  | mir-767U1 | SEQ ID NO. 166: | TGATCTAAGAGTAGAGAGTCA | 21 | 58 |  |
| 36 | mir-374b | mir-374bD1 | SEQ ID NO. 167: | GTAAAGTGTTTGTCATAGGCA | 21 | 58 | 329 |
|  |  | mir-374bU1 | SEQ ID NO. 168: | CCTACAATGTGCACCGGAT | 19 | 58 |  |
| 37 | mir-542 | mir-542D1 | SEQ ID NO. 169: | GGTGGGATTAGAGCTGAAG | 19 | 58 | 435 |
|  |  | mir-542U1 | SEQ ID NO. 170: | GGCATTCCCATTACACTCC | 19 | 58 |  |
| 38 | mir-513-1 | mir-513-1D2 | SEQ ID NO. 171: | CAAGTTGCATTGTCCCTTGG | 20 | 60 | 486 |
|  |  | mir-513-1U2 | SEQ ID NO. 172: | TGGAGTAAAGCATTCCAGCT | 20 | 58 |  |

TABLE 2-continued

X Chromosome MicroRNA Primers (miRBase V10.1)

| # | miRNA | Oligo | SEQ ID NO. | Sequence | Size (bp) | $T_m$ (° C.) | PCR size (bp) |
|---|---|---|---|---|---|---|---|
| 39 | mir-20b | mir-20bD1 | SEQ ID NO. 173: | GTAGCAATGTCTTTGAATATTC | 22 | 58 | 189 |
| | | mir-20bU1 | SEQ ID NO. 174: | TGTTGGGAACAGATGGTGG | 19 | 58 | |
| 40 | mir-362 | mir-362D1 | SEQ ID NO. 175: | ACATGCACACATACAAACACA | 21 | 58 | 199 |
| | | mir-362U1 | SEQ ID NO. 176: | ATAGCAAACACAAACATGTGAA | 22 | 58 | |
| 41 | mir-18b | mir-18bD1 | SEQ ID NO. 177: | ACCACTGAAATGTGTCCTATT | 21 | 58 | 209 |
| | | mir-18bU1 | SEQ ID NO. 178: | GAGAACTGTAGTTTGTGCATA | 21 | 58 | |
| 42 | mir-510 | mir-510D1 | SEQ ID NO. 179: | ATGTGCTAAGAAAAGCATACC | 21 | 58 | 219 |
| | | mir-510U1 | SEQ ID NO. 180: | AGAGGTTGTTTGAAAAGTGTG | 21 | 58 | |
| 43 | mir-363 | mir-363D1 | SEQ ID NO. 181: | TAGCTTACTGTAGCGCTGAT | 20 | 58 | 229 |
| | | mir-363U1 | SEQ ID NO. 182: | ACTTGTCCCGGCCTGTGG | 18 | 60 | |
| 44 | mir-503 | mir-503D1 | SEQ ID NO. 183: | TGCAATCTTGGGTCTCGCT | 19 | 58 | 239 |
| | | mir-503U1 | SEQ ID NO. 184: | GGGCAGTATTCCTGGCTAG | 19 | 60 | |
| 45 | mir-500 | mir-500D1 | SEQ ID NO. 185: | AAGCTCAAGAACTGTTCTCTT | 21 | 58 | 250 |
| | | mir-500U1 | SEQ ID NO. 186: | ATAAATACTTGTGGAATGGATG | 22 | 58 | |
| 46 | mir-501 | mir-501D1 | SEQ ID NO. 187: | CAGAGATACTTTGCAGGAATG | 21 | 60 | 260 |
| | | mir-501U1 | SEQ ID NO. 188: | AAGAATGAATGAGGGTCAGAG | 21 | 60 | |
| 47 | mir-505 | mir-505D1 | SEQ ID NO. 189: | ATGATGCAAATGAGTATTAGGA | 22 | 58 | 270 |
| | | mir-505U1 | SEQ ID NO. 190: | TTCTAGATTATGGGTCATTCC | 21 | 58 | |
| 48 | mir-452 | mir-452D1 | SEQ ID NO. 191: | GCCAGCTGCACATTCCGA | 18 | 58 | 278 |
| | | mir-452U1 | SEQ ID NO. 192: | GTTGGTAAGCGTGCCAGG | 18 | 58 | |
| 49 | mir-504 | mir-504D1 | SEQ ID NO. 193: | AAGAGACTTATCAGGATTGAG | 21 | 58 | 289 |
| | | mir-504U1 | SEQ ID NO. 194: | CCATCCATTTCCCACATAGA | 20 | 58 | |
| 50 | mir-502 | mir-502D1 | SEQ ID NO. 195: | TCACCTAATATTCCTGCACG | 20 | 58 | 299 |
| | | mir-502U1 | SEQ ID NO. 196: | GGTGATGTCTAGGCTCTCT | 19 | 58 | |
| 51 | mir-507 | mir-507D1 | SEQ ID NO. 197: | TGATGGTGGTGGCACTGAC | 19 | 60 | 310 |
| | | mir-507U1 | SEQ ID NO. 198: | TCCTAGTGGACTGAGAGTGT | 20 | 60 | |
| 52 | mir-545 | mir-545D1 | SEQ ID NO. 199: | CAAAGAACTGTGTAGGAAGGA | 21 | 60 | 320 |
| | | mir-545U1 | SEQ ID NO. 200: | TCATCACTCGACAGTGATGG | 20 | 60 | |
| 53 | mir-509-1 | mir-509D1 | SEQ ID NO. 201: | GTCCAGCATGGAAGTGGAG | 19 | 60 | 330 |
| | | mir-509U1 | SEQ ID NO. 202: | TGGATTGGATTCTGCAGAAGT | 21 | 60 | |

TABLE 2-continued

X Chromosome MicroRNA Primers (miRBase V10.1)

| # | miRNA | Oligo | SEQ ID NO. | Sequence | Size (bp) | $T_m$ (° C.) | PCR size (bp) |
|---|---|---|---|---|---|---|---|
| | | mir-509D2 | SEQ ID NO. 203: | TGGACAAAGGACTTCTGTAG | 20 | 58 | ~920 |
| 54 | mir-450-2 | mir-450-2D1 | SEQ ID NO. 204: | TAGTGCATATTAGGAACACATC | 22 | 60 | 339 |
| | | mir-450-2U1 | SEQ ID NO. 205: | ATAGGTATATAGGGAGCATTCT | 22 | 60 | |
| 55 | mir-450-1 | mir-450-1D1 | SEQ ID NO. 206: | CACAGAAGTAAACCACAGATA | 21 | 58 | 349 |
| | | mir-450-1U1 | SEQ ID NO. 207: | TTGTGGTATAAAGGTGACCAA | 21 | 58 | |
| 56 | mir-448 | mir-448D1 | SEQ ID NO. 208: | CCAGGCCAGAAGAGGCTT | 18 | 58 | 369 |
| | | mir-448U1 | SEQ ID NO. 209: | AAGGTCATAGCAGTCAGTAC | 20 | 58 | |
| 57 | mir-508 | mir-508D1 | SEQ ID NO. 210: | AAGACCTGCCTATGGGAGT | 19 | 58 | 379 |
| | | mir-508U1 | SEQ ID NO. 211: | ACTGAAGAGAAGAAGTCCTC | 20 | 58 | |
| 58 | mir-506 | mir-506D1 | SEQ ID NO. 212: | CAGATTCTGGAGCAGATCTC | 20 | 60 | 389 |
| | | mir-506U1 | SEQ ID NO. 213: | CAGAACTACCCACTCAGTGA | 20 | 60 | |
| 59 | mir-513-2 | mir-513-2D1 | SEQ ID NO. 214: | GAGTCCACAGTTCCTATGTA | 20 | 58 | 399 |
| | | mir-513-2U1 | SEQ ID NO. 215: | CTCACTTGGGGCAGGATG | 18 | 58 | |

TABLE 3

Variants found in cases and controls[a]

| ID# | miRNA | Variant in Precursor | # of schizophrenia patients with the variant (n = 193) | # of control patients with the variant (n = 191) |
|---|---|---|---|---|
| S329; MC124; MC178; MC235 | mir-890 | 66 G > C | 1 | 3 |
| many | mir-888 | 77 A > C | 39 | 32 |
| S014; S104; S319; S599; MC73; MC207; MC424; MC515 | mir-891b | 35 C > G | 4 | 4 |
| S211; S508; MC129; MC162; MC285; MC398 | mir-509-1 | 54 insTGA | 2 | 4 |
| S345; S433; MC348; MC370 | mir-509-2 | 9 G > T | 2 | 2 |

[a] all 5 variants were found with similar frequencies in cases and controls

TABLE 4

With 509-2

| ID# | Disease | Gender | Ethnicity | miRNA | Variant in mature miRNA | Variant in Precursor | # of schizophrenia patients with the variant (n = 288) | # of control patients with the variant (n = 192) |
|---|---|---|---|---|---|---|---|---|
| S329; MC124; MC178 | schizophrenia & controls | all male | all Caucasian | mir-890 | | 66 G < C | 1 | 3 |
| | schizophrenia & controls | all male | all Caucasian | mir-888 | | 77 A < C | 53 | 32 |
| S599; S014; S104; S319; | schizophrenia & controls | all male | all Caucasian | mir-891b | | 35 C < G | 4 | 4 |

TABLE 4-continued

| | | | | | | # of schizophrenia patients with the variant (n = 288) | # of control patients with the variant (n = 192) | |
|---|---|---|---|---|---|---|---|---|
| ID# | Disease | Gender | Ethnicity | miRNA | Variant in mature miRNA | Variant in Precursor | | |

With 509-2

| ID# | Disease | Gender | Ethnicity | miRNA | Variant in mature miRNA | Variant in Precursor | # schiz (n=288) | # ctrl (n=192) | |
|---|---|---|---|---|---|---|---|---|---|
| MC73; MC207 | schizophrenia & controls | all male | all Caucasian | mir-509-1 | | 54 insTGA | 3 | 4 | |
| 6 | 509-2 | g146148052t | in precursor; 11 bases upstream of the 5' end of the mature miRNA | 1/192 | 2/192 | S433; MC348; MC370 | NA | 1/94 | yes |

TABLE 5

Without 509-2

| ID# | Disease | Gender | Ethnicity | miRNA | Variant in mature miRNA | Variant in Precursor | # of schizophrenia patients with the variant (n = 288) | # of control patients with the variant (n = 192) |
|---|---|---|---|---|---|---|---|---|
| S329; MC124; MC178 | schizophrenia & controls | all male | all Caucasian | mir-890 | | 66 G < C | 1 | 3 |
| | schizophrenia & controls | all male | all Caucasian | mir-888 | | 77 A < C | 53 | 32 |
| S599; S014; S104; S319; MC73; MC207 | schizophrenia & controls | all male | all Caucasian | mir-891b | | 35 C < G | 4 | 4 |
| | schizophrenia & controls | all male | all Caucasian | mir-509-1 | | 54 insTGA | 3 | 4 |

TABLE 6

Target genes of miRNAs in which we found ultra-rare cohort-specific variants.

| Genes | Function | miRNAs with ultra rare variants have binding site in 3'UTR |
|---|---|---|
| CLCN5 | Chloride channel 5 (nephrolithiasis 2, X-linked, Dent disease) Mutations in this gene have been found in Dent disease and renal tubular disorders complicated by nephrolithiasis | Let-7f, miR-502, miR-18b, miR-660, |
| HMGA2 | HMG proteins function as architectural factors and are essential components of the enhancesome. Identification of the deletion, amplification, and rearrangement of this gene that are associated with myxoid liposarcoma suggests a role in adipogenesis and mesenchymal differentiation. | Let-7f, miR-505 |
| NRXN3 | Neurexins are a family of proteins that function in the vertebrate nervous system as cell adhesion molecules and receptors. | Let-7f |
| DISC1 | Disrupted in schizophrenia 1: The protein is involved in neurite outgrowth and cortical development through its interaction with other proteins. This gene is disrupted by a t(1; 11)(q42.1; q14.3) translocation which segregates with schizophrenia and related psychiatric disorders in a large Scottish family. | Let-7f, miR-18b, miR-510, miR-188, miR-502 |
| NRG1 | Neuregulin 1: Interacts with the NEU/ERBB2 receptor tyrosine kinase to increase its phosphorylation on tyrosine residues. It induces the growth and differentialtion of epithelial, neuronal, glial and other types of cells. | miR-505 |
| MECP2 | Methyl CpG binding protein 2: Mutations of MECP2 are the cause of some cases of Rett syndrome, a progressive neurologic developmental disorder, and are one of the most common causes of mental retardation in females. | Let-7f, miR-188 miR-325, miR-18b |

TABLE 6-continued

Target genes of miRNAs in which we found ultra-rare cohort-specific variants.

| Genes | Function | miRNAs with ultra rare variants have binding site in 3'UTR |
|---|---|---|
| RGS4 | Regulator of G-protein signaling 4: It negatively regulates signaling upstream or at the level of the heterotrimeric G protein and is localized in the cytoplasm. | miR-18b, miR-502 |
| GRM3 | Glutamate receptor, metabotropic 3: L-glutamate is the major excitatory neurotransmitter in the central nervous system and activates both ionotropic and metabotropic glutamate receptors. Glutamatergic neurotransmission is involved in most aspects of normal brain function and can be perturbed in many neuropathologic conditions. | miR-325 |

TABLE 7

Oligos used to clone pri-miRNA and probes for northern blots hsa-let-7f-2

| | | |
|---|---|---|
| 5xho-let7f2 | SEQ ID NO. 216: | attatCTCGAGaatctctcaggtaactctcc |
| 3BamH-let7f2 | SEQ ID NO. 217: | attatGGATCCAGAGTTGCAGTCAGGAAATG |
| 5x-Let7f2-si | SEQ ID NO. 218: | TCGAAACTATACAATCTACTACCTCA |
| 3s-Let7f2-si | SEQ ID NO. 219: | CTAGTGAGGTAGTAGATTGTATAGTT |
| 5x-Let7f2-m-si | SEQ ID NO. 220: | TCGAAACTATACAATTTACTACCTCA |
| 3s-Let7f2-m-si | SEQ ID NO. 221: | CTAGTGAGGTAGTAAATTGTATAGTT |

Oligo for rmutagenesis

| | | |
|---|---|---|
| 5-let7f2G-A | SEQ ID NO. 222: | GGGATGAGGTAGTAAATTGTATAGTTTTAG |
| 3-let7f2G-A | SEQ ID NO. 223: | CTAAAACTATACAATTTACTACCTCATCCC |
| 5x-let7f-mi | SEQ ID NO. 224: | tcgaGGGTATACGGTCTACTACCTCA |
| 3S-let7f-mi | SEQ ID NO. 225: | ctagTGAGGTAGTAGACCGTATACCC |
| 5x-let7f-m-mi | SEQ ID NO. 226: | tcgaGGGTATACGGTTTACTACCTCA |
| 3S-let7f-m-mi | SEQ ID NO. 227: | ctagTGAGGTAGTAAACCGTATACCC |
| let7f2 probe | SEQ ID NO. 228: | AACTATACAATCTACTACCTCA | hsa-mir-18b

| | | |
|---|---|---|
| 5Xho-miR18b | SEQ ID NO. 229: | tatCTCGAGCTACTGAGAACTGTAGTTTGTGCA |
| 3BamH-miR18b | SEQ ID NO. 230: | tatGGATCCACTGAAATGTGTCCTATTCAAATT |
| 5x-18b-si | SEQ ID NO. 231: | tcgaCTAACTGCACTAGATGCACCTTA |
| 3s-18b-si | SEQ ID NO. 232: | ctagTAAGGTGCATCTAGTGCAGTTAG |
| 5x-18b-mi | SEQ ID NO. 233: | tcgagaAACTGCACatcATGCACCTTA |
| 3s-18b-mi | SEQ ID NO. 234: | ctagTAAGGTGCATGATGTGCAGTTTC |
| 5x-18bStar-si | SEQ ID NO. 235: | tcgaGCCAGAAGGGGCATTTAGGGCA |
| 3s-18bStar-si | SEQ ID NO. 236: | ctagTGCCCTAAATGCCCCTTCTGGC |
| 5x-18bStar-mi | SEQ ID NO. 237: | tcgacgCAGAAGGccgATTTAGGGCA |
| 3s-18bStar-mi | SEQ ID NO. 238: | ctagTGCCCTAAATCGGCCTTCTGCG | hsa-mir-505

| | | |
|---|---|---|
| 5Xho-miR505 | SEQ ID NO. 239: | tatCTCGAGCATACTGTCATTGAAAGCACTTAC |
| 3BamH-miR505 | SEQ ID NO. 240: | tatGGATCCTGAGCAAATGAATGGGAGCAGTAA |
| 5x-505-si | SEQ ID NO. 241: | tcgaAGGAAACCAGCAAGTGTTGACG |
| 3s-505-si | SEQ ID NO. 242: | ctagCGTCAACACTTGCTGGTTTCCT |
| 5x-505-mi | SEQ ID NO. 243: | tcgatcGAAACCAcgtAGTGTTGACG |
| 3s-505-mi | SEQ ID NO. 244: | ctagCGTCAACACTACGTGGTTTCGA |
| 5x-505Star-si | SEQ ID NO. 245: | tcgaACATCAATACTTCCTGGCTCCC |
| 3s-505Star-si | SEQ ID NO. 246: | ctagGGGAGCCAGGAAGTATTGATGT |
| 5x-505Star-mi | SEQ ID NO. 247: | tcgatgATCAATAgaaCCTGGCTCCC |
| 3s-505STar-mi | SEQ ID NO. 248: | ctagGGGAGCCAGGTTCTATTGATCA |

TABLE 7-continued

Oligos used to clone pri-miRNA and probes for northern blots hsa-mir-502

| 5Xho-miR502 | SEQ ID NO. 249: | tatCTCGAGAATATGTGTAGGAGACTTG |
| 3BamH-miR502 | SEQ ID NO. 250: | tatGGATCCTGTCTCACTCTGGATACCTG |

| 5x-502-5p-si | SEQ ID NO. 251: | tcgaTAGCACCCAGATAGCAAGGAT |
| 3s-502-5p-si | SEQ ID NO. 252: | ctagATCCTTGCTATCTGGGTGCTA |

| 5x-502-5p-mi | SEQ ID NO. 253: | tcgaatGCACCCtctTAGCAAGGAT |
| 3s-502-5p-mi | SEQ ID NO. 254: | ctagATCCTTGCTAAGAGGGTGCAT |

| 5x-502-3p-si | SEQ ID NO. 255: | tcgaTGAATCCTTGCCCAGGTGCATT |
| 3s-502-3p-si | SEQ ID NO. 256: | ctagAATGCACCTGGGCAAGGATTCA |

| 5x-502-3p-mi | SEQ ID NO. 257: | tcgaacAATCCTTcggCAGGTGCATT |
| 3s-502-3p-mi | SEQ ID NO. 258: | ctagAATGCACCTGCCGAAGGATTGT |

| miR-502-5p probe | SEQ ID NO. 259: | TAGCACCCAGATAGCAAGGAT |
| miR-502-3p probe | SEQ ID NO. 260: | AATCCTTGCCCAGGTGCATTGCATT | hsa-mir-188

| 5Xho-miR188 | SEQ ID NO. 261: | tatCTCGAGCTGCCCACTTGCACCCCCCAGGCC |
| 3BamH-miR188 | SEQ ID NO. 262: | tatGGATCCCACCACATGGGTGTGTGTTTTTCT |

| 5x-188-5p-si | SEQ ID NO. 263: | tcgaCCCTCCACCATGCAAGGGATG |
| 3s-188-5p-si | SEQ ID NO. 264: | ctagCATCCCTTGCATGGTGGAGGG |

| 5x-188-5p-mi | SEQ ID NO. 265: | tcgaggCTCCACgtaGCAAGGGATG |
| 3s-188-5p-mi | SEQ ID NO. 266: | ctagCATCCCTTGCTACGTGGAGCC |

| 5x-188-3p-si | SEQ ID NO. 267: | tcgaTGCAAACCCTGCATGTGGGAG |
| 3s-188-3p-si | SEQ ID NO. 268: | ctagCTCCCACATGCAGGGTTTGCA |

| 5x-188-3p-mi | SEQ ID NO. 269: | tcgaacCAAACCgacCATGTGGGAG |
| 3s-188-3p-mi | SEQ ID NO. 270: | ctagCTCCCACATGGTCGGTTTGGT |

| 5x-188-3pm-si | SEQ ID NO. 271: | tcgaTGCAAACCCTGCATATGGGAG |
| 3s-188-3pm-si | SEQ ID NO. 272: | ctagCTCCCATATGCAGGGTTTGCA |

| 5x-188-3pm-mi | SEQ ID NO. 273: | tcgaacCAAACCgacCATGTGGGAG |
| 3s-188-3pm-mi | SEQ ID NO. 274: | ctagCTCCCATATGGTCGGTTTGGT | hsa-mir-325

| 5Xho-miR325 | SEQ ID NO. 275: | tatCTCGAGGTTCTGTGAGAAAAAGTTGCTTAA |
| 3BamH-miR-325 | SEQ ID NO. 276: | tatGGATCCTAACCACCACTAGGCCTAAGTACC |

Oligo for mutagensis

| 5-miR325-mut | SEQ ID NO. 277: | CATAATTTGTTTATTaAGGACCTCCTATCAA |
| 3-miR325-mut | SEQ ID NO. 278: | TTGATAGGAGGTCCTTAATAAACAAATTATG |

| 5Xho-miR325-L | SEQ ID NO. 279: | tatCTCGAgacagggattgtatggctta |
| 3BamH-miR-325-L | SEQ ID NO. 280: | tatGGATCcctcaacacactgaaatctg |

| 5Xho-miR325-s | SEQ ID NO. 281: | tatCTCGAGATTCAAGTCCACAGAACCA |
| 3BamH-miR-325-s | SEQ ID NO. 282: | tatGGATCcTCAAAATGTAGGATGTTG |

| 5x-325-5p-siL | SEQ ID NO. 283: | tcgaACAAACACTTACTGGACACCTACTAGGAA |
| 3s-325-5p-siL | SEQ ID NO. 284: | ctagTTCCTAGTAGGTGTCCAGTAAGTGTTTGT |

| 5x-325-3p-siL | SEQ ID NO. 285: | tcgaTTGATAGGAGGTCCTCAATAAACAAATT |
| 3s-325-3p-siL | SEQ ID NO. 286: | ctagAATTTGTTTATTGAGGACCTCCTATCAA |

| 5x-325-si | SEQ ID NO. 287: | tcgaACACTTACTGGACACCTACTAGG |
| 3s-325-si | SEQ ID NO. 288: | ctagCCTAGTAGGTGTCCAGTAAGTGT |

| 5x-325-mi | SEQ ID NO. 289: | tcgatgACTTACTGctgACCTACTAGG |
| 3s-325-mi | SEQ ID NO. 290: | ctagCCTAGTAGGTCAGCAGTAAGTCA | hsa-mir-510

| 5Xho-miR510 | SEQ ID NO. 291: | tatCTCGagtcctgaaaactGCCA |
| 3BamH-miR510 | SEQ ID NO. 292: | tatGGATCCTTGCAAGTTTGTAAAGAAGG |

TABLE 7-continued

Oligos used to clone pri-miRNA and probes for northern blots

| | | |
|---|---|---|
| miR-510-5p probe | SEQ ID NO. 293: | GTGATTGCCACTCTCCTGAGTA |
| miR-510-3p (star) probe | SEQ ID NO. 294: | CCACTCTTAGAGGTTTCAATCA |
| 5x-510Star-si | SEQ ID NO. 295: | tcgaCCACTCTTAGAGGTTTCAATCA |
| 3s-510Star-si | SEQ ID NO. 296: | ctagTGATTGAAACCTCTAAGAGTGG |
| 5x-510Star-mi | SEQ ID NO. 297: | tcgaggACTCTTActcGTTTCAATCA |
| 3s-510Star-mi | SEQ ID NO. 298: | ctagTGATTGAAACgagTAAGAGTcc |
| 5x-510Star-m-si | SEQ ID NO. 299: | tcgaCCACTCTTAGAGGTTTCAgTCA |
| 3s-510Star-m-si | SEQ ID NO. 300: | ctagTGAcTGAAACCTCTAAGAGTGG |
| 5x-510Star-m-mi | SEQ ID NO. 301: | tcgaggACTCTTActcGTTTCAgTCA |
| 3s-510Star-m-mi | SEQ ID NO. 302: | ctagTGAcTGAAACgagTAAGAGTcc |
| 5x-510-si | SEQ ID NO. 303: | tcgaGTGATTGCCACTCTCCTGAGTA |
| 3s-510-si | SEQ ID NO. 304: | ctagTACTCAGGAGAGTGGCAATCAC |
| 5x-510-mi | SEQ ID NO. 305: | tcgacaGATTGCCtgaCTCCTGAGTA |
| 3s-510-mi | SEQ ID NO. 306: | ctagTACTCAGGAGTCAGGCAATCTG |
| hsa-mir-660 | | |
| 5Xho-660 | SEQ ID NO. 307: | tatCTCGAgcactgcttctccaggcgtg |
| 3Bam-660 | SEQ ID NO. 308: | tatGGATCCTGGGGAAGTCTAGGCACC |
| S660-5p-si | SEQ ID NO. 309: | tcgaCAACTCCGATATGCAATGGGTA |
| N660-5p-si | SEQ ID NO. 310: | ggccTACCCATTGCATATCGGAGTTG |
| S660-5p-si-m | SEQ ID NO. 311: | tcgaCAACTCCAATATGCAATGGGTA |
| N660-5p-si-m | SEQ ID NO. 312: | ggccTACCCATTGCATATTGGAGTTG |
| S660-3p-si | SEQ ID NO. 313: | tcgaCCTCCTGTAATCCATGCACACAGGAGGTG |
| N660-3p-si | SEQ ID NO. 314: | ggccCACCTCCTGTGTGCATGGATTACAGGAGG |
| S660-5p-mi | SEQ ID NO. 315: | tcgaGTACTCCGAGTCGCAATGGGTA |
| N660-5p-mi | SEQ ID NO. 316: | ggccTACCCATTGCgacTCGGAGTac |
| 660-5p probe | SEQ ID NO. 317: | CAACTCCGATATGCAATGGGTA |
| hsa-miR-509-3 | | |
| 5Xho-509-2 | SEQ ID NO. 318: | tatCTCgagtggacaggactcaaagc |
| 3Bam-509-2 | SEQ ID NO. 319: | tatGGATCCACGTGTCTGGTGGTCAGGC |
| S509-5p-si | SEQ ID NO. 320: | tcgaTGATTGCCACTGTCTGCAGTA |
| N509-5p-si | SEQ ID NO. 321: | ggccTACTGCAGACAGTGGCAATCA |
| S509-3p-si | SEQ ID NO. 322: | tcgaCTACCCACAGACGTACCAATCA |
| N509-3p-si | SEQ ID NO. 323: | ggccTGATTGGTACGTCTGTGGGTAG |
| 5Xho-509-3 | SEQ ID NO. 324: | tatCTCGAGtgggagtggacagcactcaa |
| 3Bam-509-3 | SEQ ID NO. 325: | tatGGATCCAAATTCCTAGACCATGTGTC |
| 5S-509-3-5p-si | SEQ ID NO. 326: | tcgaCATGATTGCCACGTCTGCAGTA |
| 3N-509-3-5p-si | SEQ ID NO. 327: | ggccTACTGCAGACGTGGCAATCATG |
| 5S-509-3CT-3p-si | SEQ ID NO. 328: | tcgaCTACCCACAAACGTACCAATCA |
| 3N-509-3CT-3p-si | SEQ ID NO. 329: | ggccTGATTGGTACGTTTGTGGGTAG |
| 5S-509-3CG-5p-si | SEQ ID NO. 330: | tcgaCATCATTGCCACGTCTGCAGTA |
| 3N-509-3CG-5p-si | SEQ ID NO. 331: | ggccTACTGCAGACGTGGCAATGATG |
| S509-3-5p-mi | SEQ ID NO. 332: | tcgaGTTGATTGCGTGGTCTGCAGTA |
| N509-3-5p-mi | SEQ ID NO. 333: | ggccTACTGCAGACcacGCAATCAac |
| U2A probe | SEQ ID NO. 334: | AGAACAGATACTACACTTGA |
| S1-27 mer siRNA | | |
| Sense | SEQ ID NO. 335: | GCGGAGACAGCGACGAAGAGCUCAUCA |
| Antisense | SEQ ID NO. 336: | UGAUGAGCUCUUCGUCGCUGUCUCCGC |
| Probe (Detect antisense) | SEQ ID NO. 337: | GCGGAGACAGCGACGAAGAGCTCATCA |

TABLE 8

List of all miRNA gene variants that were found in the control population or the patient samples.

| miRNA | Variants |
|---|---|
| hsa-let-7f-2 | 5p 11: G > A |
| hsa-miR-18b | Stem-loop 32: A > G |
| hsa-miR-188 | 3p 60: C > T |
| hsa-miR-224 | Stem-loop 41: G > A |
| hsa-miR-325 | Stem-loop 66/3p 6: G > A |
| hsa-miR-421 | Stem-loop 73: G > A |
| hsa-miR-421 | 4 nt downstream of the 3' end of the stem-loop: G > A |
| hsa-miR-450a-2 | 5p 4: T > C |
| has-miR-502 | Stem-loop 13: C > G |
| has-miR-505 | Stem-loop 8: C > T |
| hsa-miR-509-1 | Stem-loop 54: ins TGA |
| hsa-miR-509-2 | Stem-loop 9: G > T |
| hsa-miR-509-2 | 5p 11: 'A' Deletion |
| hsa-miR-509-3 | 5p 22: G > A |
| hsa-miR-509-3 | 5p 19: C > G |
| hsa-miR-509-3 | 3p 13: C > T |
| hsa-miR-510 | Stem-loop 48/3p 4: T > C |
| hsa-miR-510 | Stem-loop 6: G > A |
| hsa-miR-660 | 5p 15: C > T |
| hsa-miR-888 | Stem-loop 77: A > C |
| hsa-miR-890 | Stem-loop 66: G > C |
| hsa-miR-891b | Stem-loop 35: C > G |
| hsa-miR-892b | 3p 15: T > C |
| hsa-miR-934 | 5p 1: T > G |

The invention claimed is:

1. A method of diagnosing certain cases of schizophrenia or a schizophrenia spectrum disorder in a human individual, the method comprising:
   a. obtaining a nucleic acid sample from the individual; and
   b. determining the presence of one or more variants of a microRNA (miRNA) gene or allele in the sample, the one or more variants selected from the group consisting of:
      a G to A substitution at position 18 of let-7f-2 (SEQ ID NO:2);
      an A to G substitution at position 32 of mir-18b (SEQ ID NO:4);
      a C to T(U) substitution at position 8 of mir-505 (SEQ ID NO:19);
      a C to G substitution at position 13 of mir-502 (SEQ ID NO:17);
      a C to T(U) substitution at position 60 of mir-188 (SEQ ID NO:6);
      a G to A substitution at position 60 of mir-325 (SEQ ID NO:10);
      a C to T(U) substitution at position 30 of mir-660 (SEQ ID NO:33);
      a C to T(U) substitution at position 56 of mir-509-3 (SEQ ID NO:26);
      a G to A substitution at position 6 of mir-510 (SEQ ID NO:30);
      a G to A substitution at position 73 of mir-421 (SEQ ID NO:12);
      a T(U) to G substitution at position 15 of mir-934; (SEQ ID NO 43);
      a G to C substitution at position 66 of mir-890 (SEQ ID NO:37);
      a T(U) to C substitution at position 60 of mir-892 (SEQ ID NO:41);
      a T(U) to C substitution at position 26 of mir-450a-2 (SEQ ID NO:15); and diagnosing schizophrenia or a schizophrenia spectrum disorder in the individual when the one or more variants are present.

2. The method of claim 1, wherein determining the presence of one or more of the variants of an miRNA gene or allele comprises:
   a) isolating miRNA from a sample taken from an individual; and
   b) performing a Northern blot to detect the one or more variants of miRNA, which variants indicate schizophrenia or a schizophrenia spectrum disorder.

3. A method of determining an increased risk for developing schizophrenia or propensity thereto in a human subject comprising the steps of:
   a) isolating the miRNA in a sample obtained from the subject; and
   b) determining the presence of one or more variants of miRNA in the sample, the one or more variants selected from the group consisting of:
      a G to A substitution at position 18 of let-7f-2 (SEQ ID NO:2);
      an A to G substitution at position 32 of mir-18b (SEQ ID NO:4);
      a C to T(U) substitution at position 8 of mir-505 (SEQ ID NO:19);
      a C to G substitution at position 13 of mir-502 (SEQ ID NO:17);
      a C to T(U) substitution at position 60 of mir-188 (SEQ ID NO:6);
      a G to A substitution at position 60 of mir-325 (SEQ ID NO:10);
      a C to T(U) substitution at position 30 of mir-660 (SEQ ID NO:33);
      a C to T(U) substitution at position 56 of mir-509-3 (SEQ ID NO:26);
      a G to A substitution at position 6 of mir-510 (SEQ ID NO:30);

a G to A substitution at position 73 of mir-421 (SEQ ID NO:12);

a T(U) to G substitution at position 15 of mir-934; (SEQ ID NO 43);

a G to C substitution at position 66 of mir-890 (SEQ ID NO:37);

a T(U) to C substitution at position 60 of mir-892 (SEQ ID NO:41);

a T(U) to C substitution at position 26 of mir-450a-2 (SEQ ID NO:15); and wherein the presence of said variant is indicative of an increased risk for developing schizophrenia in the subject.

* * * * *

```
                          SEQUENCE LISTING

<160> NUMBER OF SEQ ID NOS: 337

<210> SEQ ID NO 1
<211> LENGTH: 83
<212> TYPE: RNA
<213> ORGANISM: Homo sapiens

<400> SEQUENCE: 1
ugugggauga gguaguagau uguauaguuu uagggucaua cccaucuugg agauaacuau      60
acagucuacu gucuuucccc acg                                             83

<210> SEQ ID NO 2
<211> LENGTH: 83
<212> TYPE: RNA
<213> ORGANISM: Homo sapiens

<400> SEQUENCE: 2
ugugggauga gguaguaaau uguauaguuu uagggucaua ccccaucuug gagauaacua     60
uacagucuac ugucuuuccc acg                                             83

<210> SEQ ID NO 3
<211> LENGTH: 71
<212> TYPE: RNA
<213> ORGANISM: Homo sapiens

<400> SEQUENCE: 3
uguguuaagg ugcaucuagu gcaguuagug aagcagcuua gaaucuacug cccuaaaugc     60
cccuucuggc a                                                          71

<210> SEQ ID NO 4
<211> LENGTH: 71
<212> TYPE: RNA
<213> ORGANISM: Homo sapiens

<400> SEQUENCE: 4
uguguuaagg ugcaucuagu gcaguuagug aggcagcuua gaaucuacug cccuaaaugc     60
cccuucuggc a                                                          71

<210> SEQ ID NO 5
<211> LENGTH: 86
<212> TYPE: RNA
<213> ORGANISM: Homo sapiens
```

```
<400> SEQUENCE: 5
ugcucccucu cucacauccc uugcauggug gagggugagc uuucugaaaa ccccucccac    60
augcaggguu ugcaggaugg cgagcc                                        86

<210> SEQ ID NO 6
<211> LENGTH: 86
<212> TYPE: RNA
<213> ORGANISM: Homo sapiens

<400> SEQUENCE: 6
ugcucccucu cucacauccc uugcauggug gagggugagc uuucugaaaa ccccucccau    60
augcaggguu ugcaggaugg cgagcc                                        86

<210> SEQ ID NO 7
<211> LENGTH: 81
<212> TYPE: RNA
<213> ORGANISM: Homo sapiens

<400> SEQUENCE: 7
gggcuuucaa gucacuagug guuccguuua guagaugauu ugcauuguu ucaaaauggu     60 gcccuaguga cuacaaagcc c                                             81

<210> SEQ ID NO 8
<211> LENGTH: 81
<212> TYPE: RNA
<213> ORGANISM: Homo sapiens

<400> SEQUENCE: 8
gggcuuucaa gucacuagug guuccguuua guagaugauu augcauuguu ucaaaauggu    60
gcccuaguga cuacaaagcc c                                             81

<210> SEQ ID NO 9
<211> LENGTH: 98
<212> TYPE: RNA
<213> ORGANISM: Homo sapiens

<400> SEQUENCE: 9
auacagugcu gguuccuag uaggugucca guaaguguuu gugacauaau uuguuuauug     60
aggaccuccu aucaaucaag cacugugcua ggcucugg                           98

<210> SEQ ID NO 10
<211> LENGTH: 98
<212> TYPE: RNA
<213> ORGANISM: Homo sapiens

<400> SEQUENCE: 10
auacagugcu gguuccuag uaggugucca guaaguguuu gugacauaau uuguuuauua     60
aggaccuccu aucaaucaag cacugugcua ggcucugg                           98

<210> SEQ ID NO 11
<211> LENGTH: 90
<212> TYPE: RNA
<213> ORGANISM: Homo sapiens

<400> SEQUENCE: 11
gcacauugua ggccucauua aauguuuguu gaaugaaaaa augaaucauc aacagacauu    60
aauugggcgc cugcucugug aucuccaugg                                    90
```

```
<210> SEQ ID NO 12
<211> LENGTH: 85
<212> TYPE: RNA
<213> ORGANISM: Homo sapiens

<400> SEQUENCE: 12
gcacauugua ggccucauua aauguuuguu gaaugaaaaa augaaucauc aacagacauu    60
aauugggcgc cuacucugug aucuc                                         85

<210> SEQ ID NO 13
<211> LENGTH: 90
<212> TYPE: RNA
<213> ORGANISM: Homo sapiens

<400> SEQUENCE: 13
gcacauugua ggccucauua aauguuuguu gaaugaaaaa augaaucauc aacagacauu    60
aauugggcgc cuacucugug aucuccauag                                    90

<210> SEQ ID NO 14
<211> LENGTH: 100
<212> TYPE: RNA
<213> ORGANISM: Homo sapiens

<400> SEQUENCE: 14
ccaaagaaag augcuaaacu auuuuugcga uguguuccua auauguaaua uaaauguauu    60
ggggacauuu ugcauucaua guuuuguauc aauaauaugg                        100

<210> SEQ ID NO 15
<211> LENGTH: 100
<212> TYPE: RNA
<213> ORGANISM: Homo sapiens

<400> SEQUENCE: 15
ccaaagaaag augcuaaacu auuuucgcga uguguuccua auauguaaua uaaauguauu    60
ggggacauuu ugcauucaua guuuuguauc aauaauaugg                        100

<210> SEQ ID NO 16
<211> LENGTH: 86
<212> TYPE: RNA
<213> ORGANISM: Homo sapiens

<400> SEQUENCE: 16
ugcucccccu cucuaauccu ugcuaucugg gugcuagugc uggcucaaug caaugcaccu    60
gggcaaggau ucagagaggg ggagcu                                        86

<210> SEQ ID NO 17
<211> LENGTH: 86
<212> TYPE: RNA
<213> ORGANISM: Homo sapiens

<400> SEQUENCE: 17
ugcucccccu cuguaauccu ugcuaucugg gugcuagugc uggcucaaug caaugcaccu    60
gggcaaggau ucagagaggg ggagcu                                        86

<210> SEQ ID NO 18
<211> LENGTH: 84
<212> TYPE: RNA
<213> ORGANISM: Homo sapiens

<400> SEQUENCE: 18
gaugcaccca guggggagc caggaaguau ugauguuucu gccaguuuag cgucaacacu    60
```
ugcugguuuc cucucuggag cauc    84

<210> SEQ ID NO 19
<211> LENGTH: 84
<212> TYPE: RNA
<213> ORGANISM: Homo sapiens

<400> SEQUENCE: 19
gaugcacuca gugggggagc caggaaguau ugauguuucu gccaguuuag cgucaacacu    60
ugcugguuuc cucucuggag cauc    84

<210> SEQ ID NO 20
<211> LENGTH: 94
<212> TYPE: RNA
<213> ORGANISM: Homo sapiens

<400> SEQUENCE: 20
caugcugugu gugguacccu acugcagaca guggcaauca uguauaauua aaaaugauug    60
guacgucugu ggguagagua cugcaugaca caug    94

<210> SEQ ID NO 21
<211> LENGTH: 97
<212> TYPE: RNA
<213> ORGANISM: Homo sapiens

<400> SEQUENCE: 21
caugcugugu gugguacccu acugcagaca guggcaauca uguauaauua aaaaugauga    60
uugguacguc ugugggaga guacugcaug acacaug    97

<210> SEQ ID NO 22
<211> LENGTH: 91
<212> TYPE: RNA
<213> ORGANISM: Homo sapiens

<400> SEQUENCE: 22
caugcugugu gugguacccu acugcagaca guggcaauca uguauaauua aaaaugauug    60
guacgucugu ggguagagua cugcaugaca c    91

<210> SEQ ID NO 23
<211> LENGTH: 90
<212> TYPE: RNA
<213> ORGANISM: Homo sapiens

<400> SEQUENCE: 23
caugcugugu gugguacccu acugcagacg uggcaaucau guauaauuaa aaaugauugg    60
uacgucugug gguagaguac ugcaugacac    90

<210> SEQ ID NO 24
<211> LENGTH: 91
<212> TYPE: RNA
<213> ORGANISM: Homo sapiens

<400> SEQUENCE: 24
caugcuguuu gugguacccu acugcagaca guggcaauca uguauaauua aaaaugauug    60
guacgucugu ggguagagua cugcaugaca c    91

<210> SEQ ID NO 25
<211> LENGTH: 75
<212> TYPE: RNA
<213> ORGANISM: Homo sapiens

```
<400> SEQUENCE: 25
gugguacccu acugcagacg uggcaaucau guauaauuaa aaaugauugg uacgucugug    60
gguagaguac ugcau                                                    75

<210> SEQ ID NO 26
<211> LENGTH: 75
<212> TYPE: RNA
<213> ORGANISM: Homo sapiens

<400> SEQUENCE: 26
gugguacccu acugcagacg uggcaaucau guauaauuaa aaaugauugg uacguuugug    60
gguagaguac ugcau                                                    75

<210> SEQ ID NO 27
<211> LENGTH: 75
<212> TYPE: RNA
<213> ORGANISM: Homo sapiens

<400> SEQUENCE: 27
gugguacccu acugcagacg uggcaaucau auauaauuaa aaaugauugg uacgucugug    60
gguagaguac ugcau                                                    75

<210> SEQ ID NO 28
<211> LENGTH: 75
<212> TYPE: RNA
<213> ORGANISM: Homo sapiens

<400> SEQUENCE: 28
gugguacccu acugcagacg uggcaaugau guauaauuaa aaaugauugg uacgucugug    60
gguagaguac ugcau                                                    75

<210> SEQ ID NO 29
<211> LENGTH: 74
<212> TYPE: RNA
<213> ORGANISM: Homo sapiens

<400> SEQUENCE: 29 guggguccu acucaggaga guggcaauca cauguaauua ggugugauug aaaccucuaa     60
gaguggagua acac                                                     74

<210> SEQ ID NO 30
<211> LENGTH: 74
<212> TYPE: RNA
<213> ORGANISM: Homo sapiens

<400> SEQUENCE: 30 guggauccu acucaggaga guggcaauca cauguaauua ggugugauug aaaccucuaa     60
gaguggagua acac                                                     74

<210> SEQ ID NO 31
<211> LENGTH: 74
<212> TYPE: RNA
<213> ORGANISM: Homo sapiens

<400> SEQUENCE: 31 guggguccu acucaggaga guggcaauca cauguaauua ggugugacug aaaccucuaa     60
gaguggagua acac                                                     74
```

```
<210> SEQ ID NO 32
<211> LENGTH: 97
<212> TYPE: RNA
<213> ORGANISM: Homo sapiens

<400> SEQUENCE: 32
cugcuccuuc ucccauaccc auugcauauc ggaguuguga auucucaaaa caccuccugu      60
gugcauggau uacaggaggg ugagccuugu caucgug                              97

<210> SEQ ID NO 33
<211> LENGTH: 97
<212> TYPE: RNA
<213> ORGANISM: Homo sapiens

<400> SEQUENCE: 33
cugcuccuuc ucccauaccc auugcauauu ggaguuguga auucucaaaa caccuccugu      60
gugcauggau uacaggaggg ugagccuugu caucgug                              97

<210> SEQ ID NO 34
<211> LENGTH: 77
<212> TYPE: RNA
<213> ORGANISM: Homo sapiens

<400> SEQUENCE: 34
ggcagugcuc uacucaaaaa gcugucaguc acuuagauua caugugacug acaccucuuu      60
gggugaagga aggcuca                                                    77

<210> SEQ ID NO 35
<211> LENGTH: 77
<212> TYPE: RNA
<213> ORGANISM: Homo sapiens

<400> SEQUENCE: 35
ggcagugcuc uacucaaaaa gcugucaguc acuuagauua caugugacug acaccucuuu      60
gggugaagga aggcucc                                                    77

<210> SEQ ID NO 36
<211> LENGTH: 77
<212> TYPE: RNA
<213> ORGANISM: Homo sapiens

<400> SEQUENCE: 36
ggaagugccc uacuuggaaa ggcaucaguu gcuuagauua cauguaacua uucccuuucu      60
gaguagagua agucuua                                                    77

<210> SEQ ID NO 37
<211> LENGTH: 77
<212> TYPE: RNA
<213> ORGANISM: Homo sapiens

<400> SEQUENCE: 37
ggaagugccc uacuuggaaa ggcaucaguu gcuuagauua cauguaacua uucccuuucu      60
gaguacagua agucuua                                                    77

<210> SEQ ID NO 38
<211> LENGTH: 79
<212> TYPE: RNA
<213> ORGANISM: Homo sapiens

<400> SEQUENCE: 38
ccuuaauccu ugcaacuuac cugagucauu gauucaguaa aacauucaau ggcacauguu      60
```

```
uguuguuagg gucaaaaga                                              79

<210> SEQ ID NO 39
<211> LENGTH: 79
<212> TYPE: RNA
<213> ORGANISM: Homo sapiens

<400> SEQUENCE: 39
ccuuaauccu ugcaacuuac cugagucauu gauugaguaa aacauucaau ggcacauguu    60
uguuguuagg gucaaaaga                                              79

<210> SEQ ID NO 40
<211> LENGTH: 77
<212> TYPE: RNA
<213> ORGANISM: Homo sapiens

<400> SEQUENCE: 40
ugcaaugccc uacucagaaa ggugccauuu auguagauuu uaugucacug gcuccuuucu    60
ggguagagca aggcuca                                                77

<210> SEQ ID NO 41
<211> LENGTH: 77
<212> TYPE: RNA
<213> ORGANISM: Homo sapiens

<400> SEQUENCE: 41
ugcaaugccc uacucagaaa ggugccauuu auguagauuu uaugucacug gcuccuuucc    60
ggguagagca aggcuca                                                77

<210> SEQ ID NO 42
<211> LENGTH: 83
<212> TYPE: RNA
<213> ORGANISM: Homo sapiens

<400> SEQUENCE: 42
agaaauaagg cuucugucua cuacuggaga cacugguagu auaaaaccca gagucuccag    60
uaauggacgg gagccuuauu ucu                                         83

<210> SEQ ID NO 43
<211> LENGTH: 83
<212> TYPE: RNA
<213> ORGANISM: Homo sapiens

<400> SEQUENCE: 43
agaaauaagg cuucggucua cuacuggaga cacugguagu auaaaaccca gagucuccag    60
uaauggacgg gagccuuauu ucu                                         83

<210> SEQ ID NO 44
<211> LENGTH: 75
<212> TYPE: RNA
<213> ORGANISM: Homo sapiens

<400> SEQUENCE: 44
gugguacccu acugcagacg uggcaaucau guauaauuaa aaaugauugg uacgucugug    60
gguagaguac ugcau                                                  75

<210> SEQ ID NO 45
<211> LENGTH: 75
<212> TYPE: RNA
<213> ORGANISM: Homo sapiens
```

-continued

```
<400> SEQUENCE: 45
gugguacccu acugcagacg uggcaaucau guauaauuaa aaaugauugg uacguuugug      60
gguagaguac ugcau                                                      75

<210> SEQ ID NO 46
<211> LENGTH: 75
<212> TYPE: RNA
<213> ORGANISM: Homo sapiens

<400> SEQUENCE: 46
gugguacccu acugcagacg uggcaaucau auauaauuaa aaaugauugg uacgucugug      60
gguagaguac ugcau                                                      75

<210> SEQ ID NO 47
<211> LENGTH: 75
<212> TYPE: RNA
<213> ORGANISM: Homo sapiens

<400> SEQUENCE: 47
gugguacccu acugcagacg uggcaaugau guauaauuaa aaaugauugg uacgucugug      60
gguagaguac ugcau                                                      75

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tagcacccag atagcaagga t                                               21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atccttgcta tctgggtgct a                                               21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgcaccctc ttagcaagga t                                               21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
```
atccttgcta tctgggtgct a                                              21

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tgaatccttg cccaggtgca ttgcatt                                        27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aatgcaatgc acctgggcaa ggattca                                        27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
acaatccttg cccaccagca ttgcatt                                        27

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aatgcaatgc acctgggcaa ggattca                                        27

<210> SEQ ID NO 56
<211> LENGTH: 74
<212> TYPE: RNA
<213> ORGANISM: Homo sapiens

<400> SEQUENCE: 56
gugguguccu acucaggaga guggcaauca cauguaauua ggugugacug aaaccucuaa    60
gaguggagua acac                                                      74

<210> SEQ ID NO 57
<211> LENGTH: 74
<212> TYPE: RNA
<213> ORGANISM: Homo sapiens

<400> SEQUENCE: 57
gugguauccu acucaggaga guggcaauca cauguaauua ggugugauug aaaccucuaa    60
gaguggagua acac                                                      74

```
<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gtgattgcca ctctcctgag ta                                              22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tactcaggag agtggcaatc ac                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cagattgcct gactcctgag ta                                              22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tactcaggag agtggcaatc ac                                              22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ccactcttag aggtttcaat ca                                              22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgattgaaac ctctaagagt gg                                              22

<210> SEQ ID NO 64
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggactcttac tcgtttcaat ca                                                  22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgattgaaac ctctaagagt gg                                                  22

<210> SEQ ID NO 66
<211> LENGTH: 77
<212> TYPE: RNA
<213> ORGANISM: Homo sapiens

<400> SEQUENCE: 66
ggaagugccc uacuuggaaa ggcaucaguu gcuuagauua cauguaacua uucccuuucu         60
gaguagagua agucuua                                                        77

<210> SEQ ID NO 67
<211> LENGTH: 77
<212> TYPE: RNA
<213> ORGANISM: Homo sapiens

<400> SEQUENCE: 67
ggaagugccc uacuuggaaa ggcaucaguu gcuuagauua cauguaacua uucccuuucu         60
gaguacagua agucuua                                                        77

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
caactgatgc ctttccaagt a                                                   21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tacttggaaa ggcatcagtt g                                                   21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 70
gtactgatct gtttccaagt a    21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tacttggaaa ggcatcagtt g    21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tctactcaga aagggaatag t    21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
actattccct ttctgagtag a    21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tgtactcaga aagggaatag t    21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
actattccct ttctgagtac a    21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 76
ggtactcact tagggaatag t                                             21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
actattccct ttctgagtag a                                             21

<210> SEQ ID NO 78
<211> LENGTH: 77
<212> TYPE: RNA
<213> ORGANISM: Homo sapiens

<400> SEQUENCE: 78
ugcaaugccc uacucagaaa ggugccauuu auguagauuu uaugucacug gcuccuuucu   60
ggguagagca aggcuca                                                  77

<210> SEQ ID NO 79
<211> LENGTH: 77
<212> TYPE: RNA
<213> ORGANISM: Homo sapiens

<400> SEQUENCE: 79
ugcaaugccc uacucagaaa ggugccauuu auguagauuu uaugucacug gcuccuuucc   60
ggguagagca aggcuca                                                  77

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
acataaatgg cacctttctg agtag                                         25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctactcagaa aggtgccatt tatgt                                         25

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tctacccaga aaggagccag tg                                            22
```

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cactggctcc tttctgggta ga                                          22

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tctacccgga aaggagccag tg                                          22

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cactggctcc tttccgggta ga                                          22

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
agtacccagt ttggagccag tg                                          22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cactggctcc tttctgggta ga                                          22

<210> SEQ ID NO 88
<211> LENGTH: 83
<212> TYPE: RNA
<213> ORGANISM: Homo sapiens

<400> SEQUENCE: 88
agaaauaagg cuucugucua cuacuggaga cacugguagu auaaaaccca gagucuccag   60
uaauggacgg gagccuuauu ucu                                         83

<210> SEQ ID NO 89
<211> LENGTH: 83

```
<212> TYPE: RNA
<213> ORGANISM: Homo sapiens

<400> SEQUENCE: 89
agaaauaagg cuucggucua cuacuggaga cacugguagu auaaaaccca gagucuccag   60
uaauggacgg gagccuuauu ucu                                          83

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ccagtgtctc cagtagtaga ca                                           22

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tgtctactac tggagacact gg                                           22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ttagtgtctg gtgtagtaga ca                                           22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgtctactac tggagacact gg                                           22

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ccgtccatta ctggagactc t                                            21

<210> SEQ ID NO 95
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 95
agagtctcca gtaatggacg g                                              21

<210> SEQ ID NO 96
<211> LENGTH: 71
<212> TYPE: RNA
<213> ORGANISM: Homo sapiens

<400> SEQUENCE: 96
uguguuaagg ugcaucuagu gcaguuagug aaacagcuua gaaucuacug cccuaaaugc    60
cccuucuggc a                                                        71

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cagttattca gaaacattat agg                                            23

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aggcagttgt gttgaaatag ta                                             22

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttattaaaga ctgcccaata atc                                            23

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cttccacaga gcccctcc                                                  18

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 101 agcatacccca tatgtcgtgc                                          20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tggtgaagga gtgcgtatgt                                           20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gaggcaacac tgctaagact                                           20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cttttgcctg ctgcccttat                                           20

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccagaacaag aacctgaaca g                                         21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cctgatagtt ccgagtagct                                           20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107

-continued acatctccca ggaagatctc                                              20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggcagtccat tcgtcatatc                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
accactaggc ctaagtacct                                              20

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gcttaaatat aggttttgag atg                                          23

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gatgcttcta aagaaacggt g                                            21

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tagcagtggc acgcttgac                                               19

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tctggtgctt acctactgtc                                              20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tggggaccca tcatcaaaag                                          20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aggagctcac agtctaactg                                          20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gttcctcacc tctcttgatg                                          20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gccagttagc atcttgaagg                                          20

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gttccttgcc ttttaactag tat                                      23

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tccagctgac gcacttgct                                           19

<210> SEQ ID NO 120

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gatgcagtag gtctcattcg                                                  20

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ctaaatatca gaacttacgg ct                                               22

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gtgaacacac cttcatgcgt                                                  20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tgagtgctgg agatacgcat                                                  20

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ctcttggata acaaatctct tg                                               22

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ttatgcacaa actacagttc tc                                               22

<210> SEQ ID NO 126
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 126
agaagagctc ctggaagact                                                   20

<210> SEQ ID NO 127
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gggagcgggc acctggt                                                      17

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gcttccttca gtcatccagt                                                   20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
aatggctttg gtccagaagc                                                   20

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ctactcctat atattggatg tc                                                22

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gagtggcttt gttccagaag                                                   20

<210> SEQ ID NO 132
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 132
gtctactccc tataacctgg                                                 20

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cttgtgatgt agattaaatc gt                                              22

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cactttattc atcctgactc t                                               21

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgtacacaag cacaccttct                                                 20

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gaagcaggac agtcatcca                                                  19

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gcacctgaca ctttaatctc a                                               21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ctaatacctc cactagatag g                                             21

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tgtttgtgtg ctatggccat                                               20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gttctcctat atgatggctc                                               20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tatgtatctc gtggatctgc                                               20

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ttacaagata ggaagtgcat at                                            22

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cattgtccgt gtctatggc                                                19

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
aattggagat ggtacttgag a                                             21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
tatacacaga ggattgctta g                                             21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cctcattact ctcatttcct g                                             21

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
atcgctgact tgtgtcacta                                               20

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tattctaggc ccactgctg                                                19

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ttcagggttc aggcatcct                                                19

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acacctaagg ttcaggtgg                                                19

<210> SEQ ID NO 151
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gacatcatgc tgtgctcag                                                    19

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tgcctgaatt ccaggtggt                                                    19

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tccagattca ggcatcctg                                                    19

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ttaaggatgc ctgaggttca                                                   20

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
tcaaattgtt caggcatcat g                                                 21

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acatggccag ctaggttct                                                    19

```
<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tagctacata ggtcgtgaat a                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ctactaccag tatcactaca a                                              21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
catgctgata gttacacagg                                                20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
actaccagtg tcactacaag                                                20

<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ccaaattcca atggccacg                                                 19

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
atttggatgt tggagtaggc                                                20

<210> SEQ ID NO 163
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tctgtgagta acaggaccta                                              20

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
tgagaaagga agctaaccat t                                            21

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tgatatctcc tccagcatca                                              20

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tgatctaaga gtagagagtc a                                            21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gtaaagtgtt tgtcataggc a                                            21

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
cctacaatgt gcaccggat                                               19

<210> SEQ ID NO 169
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 169
ggtgggatta gagctgaag                                                    19

<210> SEQ ID NO 170
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ggcattccca ttacactcc                                                    19

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
caagttgcat tgtcccttgg                                                   20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tggagtaaag cattccagct                                                   20

<210> SEQ ID NO 173
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gtagcaatgt ctttgaatat tc                                                22

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tgttgggaac agatggtgg                                                    19

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                              primer

<400> SEQUENCE: 175
acatgcacac atacaaacac a                                              21

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
atagcaaaca caaacatgtg aa                                             22

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
accactgaaa tgtgtcctat t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gagaactgta gtttgtgcat a                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
atgtgctaag aaaagcatac c                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
agaggttgtt tgaaaagtgt g                                              21

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 181
tagcttactg tagcgctgat                                                   20

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
acttgtcccg gcctgtgg                                                     18

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tgcaatcttg ggtctcgct                                                    19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gggcagtatt cctggctag                                                    19

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
aagctcaaga actgttctct t                                                 21

<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
ataaatactt gtggaatgga tg                                                22

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
```

```
cagagatact ttgcaggaat g                                            21
```

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188

```
aagaatgaat gagggtcaga g                                            21
```

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189

```
atgatgcaaa tgagtattag ga                                           22
```

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190

```
ttctagatta tgggtcattc c                                            21
```

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191

```
gccagctgca cattccga                                                18
```

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192

```
gttggtaagc gtgccagg                                                18
```

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193

```
aagagactta tcaggattga g                                            21
```

```
<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ccatccattt cccacataga                                               20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tcacctaata ttcctgcacg                                               20

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
ggtgatgtct aggctctct                                                19

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tgatggtggt ggcactgac                                                19

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
tcctagtgga ctgagagtgt                                               20

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
caaagaactg tgtaggaagg a                                             21

<210> SEQ ID NO 200
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tcatcactcg acagtgatgg                                                20

<210> SEQ ID NO 201
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gtccagcatg gaagtggag                                                 19

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tggattggat tctgcagaag t                                              21

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tggacaaagg acttctgtag                                                20

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tagtgcatat taggaacaca tc                                             22

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ataggtatat agggagcatt ct                                             22

<210> SEQ ID NO 206
<211> LENGTH: 21
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 206
cacagaagta aaccacagat a                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ttgtggtata aaggtgacca a                                              21

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ccaggccaga agaggctt                                                  18

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
aaggtcatag cagtcagtac                                                20

<210> SEQ ID NO 210
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
aagacctgcc tatgggagt                                                 19

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
actgaagaga agaagtcctc                                                20

<210> SEQ ID NO 212
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 212
cagattctgg agcagatctc                                              20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
cagaactacc cactcagtga                                              20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gagtccacag ttcctatgta                                              20

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
ctcacttggg gcaggatg                                                18

<210> SEQ ID NO 216
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
attatctcga gaatctctca ggtaactctc c                                 31

<210> SEQ ID NO 217
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
attatggatc cagagttgca gtcaggaaat g                                 31

<210> SEQ ID NO 218
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 218
tcgaaactat acaatctact acctca                                              26

<210> SEQ ID NO 219
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ctagtgaggt agtagattgt atagtt                                              26

<210> SEQ ID NO 220
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tcgaaactat acaatttact acctca                                              26

<210> SEQ ID NO 221
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ctagtgaggt agtaaattgt atagtt                                              26

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gggatgaggt agtaaattgt atagttttag                                          30

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ctaaaactat acaatttact acctcatccc                                          30

<210> SEQ ID NO 224
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
```
tcgagggtat acggtctact acctca                                            26

<210> SEQ ID NO 225
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ctagtgaggt agtagaccgt ataccc                                            26

<210> SEQ ID NO 226
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tcgagggtat acggtttact acctca                                            26

<210> SEQ ID NO 227
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ctagtgaggt agtaaaccgt ataccc                                            26

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
aactatacaa tctactacct ca                                                22

<210> SEQ ID NO 229
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tatctcgagc tactgagaac tgtagtttgt gca                                    33

<210> SEQ ID NO 230
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tatggatcca ctgaaatgtg tcctattcaa att                                    33

```
<210> SEQ ID NO 231
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tcgactaact gcactagatg caccttta                                             27

<210> SEQ ID NO 232
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ctagtaaggt gcatctagtg cagttag                                              27

<210> SEQ ID NO 233
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tcgagaaact gcacatcatg caccttta                                             27

<210> SEQ ID NO 234
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ctagtaaggt gcatgatgtg cagtttc                                              27

<210> SEQ ID NO 235
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tcgagccaga gggggcattt agggca                                               26

<210> SEQ ID NO 236
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ctagtgccct aaatgcccct tctggc                                               26
```

```
<210> SEQ ID NO 237
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tcgacgcaga aggccgattt agggca                                         26

<210> SEQ ID NO 238
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ctagtgccct aaatcggcct tctgcg                                         26

<210> SEQ ID NO 239
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
tatctcgagc atactgtcat tgaaagcact tac                                 33

<210> SEQ ID NO 240
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tatggatcct gagcaaatga atgggagcag taa                                 33

<210> SEQ ID NO 241
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tcgaaggaaa ccagcaagtg ttgacg                                         26

<210> SEQ ID NO 242
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ctagcgtcaa cacttgctgg tttcct                                         26

<210> SEQ ID NO 243
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tcgatcgaaa ccacgtagtg ttgacg                                              26

<210> SEQ ID NO 244
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ctagcgtcaa cactacgtgg tttcga                                              26

<210> SEQ ID NO 245
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tcgaacatca atacttcctg gctccc                                              26

<210> SEQ ID NO 246
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246 ctagggagc caggaagtat tgatgt                                               26

<210> SEQ ID NO 247
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tcgatgatca atagaacctg gctccc                                              26

<210> SEQ ID NO 248
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248 ctagggagc caggttctat tgatca                                               26

<210> SEQ ID NO 249
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 249
tatctcgaga atatgtgtag gagacttg                                           28

<210> SEQ ID NO 250
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tatggatcct gtctcactct ggatacctg                                          29

<210> SEQ ID NO 251
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tcgatagcac ccagatagca aggat                                              25

<210> SEQ ID NO 252
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ctagatcctt gctatctggg tgcta                                              25

<210> SEQ ID NO 253
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tcgaatgcac cctcttagca aggat                                              25

<210> SEQ ID NO 254
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ctagatcctt gctaagaggg tgcat                                              25

<210> SEQ ID NO 255
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 255
tcgatgaatc cttgcccagg tgcatt                                        26

<210> SEQ ID NO 256
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 256
ctagaatgca cctgggcaag gattca                                        26

<210> SEQ ID NO 257
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 257
tcgaacaatc cttcggcagg tgcatt                                        26

<210> SEQ ID NO 258
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 258
ctagaatgca cctgccgaag gattgt                                        26

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 259
tagcacccag atagcaagga t                                              21

<210> SEQ ID NO 260
<211> LENGTH: 25
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 260
aatccttgcc caggtgcatt gcatt                                         25

<210> SEQ ID NO 261
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide

```
<400> SEQUENCE: 261
tatctcgagc tgcccacttg cacccccag gcc                              33

<210> SEQ ID NO 262
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tatggatccc accacatggg tgtgtgtttt tct                             33

<210> SEQ ID NO 263
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tcgaccctcc accatgcaag ggatg                                      25

<210> SEQ ID NO 264
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ctagcatccc ttgcatggtg gaggg                                      25

<210> SEQ ID NO 265
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tcgaggctcc acgtagcaag ggatg                                      25

<210> SEQ ID NO 266
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ctagcatccc ttgctacgtg gagcc                                      25

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
```
tcgatgcaaa ccctgcatgt gggag                                              25

<210> SEQ ID NO 268
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ctagctccca catgcagggt ttgca                                              25

<210> SEQ ID NO 269
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tcgaaccaaa ccgaccatgt gggag                                              25

<210> SEQ ID NO 270
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ctagctccca catggtcggt ttggt                                              25

<210> SEQ ID NO 271
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
tcgatgcaaa ccctgcatat gggag                                              25

<210> SEQ ID NO 272
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ctagctccca tatgcagggt ttgca                                              25

<210> SEQ ID NO 273
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tcgaaccaaa ccgaccatat gggag                                              25

```
<210> SEQ ID NO 274
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ctagctccca tatggtcggt ttggt                                              25

<210> SEQ ID NO 275
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tatctcgagg ttctgtgaga aaaagttgct taa                                     33

<210> SEQ ID NO 276
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tatggatcct aaccaccact aggcctaagt acc                                     33

<210> SEQ ID NO 277
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cataatttgt ttattaagga cctcctatca a                                       31

<210> SEQ ID NO 278
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ttgataggag gtccttaata aacaaattat g                                       31

<210> SEQ ID NO 279
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tatctcgaga cagggattgt atggctta                                           28

<210> SEQ ID NO 280
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tatggatcct caacacactg aaatctg                                          27

<210> SEQ ID NO 281
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tatctcgaga ttcaagtcca cagaacca                                         28

<210> SEQ ID NO 282
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tatggatcct caaaatgtag gatgttg                                          27

<210> SEQ ID NO 283
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
tcgaacaaac acttactgga cacctactag gaa                                   33

<210> SEQ ID NO 284
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ctagttccta gtaggtgtcc agtaagtgtt tgt                                   33

<210> SEQ ID NO 285
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tcgattgata ggaggtcctc aataaacaaa tt                                    32

<210> SEQ ID NO 286
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 286
ctagaatttg tttattgagg acctcctatc aa                                  32

<210> SEQ ID NO 287
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tcgaacactt actggacacc tactagg                                        27

<210> SEQ ID NO 288
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ctagcctagt aggtgtccag taagtgt                                        27

<210> SEQ ID NO 289
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tcgatgactt actgctgacc tactagg                                        27

<210> SEQ ID NO 290
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ctagcctagt aggtcagcag taagtca                                        27

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
tatctcgagt cctgaaaact gcca                                           24

<210> SEQ ID NO 292
<211> LENGTH: 29
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 292
tatggatcct tgcaagtttg taaagaagg                                           29

<210> SEQ ID NO 293
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 293
gtgattgcca ctctcctgag ta                                                  22

<210> SEQ ID NO 294
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 294
ccactcttag aggtttcaat ca                                                  22

<210> SEQ ID NO 295
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tcgaccactc ttagaggttt caatca                                              26

<210> SEQ ID NO 296
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
ctagtgattg aaacctctaa gagtgg                                              26

<210> SEQ ID NO 297
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tcgaggactc ttactcgttt caatca                                              26

<210> SEQ ID NO 298
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 298
ctagtgattg aaacgagtaa gagtcc                                              26

<210> SEQ ID NO 299
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tcgaccactc ttagaggttt cagtca                                              26

<210> SEQ ID NO 300
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
ctagtgactg aaacctctaa gagtgg                                              26

<210> SEQ ID NO 301
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tcgaggactc ttactcgttt cagtca                                              26

<210> SEQ ID NO 302
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ctagtgactg aaacgagtaa gagtcc                                              26

<210> SEQ ID NO 303
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
tcgagtgatt gccactctcc tgagta                                              26

<210> SEQ ID NO 304
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
```
ctagtactca ggagagtggc aatcac    26

<210> SEQ ID NO 305
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 305
tcgacagatt gcctgactcc tgagta    26

<210> SEQ ID NO 306
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 306
ctagtactca ggagtcaggc aatctg    26

<210> SEQ ID NO 307
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 307
tatctcgagc actgcttctc caggcgtg    28

<210> SEQ ID NO 308
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 308
tatggatcct ggggaagtct aggcacc    27

<210> SEQ ID NO 309
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 309
tcgacaactc cgatatgcaa tgggta    26

<210> SEQ ID NO 310
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 310
ggcctaccca ttgcatatcg gagttg    26

<210> SEQ ID NO 311
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
tcgacaactc caatatgcaa tgggta                                           26

<210> SEQ ID NO 312
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
ggcctaccca ttgcatattg gagttg                                           26

<210> SEQ ID NO 313
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tcgacctcct gtaatccatg cacacaggag gtg                                   33

<210> SEQ ID NO 314
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ggcccacctc ctgtgtgcat ggattacagg agg                                   33

<210> SEQ ID NO 315
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tcgagtactc cgagtcgcaa tgggta                                           26

<210> SEQ ID NO 316
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ggcctaccca ttgcgactcg gagtac                                           26

<210> SEQ ID NO 317
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 317
caactccgat atgcaatggg ta                                              22

<210> SEQ ID NO 318
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tatctcgagt ggacaggact caaagc                                          26

<210> SEQ ID NO 319
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tatggatcca cgtgtctggt ggtcaggc                                        28

<210> SEQ ID NO 320
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tcgatgattg ccactgtctg cagta                                           25

<210> SEQ ID NO 321
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
ggcctactgc agacagtggc aatca                                           25

<210> SEQ ID NO 322
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tcgactaccc acagacgtac caatca                                          26

<210> SEQ ID NO 323
<211> LENGTH: 26

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ggcctgattg gtacgtctgt gggtag                                          26

<210> SEQ ID NO 324
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tatctcgagt gggagtggac agcactcaa                                       29

<210> SEQ ID NO 325
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tatggatcca aattcctaga ccatgtgtc                                       29

<210> SEQ ID NO 326
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tcgacatgat tgccacgtct gcagta                                          26

<210> SEQ ID NO 327
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ggcctactgc agacgtggca atcatg                                          26

<210> SEQ ID NO 328
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tcgactaccc acaaacgtac caatca                                          26

<210> SEQ ID NO 329
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 329
ggcctgattg gtacgtttgt gggtag                                          26

<210> SEQ ID NO 330
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tcgacatcat tgccacgtct gcagta                                          26

<210> SEQ ID NO 331
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ggcctactgc agacgtggca atgatg                                          26

<210> SEQ ID NO 332
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tcgagttgat tgcgtggtct gcagta                                          26

<210> SEQ ID NO 333
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
ggcctactgc agaccacgca atcaac                                          26

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 334
agaacagata ctacacttga                                                 20

<210> SEQ ID NO 335
<211> LENGTH: 27
<212> TYPE: RNA
<213> ORGANISM: Artificial Sequence
<220> FEATURE:
<223> OTHER INFORMATION: Description of Artificial Sequence: Synthetic
```

```
oligonucleotide

<400> SEQUENCE: 335
gcggagacag cgacgaagag cucauca                                              27

<210> SEQ ID NO 336
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ugaugagcuc uucgucgcug ucuccgc                                              27

<210> SEQ ID NO 337
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 337
gcggagacag cgacgaagag ctcatca                                              27
```